(12) United States Patent
Mikamiyama et al.

(10) Patent No.: US 7,745,453 B2
(45) Date of Patent: Jun. 29, 2010

(54) HYDROXYPYRIMIDINONE DERIVATIVES HAVING INHIBITORY ACTIVITY AGAINST HIV INTEGRASE

(75) Inventors: Hidenori Mikamiyama, Osaka (JP); Minamo Iwata, Osaka (JP); Yoshiyuki Taoda, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 866 days.

(21) Appl. No.: 10/583,796

(22) PCT Filed: Dec. 21, 2004

(86) PCT No.: PCT/JP2004/019048

§ 371 (c)(1),
(2), (4) Date: Jun. 21, 2006

(87) PCT Pub. No.: WO2005/061490

PCT Pub. Date: Jul. 7, 2005

(65) Prior Publication Data

US 2007/0149556 A1  Jun. 28, 2007

(30) Foreign Application Priority Data

Dec. 22, 2003  (JP) .............................. 2003-423947

(51) Int. Cl.
A61K 31/505 (2006.01)
C07D 239/02 (2006.01)
C07D 401/00 (2006.01)
C07D 403/00 (2006.01)
C07D 405/00 (2006.01)
C07D 409/00 (2006.01)
C07D 411/00 (2006.01)
C07D 413/00 (2006.01)
C07D 417/00 (2006.01)
C07D 419/00 (2006.01)

(52) U.S. Cl. ...................... 514/269; 544/309; 544/310
(58) Field of Classification Search ...................... None
See application file for complete search history.

(56) References Cited

U.S. PATENT DOCUMENTS

2004/0229909 A1   11/2004   Kiyama et al.

FOREIGN PATENT DOCUMENTS

| WO | 03/016275 | 2/2003 |
| WO | 03/035076 | 5/2003 |
| WO | 03/035077 | 5/2003 |

OTHER PUBLICATIONS

Dorwald F. A. Side Reactions in Organic Synthesis, 2005, Wiley: VCH, Weinheim p. IX of Preface.*

Vippagunta et. al. Advanced Drug Delivery Reviews 48 (2001) 3-26.*

* cited by examiner

*Primary Examiner*—James O Wilson
*Assistant Examiner*—Jeffrey H Murray
(74) *Attorney, Agent, or Firm*—Wenderoth, Lind & Ponack, L.L.P.

(57) ABSTRACT

Compounds of Formula (1), pharmaceuticals containing the same, especially anti-HIV agents having anti viral activity, especially inhibitory activity against HIV integrase,

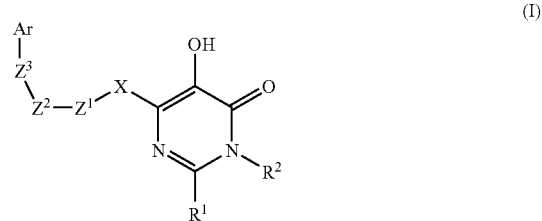

wherein X represents either one of the following groups:

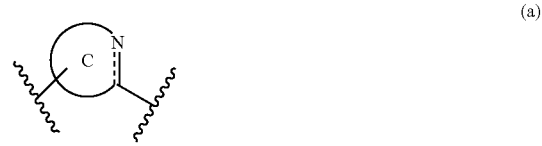

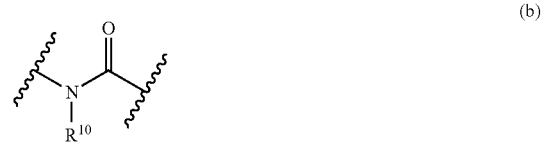

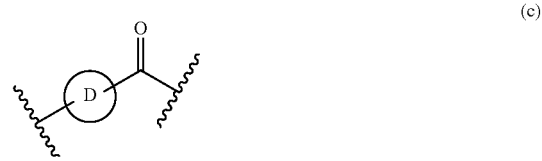

(wherein, C ring is nitrogen-containing aromatic heterocyclic ring in which at least one atom in atoms neighboring the atom bound to the pyrimidine ring is unsubstituted nitrogen atom; $R^{10}$ is hydrogen or lower alkyl; D ring is aryl or heteroaryl) $Z^1$ and $Z^3$ each is independently a single bond, O, S, S(=O) or $SO_2$; $Z^2$ is a single bond, lower alkylene or lower alkenylene; Ar is optionally substituted aryl or optionally substituted heteroaryl; $R^1$ is lower alkyl, substituted lower alkyl or the like; $R^2$ is a hydrogen atom or optionally substituted lower alkyl; or $R^1$ and $R^2$ may form, together with an adjacent atom, an optionally substituted heterocyclic ring, a pharmaceutically acceptable salt or a solvate thereof.

12 Claims, No Drawings

HYDROXYPYRIMIDINONE DERIVATIVES HAVING INHIBITORY ACTIVITY AGAINST HIV INTEGRASE

TECHNICAL FIELD

The present invention relates to novel compounds having antiviral activities, in detail hydroxypyrimidinone derivatives having inhibitory activity against HIV integrase and a pharmaceuticals containing the same, especially an anti-HIV agent.

BACKGROUND ART

Among viruses, human immunodeficiency virus (HIV), a kind of retrovirus, is known to cause acquired immunodeficiency syndrome (AIDS). The therapeutic agent for AIDS is mainly selected from a group of reverse transcriptase inhibitors (e.g., AZT, 3TC) and protease inhibitors (e.g., Indinavir), but they are proved to be accompanied by side effects such as nephropathy and the emergence of resistant viruses. Thus, the development of anti-HIV agents having the other mechanism of action has been desired.

On the other hand, a multidrug combination therapy is reported to be efficient in treatment for acquired immunodeficiency syndrome (AIDS) because of the frequent emergence of the resistant mutant. Reverse transcriptase inhibitors and protease inhibitors are clinically used as an anti-HIV agent, however agents having the same mechanism of action often exhibit cross-resistance or only an additional activity. Therefore, anti-HIV agents having the other mechanism of action are desired.

As an integrase inhibitor, for example, hydroxypyrimidinone derivatives substituted with a heterocyclic group are known (see Patent document 1). Hydroxypyrimidinone derivatives substituted with a carbamoyl group are also known (see Patent document 2, 3).

Additionally, condensed compounds of hydroxypyrimidinone derivative described in Patent documents 2 and 3 are known (see Patent documents 4 to 6).

[Patent document 1]

WO 2003/16275

[Patent document 2]

WO 2003/35076

[Patent document 3]

WO 2003/35077

[Patent document 4]

WO 2004/58756

[Patent document 5]

WO 2004/58757

[Patent document 6]

WO 2004/62613

Under the above circumstance, the development of a novel integrase inhibitor has been desired.

DISCLOSURE OF INVENTION

The present inventors have intensively studied to find that a novel hydroxypyrimidinone derivative has a strong inhibitory activity against HIV integrase. Moreover, the present inventors have discovered that a compound of the present invention and a pharmaceuticals containing the same are useful as an antiviral agent (e.g., an antiretroviral agent, an anti-HIV agent, an anti-HTLV-1 (Human T cell leukemia virus type 1) agent, an anti-FIV (Feline immunodeficiency virus) agent or an anti-SIV (Simian immunodeficiency virus) agent), especially an anti-HIV agent or, an anti-AIDS agent, pharmaceutical agents for related diseases and the like, to accomplish the present invention.

Specifically, the present invention relates to the following inventive features:

(1) A compound of the formula:

[Formula 1]

(I)

(wherein:

X represents either one of the following groups:

[Formula 2]

(a)  (b)  (c)

(wherein, C ring is nitrogen-containing aromatic heterocyclic ring in which at least one atom in atoms neighboring the atom bound to the pyrimidine ring is unsubstituted nitrogen atom; $R^{10}$ is hydrogen or lower alkyl; D ring is aryl or heteroaryl) $Z^1$ and $Z^3$ each is independently a single bond, O, S, S(=O) or $SO_2$;

$Z^2$ is a single bond, lower alkylene or lower alkenylene;

Ar is optionally substituted aryl or optionally substituted heteroaryl;

$R^1$ is lower alkyl, substituted lower alkyl, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl;

$R^2$ is a hydrogen atom or optionally substituted lower alkyl; or $R^1$ and $R^2$ may form, together with an adjacent atom, an optionally substituted heterocyclic ring, provided that 1) when X is a group shown by (a). $R^1$ is not lower alkyl 2) when X is a group shown by (b), $R^1$ and $R^2$ form, together with an adjacent atom, a heterocyclic ring shown by the (d) as follows:

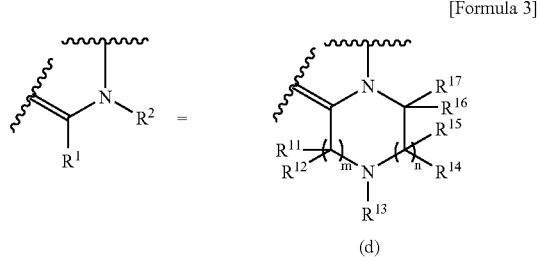

[Formula 3]

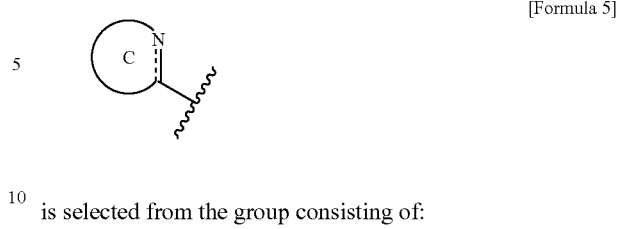

[Formula 5]

is selected from the group consisting of:

[Formula 6]

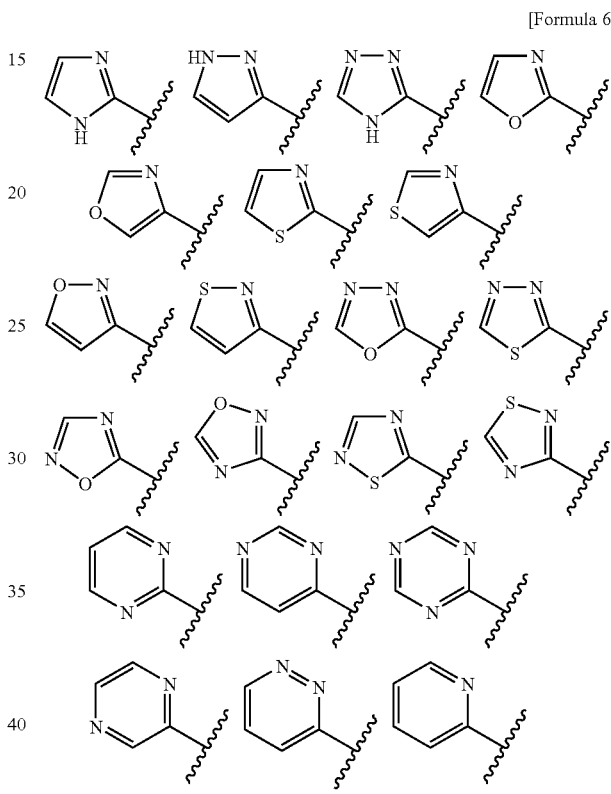

(wherein, $R^{11}$, $R^{12}$, $R^{14}$, $R^{15}$, $R^{16}$, and $R^{17}$ each is independently hydrogen, optionally substituted lower alkyl, optionally substituted aryl, optionally substituted heteroaryl, optionally substituted amino, optionally substituted hydroxy, optionally substituted thiol, optionally substituted sulfonyl, optionally substituted aminosulfonyl, or optionally substituted carbamoyl, or $R^{11}$ and $R^{12}$, $R^{14}$ and $R^{15}$, and $R^{16}$ and $R^{17}$ may together form "=O". $R^{13}$ is hydrogen, optionally substituted lower alkyl, optionally substituted lower alkylcarbonyl, optionally substituted lower alkylsulfonyl, optionally substituted carbamoyl, optionally substituted arylcarbonyl, optionally substituted aralkyl, optionally substituted heteroaralkyl, or optionally substituted heteroarylcarbonyl;

m is 0, 1, 2 or 3; n is 0, 1, 2 or 3; provided that $1 \leq m+n \leq 3$)), a pharmaceutically acceptable salt or a solvate thereof.

(2) A compound according to the above (1), wherein $Z^1$ is a single bond or O; $Z^2$ is a single bond or lower alkylene; $Z^3$ is a single bond; and Ar is optionally substituted phenyl, a pharmaceutically acceptable salt or a solvate thereof.

(3) A compound according to the above (2), wherein —$Z^1$—$Z^2$—$Z^3$—Ar is 4-fluorobenzyl, a pharmaceutically acceptable salt or a solvate thereof.

(4) A compound according to the above (1) represented by the formula:

[Formula 4]

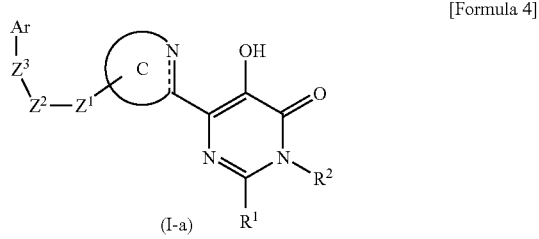

(wherein each symbol has the same meanings as above (1)), a pharmaceutically acceptable salt or a solvate thereof.

(5) A compound according to the above (4), wherein C ring represented by the formula:

a pharmaceutically acceptable salt or a solvate thereof.

(6) A compound according to the above (5), wherein C ring is selected from the group consisting of:

[Formula 7]

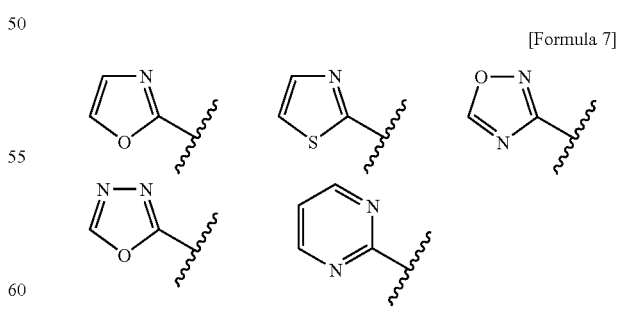

a pharmaceutically acceptable salt or a solvate thereof.

(7) A compound according to the above (1), wherein $R^1$ is substituted lower alkyl, optionally substituted cycloalkyl, optionally substituted aralkyl, optionally substituted heterocyclic lower alkyl, optionally substituted aryl or optionally substituted heterocyclic group, and each substituent is selected from the group consisting of —NR$^3$R$^4$, —C(=O)R$^3$, —C(O)NR$^3$R$^4$ (wherein, R$^3$ and R$^4$ each is independently, hydrogen atom, hydroxy, alkoxy, optionally substituted aryloxy, optionally substituted aralkyloxy, optionally substituted amino, optionally substituted alkyl, optionally substituted cycloalkyl, optionally substituted aryl, optionally substituted heterocyclic group, optionally substituted aralkyl, optionally substituted heteroaralkyl, optionally substituted lower alkylcarbonyl, optionally substituted arylcarbonyl, optionally substituted heteroarylcarbonyl, optionally substituted carbamoyl, optionally substituted carbamoylcarbonyl, lower alkoxycarbonylcarbonyl, carboxycarbonyl, lower alkoxycarbonyl, optionally substituted heterocyclic carbonyl, lower alkylsulfonyl, optionally substituted arylsulfonyl, optionally substituted heteroarylsulfonyl, or optionally substituted lower alkylsulfonyl), oxo and halogen, a pharmaceutically acceptable salt or a solvate thereof.

(8) A compound according to the above (1), wherein R$^1$ is a group selected from the group consisting of:

[Formula 8]

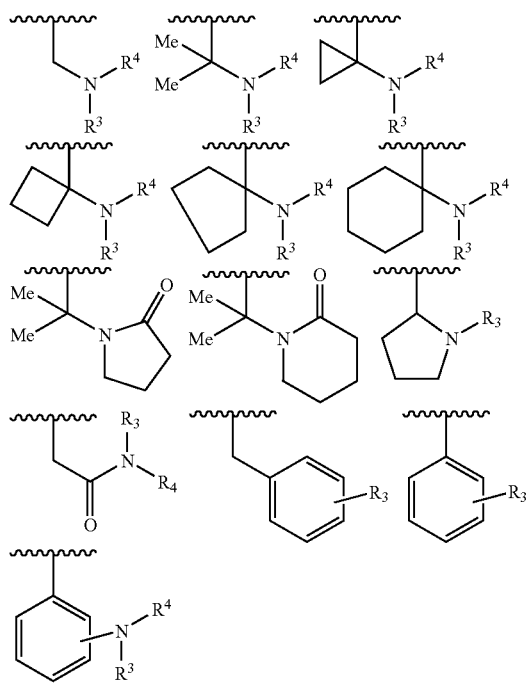

(wherein, R$^3$ and R$^4$ are the same meanings as above), a pharmaceutically acceptable salt or a solvate thereof.

(9) A compound according to the above (1), wherein Z$^1$ is a single bond or O; Z$^2$ is a single bond or lower alkylene; Z$^3$ is a single bond; Ar is optionally substituted phenyl; X is a group represented by (a); C ring is a group as recited in the above (5) or (6); and R$^1$ is a group as recited in the above (7) or (8), a pharmaceutically acceptable salt or a solvate thereof.

(10) A compound according to the above (4), wherein X is a group represented by (a); R$^1$ and R$^2$ form, together with an adjacent atom, an optionally substituted heterocyclic ring, a pharmaceutically acceptable salt or a solvate thereof.

(11) A compound according to the above (4) of the formula:

[Formula 9]

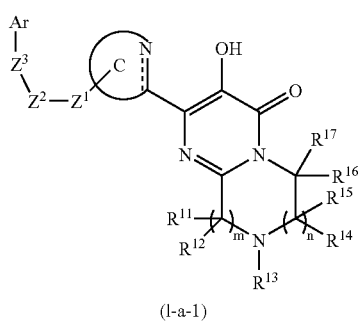

(I-a-1)

(wherein each symbol is the same meanings as above (1)), a pharmaceutically acceptable salt or a solvate thereof.

(12) A compound according to the above (1) of the formula:

[Formula 10]

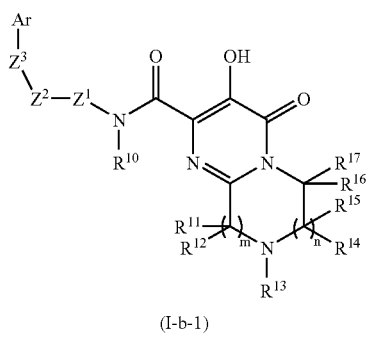

(I-b-1)

(wherein each symbol is the same meanings as above (1)), a pharmaceutically acceptable salt or a solvate thereof.

(13) A compound according to the above (11) or (12), wherein Z$^1$ is a single bond or O; Z$^2$ is a single bond or lower alkylene; Z$^3$ is a single bond; and Ar is optionally substituted phenyl, a pharmaceutically acceptable salt or a solvate thereof.

(14) A compound according to the above (11) or (12), wherein m is 1, and n is 0 or 1, a pharmaceutically acceptable salt or a solvate thereof.

(15) A compound according to the above (11) or (12), wherein R$^{11}$ and R$^{12}$ each is independently hydrogen or lower alkyl; R$^{14}$ and R$^{15}$ both are hydrogens, or together form "=O"; and R$^{16}$ and R$^{17}$ each is independently hydrogen or lower alkyl, a pharmaceutically acceptable salt or a solvate thereof.

(16) A compound according to the above (11) or (12), wherein m is 1, n is 0 or 1; R$^{11}$ and R$^{12}$ each is independently hydrogen or lower alkyl; R$^{14}$ and R$^{15}$ both are hydrogens, or together form "=O"; and R$^{16}$ and R$^{17}$ each is independently hydrogen or lower alkyl, a pharmaceutically acceptable salt or a solvate thereof.

(17) A compound according to the above (1) represented by the formula:

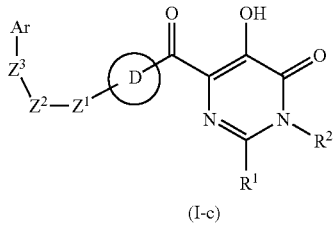

[Formula 11]

(I-c)

(wherein each symbol is the same meanings as above (1)), a pharmaceutically acceptable salt or a solvate thereof.

(18) A compound according to the above (1) represented by the formula:

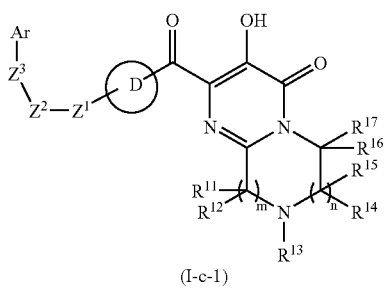

[Formula 12]

(I-c-1)

(wherein each symbol is the same meanings as above (1)), a pharmaceutically acceptable salt or a solvate thereof.

(19) A compound according to the above (17) or (18), wherein D ring is furan, a pharmaceutically acceptable salt or a solvate thereof.

(20) A pharmaceutical composition comprising a compound according to anyone of the above (1) to (19), a pharmaceutically acceptable salt or a solvate thereof.

(21) A pharmaceutical composition according to the above (20) which is an antiviral agent.

(22) A pharmaceutical composition according to the above (20) which is an HIV integrase agent.

EFFECT OF THE INVENTION

Compounds of the present invention have inhibitory activity against integrase, and/or have activity of inhibiting proliferation of viruses, especially HIV cells. Therefore, they are useful for prophylaxis and therapy of a variety of integrase-related diseases, and viral infectious diseases (e.g., AIDS).

BEST MODE FOR CARRYING OUT THE INVENTION

The terms used in the present specification are explained as follows. Each term by itself or as part of another has the following meaning.

The term "lower alkylene" means a C1-C6 straight or branched lower alkylene group, for example, methylene, ethylene, trimethylene, propylene, tetramethylene, ethylethyl-ene, pentamethylene or hexamethylene. Preferred is a C1-C4 straight lower alkylene group such as methylene, ethylene, trimethylene or tetramethylene. More preferred is methylene or ethylene.

The term "lower alkenylene" means a C2-C6 straight or branched lower alkenylene group, which is the above "lower alkylene" having one or more double bonds, for example, vinylene, propenylene or butenylene. Preferred is a C2-C3 straight lower alkenylene group such as vinylene or propenylene.

The term "alkyl" means a C1-C10 straight or branched alkyl group, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl or n-decyl. Preferred is a lower (C1-C6) alkyl group, and more preferred is a C1-C4 lower alkyl such as methyl, ethyl, n-propyl, isopropyl, n-butyl, isobutyl, sec-butyl, tert-butyl n-pentyl, isopentyl, neopentyl, tert-pentyl, n-hexyl or isohexyl.

The term "alkenyl" means a C2-C8 straight or branched alkenyl group which is the above "alkyl" having one or more double bonds, for example, vinyl, 1-propenyl, 2-propenyl, 1-butenyl, 2-butenyl, 3-butenyl, 1,3-butadienyl or 3-methyl-2-butenyl.

The term "cycloalkyl" means a C3-C10 cyclic saturated hydrocarbon group, for example, cyclopropyl, cyclobutyl, cyclopentyl, cyclohexyl, cycloheptyl, or cyclooctyl. Preferred is a C3-C6 cycloalkyl group.

The term "cycloalkyl lower alkyl" means the above "lower alkyl" substituted with the above "cycloalkyl", for example, cyclopropyl methyl, cyclobutyl methyl, or cyclopentyl methyl.

The term "cycloalkenyl" means a C3-C10 cyclic non-aromatic hydrocarbon group, for example, cyclopropenyl (e.g., 1-cyclopropenyl), cyclobutenyl (e.g., 1-cyclobutenyl), cyclopentenyl (e.g., 1-cyclopentene-1-yl, 2-cyclopentene-1-yl or 3-cyclopentene-1-yl), cyclohexenyl (e.g., 1-cyclohexene-1-yl, 2-cyclohexene-1-yl or 3-cyclohexene-1-yl), cycloheptenyl (e.g., 1-cycloheptenyl) or cyclooctenyl (e.g., 1-cyclooctenyl).

The term "aryl" means a monocyclic aromatic hydrocarbon group (e.g., phenyl) or a polycyclic aromatic hydrocarbon group (e.g., 1-naphthyl, 2-naphthyl, 1-antolyl, 2-antolyl, 9-antolyl, 1-phenantolyl, 2-phenantolyl, 3-phenantolyl, 4-phenantolyl or 9-phenantolyl). Preferred is phenyl or naphthyl (e.g., 1-naphthyl or 2-naphthyl).

The term "aryl carbonyl" means carbonyl to which the above "aryl" is bound, for example, phenylcarbonyl or 1-naphthylcarbonyl.

The term "aryloxy" means oxy to which the above "aryl" is bound, for example, phenyloxy or 1-naphthyloxy.

The term "arylsulfonyl" means sulfonyl to which the above "aryl" is bound, for example, phenylsulfonyl or 1-naphthylsulfonyl.

The term "aralkyl" means the above "alkyl" substituted with 1 to 3 above "aryl", for example, benzyl, diphenylmethyl, triphenylmethyl, phenethyl, 1-naphthylmethyl or 2-naphthylmethyl. Preferred is benzyl.

The term "aralkyloxy" means oxy to which the above "aralkyl" is bound, for example, benzyloxy or diphenylmethyloxy.

The term "heterocyclic group" means "heterocycle" or "heteroaryl".

The term "heterocycle" means anon-aromatic heterocyclic group (preferably 5 to 7-membered) which contains at least one of nitrogen atom, oxygen atom and/or sulfur atom, and which has a bonding position at any substitutable position, for example, 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperazinyl, 2-piperazinyl, 2-morpholinyl, 3-morpholinyl, morpholino or tetrahydropyranyl. Then, "a non-aromatic heterocyclic group" can be saturated or unsaturated insofar as it is non-aromatic.

The term "heteroaryl" means a monocyclic aromatic heterocyclic group and a condensed aromatic heterocyclic group.

A monocyclic aromatic heterocyclic group means a group, which is derived from a 5- to 8-membered aromatic ring which may contain 1 to 4 of oxygen atom, sulfur atom, and/or nitrogen atom and which may have a bonding position at any substitutable position.

A condensed aromatic heterocyclic group means a group, wherein a 5- to 8-membered aromatic ring which may contain 1 to 4 of oxygen atom, sulfur atom, and/or nitrogen atom is condensed with 1 to 4 of 5- to 8-membered aromatic carbon cycle or the other 5- to 8-membered aromatic heterocyclic ring and which may have a bonding position at the any substitutable position.

The term "heteroaryl" means the following groups, for example, furyl (e.g., 2-furyl or 3-furyl), thienyl (e.g., 2-thienyl or 3-thienyl), pyrrolyl (e.g., 1-pyrrolyl, 2-pyrrolyl or 3-pyrrolyl), imidazolyl (e.g., 1-imidazolyl, 2-imidazolyl or 4-imidazolyl), pyrazolyl (e.g., 1-pyrazolyl, 3-pyrazolyl or 4-pyrazolyl), triazolyl (e.g., 1,2,4-triazol-1-yl, 1,2,4-triazol-3-yl or 1,2,4-triazol-4-yl), tetrazolyl (e.g., 1-tetrazolyl, 2-tetrazolyl or 5-tetrazolyl), oxazolyl (e.g., 2-oxazolyl, 4-oxazolyl or 5-oxazolyl), isoxazolyl (e.g., 3-isoxazolyl, 4-isoxazolyl or 5-isoxazolyl), thiazolyl (e.g., 2-thiazolyl, 4-thiazolyl or 5-thiazolyl), thiadiazolyl, isothiazolyl (e.g., 3-isothiazolyl, 4-isothiazolyl or 5-isothiazolyl), pyridyl (e.g., 2-pyridyl, 3-pyridyl or 4-pyridyl), pyridazinyl (e.g., 3-pyridazinyl or 4-pyridazinyl), pyrimidinyl (e.g., 2-pyrimidinyl, 4-pyrimidinyl or 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl or 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g., 1-benzoimidazolyl, 2-benzoimidazolyl, 4-benzoimidazolyl or 5-benzoimidazolyl), dibenzofuryl, benzooxazolyl, quinoxalyl (e.g. 2-quinoxalinyl, 5-quinoxalinyl or 6-quinoxalinyl), cinnolinyl (e.g., 3-cinnolinyl, 4-cinnolinyl, 5-cinnolinyl, 6-cinnolinyl, 7-cinnolinyl or 8-cinnolinyl), quinazolyl (e.g., 2-quinazolinyl, 4-quinazolinyl, 5-quinazolinyl, 6-quinazolinyl, 7-quinazolinyl or 8-quinazolinyl), quinolyl (e.g., 2-quinolyl, 3-quinolyl, 4-quinolyl, 5-quinolyl, 6-quinolyl, 7-quinolyl or 8-quinolyl), phthalazinyl (e.g., 1-phthalazinyl, 5-phthalazinyl or 6-phthalazinyl), isoquinolyl (e.g., 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g., 2-pteridinyl, 4-pteridinyl, 6-pteridinyl or 7-pteridinyl), carbazolyl, phenantridinyl, acridinyl (e.g., 1-acridinyl, 2-acridinyl, 3-acridinyl, 4-acridinyl or 9-acridinyl), indolyl (e.g., 1-indolyl, 2-indolyl, 3-indolyl, 4-indolyl, 5-indolyl, 6-indolyl or 7-indolyl), isoindolyl, phenazinyl (e.g., 1-phenazinyl or 2-phenazinyl) or phenothiazinyl (e.g., 1-phenothiazinyl, 2-phenothiazinyl, 3-phenothiazinyl or 4-phenothiazinyl).

The term "heteroarylcarbonyl" means carbonyl to which the above "heteroaryl" is bound.

The term "heteroarylsulfonyl" means sulfonyl to which the above "heteroaryl" is bound.

The term "heterocyclic ring" means heterocyclic ring that forms the above heterocyclic group.

The term "heterocyclic carbonyl" means carbonyl to which the above heterocyclic ring is bound.

Alkyl moiety of "alkoxy" is the same meaning as the above "alkyl". "Alkoxy" is, for example, methoxy, ethoxy, n-propoxy, isopropoxy, n-butoxy, isobutoxy, or tert-butoxy.

The term "alkoxycarbonyl" means a carbonyl substituted with the above "alkoxy", for example, methoxycarbonyl, ethoxycarbonyl, n-propoxycarbonyl, isopropoxycarbonyl, n-butoxycarbonyl, isobutoxycarbonyl, or tert-butoxycarbonyl. Preferable is C1-C6 lower alkoxy.

The term "lower alkoxycarbonyl" means carbonyl to which the above "lower alkoxy" is bound.

The term "alkoxyalkyl" means the above "alkyl" substituted with the above "alkoxy", for example, methoxymethyl, ethoxymethyl, n-propoxymethyl, isopropoxymethyl, n-butoxymethyl, isobutoxymethyl, tert-butoxymethyl, methoxyethyl, ethoxyethyl, n-propoxyethyl, isopropoxyethyl, n-butoxyethyl, isobutoxyethyl or tert-butoxyethyl.

The term "lower alkylsulfonyl" means a sulfonyl substituted with the above "lower alkyl", for example, methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl, n-heptylsulfonyl, n-octylsulfonyl, n-nonylsulfonyl or n-decylsulfonyl. Especially preferable is methylsulfonyl.

The substituent of "optionally substituted amino", "optionally substituted carbamoyl" and "optionally substituted carbamoylcarbonyl" is optionally substituted alkyl (e.g., methyl, ethyl, isopropyl, benzyl, carbamoylalkyl (e.g., carbamoylmethyl), mono or di alkylcarbamoyl alkyl (e.g., dimethylcarbamoylethyl), hydroxyalkyl, heterocycle alkyl (e.g., morpholinoethyl, tetrahydropyranylethyl), alkoxycarbonyl alkyl (e.g., ethoxycarbonyl methyl, ethoxycarbonyl ethyl), mono or di alkylamino alkyl (e.g., dimethylaminoethyl) and the like), alkoxyalkyl (e.g., methoxyethyl, ethoxymethyl, ethoxyethyl or isopropoxyethyl), acyl (e.g., formyl, optionally substituted alkyl carbonyl (e.g., acetyl, propionyl, butyryl, isobutyryl, valeryl, isovaleryl, pivaloyl, hexanoyl, octanoyl, methoxyethyl carbonyl, 2,2,2-trifluoroethyl carbonyl, ethoxycarbonylmethyl carbonyl, alkoxyalkylcarbonyl (e.g., methoxyethyl carbonyl), alkylcarbamoylalkylcarbonyl (e.g., methylcarbamoylethylcarbonyl), alkoxycarbonyl acetyl and the like), optionally substituted arylcarbonyl (e.g., benzoyl, toluoyl), optionally substituted aralkyl (e.g., benzyl, 4-fluorobenzyl), hydroxy, optionally substituted alkyl sulfonyl (e.g., methane sulfonyl, ethane sulfonyl, isopropyl sulfonyl, 2,2,2-trifluoroethane sulfonyl, benzyl sulfonyl, methoxyethyl sulfonyl), arylsulfonyl optionally substituted with alkyl or halogen (e.g., benzenesulfonyl, toluenesulfonyl, 4-fluorobenzenesulfonyl), cycloalkyl (e.g., cyclopropyl), aryl optionally substituted with alkyl (e.g., phenyl, trithyl), alkylamino sulfonyl (e.g., methylamino sulfonyl, dimethylaminisulfonyl), alkylaminocarbonyl (e.g., dimethylaminocarbonyl), alkoxycarbonyl (e.g., ethoxycarbonyl), cycloalkylcarbonyl (e.g., cyclopropylcarbonyl, cyclohexylcarbonyl), optionally substituted sulfamoyl (e.g., sulfamoyl, methylsulfamoyl, dimethylsulfamoyl), alkyl carbonylamino (e.g., methyl carbonylamino), heterocycle (e.g., morpholino, tetrahydropyranyl), optionally substituted amino (e.g., mono or di alkylamino (e.g., dimethylamino), formylamino) and the like. Especially preferable is methyl. The above substituent may be mono-substituted or di-substituted.

An amino group in "optionally substituted amino", "optionally substituted carbamoyl" or "optionally substituted carbamoylcarbonyl" may form a nitrogen-containing heterocycle (preferably 5- to 7-membered and preferably saturated) which may contain in the cycle a sulfur atom and/or oxygen atom, as well as a nitrogen atom to which two substituents of the amino group are adjacent, and the cycle is optionally substituted with oxo or hydroxy. The sulfur atom forming the cycle is optionally substituted with oxo. For example, 5- or 6-membered rings such as piperazinyl, piperidino, morpholino, pyrrolidino, thiazinane-2-yl, 2-oxopiperidino, 2-oxopyrrolidino, 1,1-dioxide-1,2-thiazinane-2-yl, 4-hydroxymorpholino and the like are preferred.

The term "alkylthio" means a sulfur atom substituted with the above "alkyl", for example, methylthio, ethylthio, n-propylthio, isopropylthio, n-butylthio, isobutylthio, sec-butylthio, tert-butylthio, n-pentylthio, isopentylthio, neopentylthio, tert-pentylthio, n-hexylthio, isohexylthio, n-heptylthio, n-octylthio, n-nonylthio or n-decylthio. A C1-C6 alkylthio is preferable.

The term "haloalkyl" means the above "alkyl" substituted with one or more halogen. Especially preferable is a C1-C3 halogenated alkyl, for example, trifluoromethyl, chloromethyl, dichloromethyl, 1,1-dichloroethyl or 2,2,2-trichloroethyl.

The term "haloalkoxy" means oxygen atom substituted with the above "haloalkyl", for example, trifluoromethoxy, chloromethoxy, dichloromethoxy, 1,1-dichloroethoxy or 2,2,2-trichloroethoxy.

The term "acyl" means a carbonyl substituted with the above "alkyl" and a carbonyl substituted with the above "aryl", for example, acetyl, propionyl, butyryl, isobutyryl, valeryl, isovaleryl, pivaloyl, hexanoyl, octanoyl, lauroyl or benzoyl.

The term "alkyl carbonyl" means a carbonyl substituted with the above "alkyl", for example, acetyl, propionyl, butyryl, isobutyryl, valeryl, isovaleryl, pivaloyl, hexanoyl, octanoyl or lauroyl.

The term "alkylcarbonyloxy" means oxygen atom substituted with the above "alkylcarbonyl" substituted with oxygen atom, for example, acetyloxy, propionyloxy, butyryloxy, isobutyryloxy, valeryloxy, isovaleryloxy, pivaloyloxy, hexanoyloxy, octanoyloxy or lauroyloxy.

The term "heterocyclic lower alkyl" means "lower alkyl" substituted with the above "heterocyclic group", preferably heterocycle lower alkyl. The heterocycle lower alkyl is more preferably, isopropyl substituted with 5- to 7-membered N-atom containing ring.

The term "heteroaralkyl" means the above "alkyl" substituted with 1 to 3 above "heteroaryl". Preferred is heteroaralkyl having 1 to 4 carbon atom(s) in the alkyl moiety. Especially preferable is heteroalkyl having 1 or 2 carbon atom(s) in the alkyl moiety, for example, furylmethyl, thienylmethyl, pyrrolylmethyl, imidazolylmethyl, pyrazolylmethyl, triazolylmethyl, tetrazolylmethyl, oxazolylmethyl, isoxazolylmethyl, thiazolylmethyl, thiadiazolylmethyl, isothiazolylmethyl, pyridylmethyl, pyridazinylmethyl, pyrimidinylmethyl, furazanylmethyl, pyrazinylmethyl, oxadiazolylmethyl, benzofurylmethyl, benzothienylmethyl, benzimidazolylmethyl, dibenzofurylmethyl, benzooxazolylmethyl, quinoxalylmethyl, cinnolinylmethyl, quinazolylmethyl, quinolylmethyl, phthalazinylmethyl, isoquinolylmethyl, puriylmethyl, pteridinylmethyl, carbazolylmethyl, phenantridinylmethyl, acridinylmethyl, indolylmethyl, isoindolylmethyl, phanazinylmethyl, phenothiazinylmethyl, furylethyl, thienylethyl, pyrrolylethyl, imidazolylethyl, pyrazolylethyl, triazolylethyl, tetrazolylethyl, oxazolylethyl, isoxazolylethyl, thiazolylethyl, thiadiazolylethyl, isothiazolylethyl, pyridylethyl, pyridazinylethyl, pyrimidinylethyl, furazanylethyl, pyrazinylethyl, oxadiazolylethyl, benzo furylethyl, benzo thienylethyl, benzimidazolyl ethyl, dibenzo furylethyl, benzo oxazolylethyl, quinoxalylethyl, cinnolinylethyl, quinazolylethyl, quinolylethyl, phthalazinylethyl, isoquinolylethyl, puriylethyl, pteridinylethyl, carbazolylethyl, phenantridinylethyl, acridinylethyl, indolylethyl, isoindolylethyl, phanazinylethyl or phenothiazinylethyl.

When "substituted lower alkyl", "optionally substituted lower alkyl", "optionally substituted cycloalkyl", "optionally substituted cycloalkyl lower alkyl", "optionally substituted lower alkylcarbonyl", "optionally substituted aryl", "optionally substituted aralkyl", "optionally substituted arylcarbonyl", "optionally substituted heterocyclic group", "optionally substituted heterocyclic ring", "optionally substituted heterocyclic lower alkyl", "optionally substituted heterocyclic carbonyl", "optionally substituted heteroaryl", "optionally substituted heterocycle", "optionally substituted heteroaralkyl", "optionally substituted aryloxy", "optionally substituted heteroaryloxy", "optionally substituted arylthio", "optionally substituted heteroarylthio", "optionally substituted aralkyloxy", "optionally substituted arylsulfonyl", "optionally substituted heteroarylsulfonyl", "optionally substituted hydroxy", "optionally substituted thiol", "optionally substituted sulfonyl", "optionally substituted lower alkylsulfonyl", "optionally substituted heteroarylcarbonyl", "optionally substituted phenyl" and the like have a substituent, they are optionally substituted at any position with an identical or different one to four group(s) selected from the substituent group B.

Examples of the substitution group B include hydroxy, carboxy, halogen (e.g., F, Cl, Br or I), halo alkyl (e.g., $CF_3$, $CH_2CF_3$ and $CH_2CCl_3$), alkyl (e.g., methyl, ethyl, isopropyl and tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy and butoxy), alkenyloxy (e.g., vinyloxy and allyloxy), alkoxycarbonyl (e.g., methoxycarbonyl, ethoxycarbonyl and tert-butoxycarbonyl), nitro, nitroso, optionally substituted amino (e.g., alkylamino (e.g., methylamino, ethylamino and dimethylamino), acylamino (e.g., acetylamino and benzoylamino), aralkylamino (e.g., benzylamino and tritylamino) and hydroxyamino), azide, aryl (e.g., phenyl), aralkyl (e.g., benzyl), cyano, isocyano, isocyanato, thiocyanato, isothiocyanato, mercapto, alkylthio (e.g., methylthio), alkylsulfonyl (e.g., methanesulfonyl and ethanesulfonyl), optionally substituted carbamoyl (e.g., alkylcarbamoyl (e.g., methylcarbamoyl, ethylcarbamoyl and dimethylcarbamoyl), and the like), sulfamoyl, acyl (e.g., formyl and acetyl), formyloxy, haloformyl, oxalo, thioformyl, thiocarboxy, dithiocarboxy, thiocarbamoyl, sulfino, sulfo, sulfoamino, hydrazino, azide, ureide, amidino, guanidine, phthalimide, oxo, and heterocyclic ring.

More Preferred Embodiment

In Compound (I), X represents the following group of (a), (b) or (c). Preferably, it is a group (a) or (b).

[Formula 13]

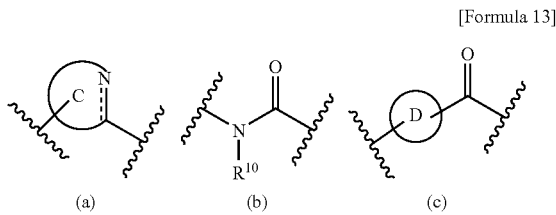

In the group (a), C ring means nitrogen-containing aromatic heterocyclic ring in which at least one atom among the atoms adjacent to the atom bound to the pyrimidine is an unsubstituted nitrogen atom. The broken line shows presence or absence of a bond. The curve part means an atom(s) and a bond(s) forming the C ring, and may be selected so that C ring has aromaticity. Preferably, in the C ring, an atom bound to the pyrimidine ring is a carbon atom, and the carbon atom is bound to one of the adjacent atoms via a double bond, and bound to the other of the adjacent atoms via a single bond. C ring is preferably a 5 to 8-membered ring, and more preferably a 5- or 6-membered ring, or may be a condensed ring with other ring (e.g., carbon ring, heterocyclic ring). C ring may have one to four, preferably one to three identical or different hetero atom(s) selected from the group consisting of O, S and N atoms, as well as one N atom. Preferably, C ring may have one or two N atom(s), or have one or two N atom(s) and one O or S atom.

Examples in which C ring is a monocycle include pyrol-2-yl, imidazole-2-yl, imidazole-4-yl, pyrazole-3-yl, triazole-3-yl, tetrazole-5-yl, oxazole-2-yl, oxazole-4-yl, isoxazole-3-yl, thiazole-2-yl, thiazole-4-yl, 1,3,4-thiadiazole-2-yl, 1,2,4-thiadiazole-5-yl, 1,2,4-thiadiazole-3-yl, 1,3,4-oxadiazole-2-yl, 1,2,4-oxadiazole-5-yl, 1,2,4-oxadiazole-3-yl, isothiazole-3-yl, pyridine-2-yl, pyridadine-3-yl, pyradine-2-yl, pyrimidine-2-yl, pyrimidine-4-yl, and furazan-3-yl. More preferably, imidazole-2-yl, imidazole-4-yl, pyrazole-3-yl, triazole-3-yl, tetrazole-5-yl, oxazole-2-yl, oxazole-4-yl, isoxazole-3-yl, thiazole-2-yl, thiazole-4-yl, 1,3,4-thiadiazole-2-yl, 1,2,4-thiadiazole-5-yl, 1,2,4-thiadiazole-3-yl, 1,3,4-oxadiazole-2-yl, 1,2,4-oxadiazole-5-yl, 1,2,4-oxadiazole-3-yl, isothiazole-3-yl, pyridine-2-yl, pyridadine-3-yl, pyradine-2-yl, pyrimidine-2-yl, pyrimidine-4-yl, furazan-3-yl and the like are exemplified.

Examples in which C ring is a condensed ring include heteroaryls in which one to four 5- to 8-membered aromatic carbon ring (5 to 8-membered aromatic carbon ring) and/or other 5- to 8-membered aromatic heterocyclic ring (5- to 8-membered aromatic heterocyclic ring which may contain one to four O atom, S atom, and/or N atom in the ring) is/are condensed to the above monocycle. As the condensing aromatic ring, 5-membered or 6-membered ring is preferred. Examples include benzimidazole-2-yl, benzoxazole-2-yl, quinoxaline-2-yl, cinnoline-3-yl, quinazoline-2-yl, quinazoline-4-yl, quinoline-2-yl, phthalazine-1-yl, isoquinoline-1-yl, isoquinoline-3-yl, purine-2-yl, purine-6-yl, purine-8-yl, pteridine-2-yl, pteridine-4-yl, pteridine-6-yl, pteridine-7-yl, carbazole-1-yl, phenanthridine-6-yl, indole-2-yl, and isoindole-1-yl.

Preferably, C ring is a ring shown below.

[Formula 14]

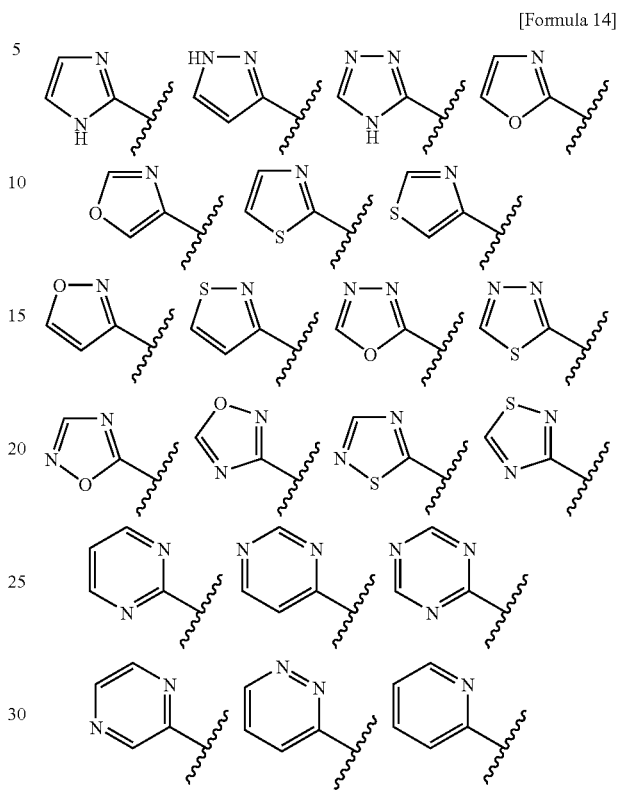

More preferably, C ring is a ring shown below.

[Formula 15]

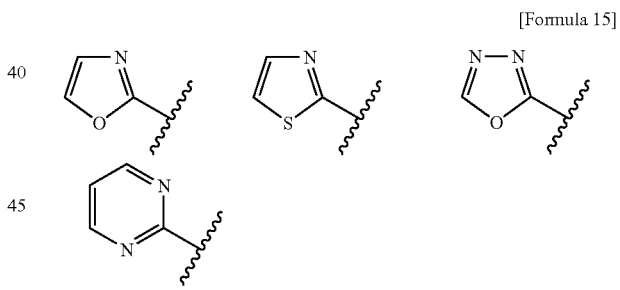

Especially preferable is oxazole or thiazole.

In the group where X is (b), $R^{10}$ is preferably hydrogen or C1 to C4 alkyl (e.g., methyl), especially hydrogen.

In the group where X is (c), D ring is preferably heteroaryl, more preferably 5- or 6-membered ring having one or two, preferably one O, S and/or N atom, and particularly preferably furan.

$Z^1$ and $Z^3$ each is independently a single bond, O, S, S(=O) or $SO_2$. $Z^1$ is preferably a single bond or O. $Z^3$ is preferably a single bond.

$Z^2$ is a single bond, lower alkylene, or lower alkenylene, and preferably a single bond, methylene or ethylene.

Ar is optionally substituted aryl or optionally substituted heteroaryl, preferably optionally substituted aryl, more preferably aryl optionally substituted with halogen.

In —$Z^1$—$Z^2$—$Z^3$—Ar, preferably, $Z^1$ is a single bond or O; $Z^2$ is a single bond, methylene or ethylene; $Z^3$ is a single bond; and Ar is optionally substituted aryl (particularly preferred is phenyl optionally substituted halogen). More preferably, —$Z^1$—$Z^2$—$Z^3$—Ar is 4-fluorobenzyl or 4-fluorophenyloxy.

$R^1$ is lower alkyl, substituted lower alkyl, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl, preferably, substituted lower alkyl, optionally substituted cycloalkyl, optionally substituted aralkyl, optionally substituted heterocyclic group or optionally substituted heterocyclic lower alkyl. The heterocyclic lower alkyl involves heterocycle lower alkyl and heteroaralkyl.

A lower alkyl in substituted lower alkyl is preferably methyl, isopropyl and the like.

A substituent in each of "optionally substituted" or "substituted" of $R^1$ may be selected from the above substituent group B, however, it is preferably selected from the group consisting of —$NR^3R^4$, —C(=O)$R^3$ and —C(=O)$NR^3R^4$, or from oxo, halogen, or the later-described $R^8$, $R^9$ and the like.

$R^3$ and $R^4$ each is independently hydrogen, hydroxy, halogen, alkoxy, optionally substituted aryloxy, optionally substituted aralkyloxy, optionally substituted amino, optionally substituted alkyl, optionally substituted cycloalkyl, optionally substituted aryl, optionally substituted heterocyclic group, optionally substituted aralkyl, optionally substituted heteroaralkyl, optionally substituted lower alkylcarbonyl, optionally substituted arylcarbonyl, option ally substituted carbamoyl, optionally substituted carbamoylcarbonyl, lower alkoxycarbonylcarbonyl, carboxycarbonyl, lower alkoxycarbonyl, optionally substituted heterocyclic carbonyl, lower alkylsulfonyl, optionally substituted arylsulfonyl or optionally substituted heteroarylsulfonyl.

More preferred combination of $R^3$ and $R^4$ is ($R^3$,$R^4$)=(H, H), (H, Me), (H, COMe), (H, COCONMe$_2$), (H, COCONHMe), (H, CO Ph), (H, CO-2-pyridyl), (Me, Me), (Me, COMe), (Me, COCONMe$_2$), (Me, COCONHMe), (Me, COPh), (Me, CO-2-pyridyl), (H, COCOOH), (H, —SO$_2$— (optionally substituted methyl)), (H, COCH$_2$OMe), (H, COCH$_2$Cl), (H, CO-cyclopropyl), (H, optionally substituted carbamoyl), (H, alkyl carbonyl), (H, optionally substituted arylcarbonyl), (H, optionally substituted heteroarylcarbonyl) or the like. A substituent for optional substitution is preferably halogen, lower alkoxy, hydroxy, carboxy or the like.

More preferably, $R^1$ is either one of the groups shown below.

[Formula 16]

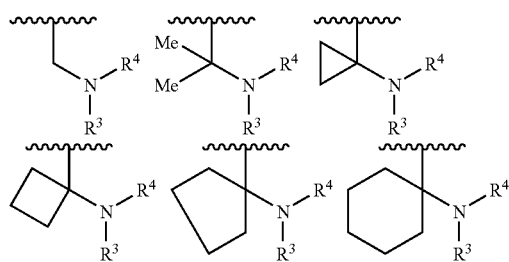

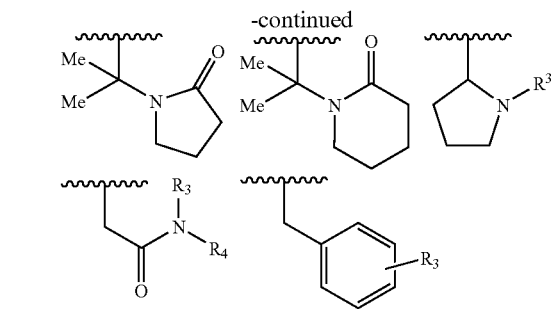

(wherein $R^3$ and $R^4$ are the same meanings as above.)

In the above groups, when $R^3$ bonds to a benzene ring or heterocyclic ring, preferred embodiment of $R^3$ includes halogen, lower alkylsulfonyl, lower alkylcarbonyl, optionally substituted heterocyclic group (preferably, optionally substituted heterocycle), optionally substituted lower alkylcarbonylamino, and optionally substituted lower alkylsulfonylamino.

Alternatively, $R^1$ may be either one of the groups shown below.

[Formula 17]

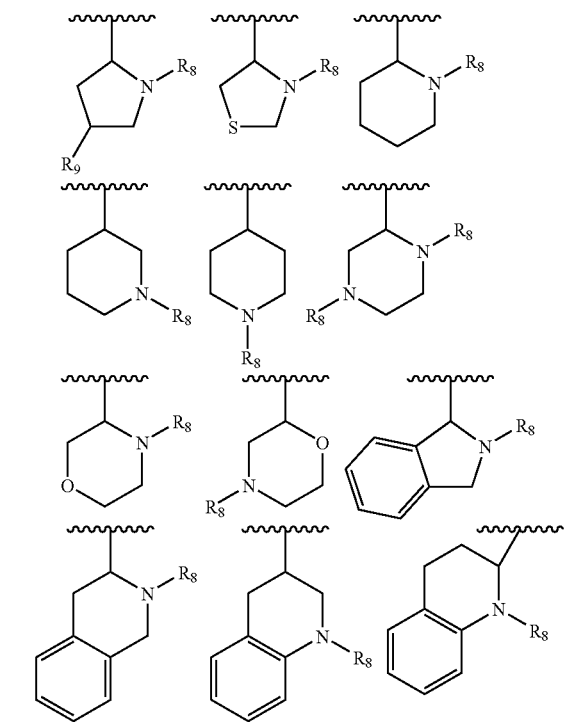

(wherein $R^8$ and $R^9$ each is independently 1) hydrogen, 2) optionally substituted lower alkyl (substituent: OH, lower alkoxy, halogenated lower alkoxy, lower alkanoyl, lower alkoxycarbonyl, lower alkylthio, amino optionally substituted with mono or di lower alkyl, carbamoyl optionally substituted with mono or di lower alkyl), 3) lower alkylcarbonyl, 4) lower alkyloxycarbonyl, 5) carbamoyl optionally substituted with mono or di lower alkyl, 6) lower alkylcarbonyl substituted with amino that is optionally substituted with mono or di lower alkyl, 7) lower alkylsulfonyl and so on).

More preferably, $R^1$ is 1) optionally substituted benzyl (example of substituent: halogen), 2) optionally substituted N-containing aliphatic 5 to 7-membered ring (example of substituent: optionally substituted lower alkylcarbonyl, optionally substituted lower alkylsulfonyl), 3) lower alkyl substituted with optionally substituted amino (example of substituent on amino: lower alkyl, optionally substituted lower alkylcarbonyl (substituent: lower alkoxy, halogen, oxo, amino, lower alkylamino), cycloalkylcarbonyl, carboxycarbonyl, optionally substituted lower alkylsulfonyl (substituent: lower alkoxy, halogen, oxo, amino, lower alkylamino), heterocyclic carbonyl)), 4) optionally substituted phenyl (example of substituent: optionally substituted heterocyclic ring, optionally substituted lower alkylcarbonylamino, optionally substituted lower alkylsulfonylamino) or the like.

$R^2$ is hydrogen or optionally substituted lower alkyl, preferably hydrogen or lower alkyl (e.g., methyl).

In another embodiment, $R^1$ and $R^2$, together with an adjacent atom, form an optionally substituted heterocyclic ring. Preferably, such heterocyclic ring is heterocycle, and contains in the ring at least one N atom. More preferably, it contains one N atom in the ring, and additionally contains other hetero atom selected from the group consisting of O, S and N, and preferably contains one N atom. As the substituent, the groups shown in $R^{11}$ to $R^{17}$ recited below are exemplified.

When $R^1$ and $R^2$ form, together with an adjacent atom, an optionally substituted heterocyclic ring, they preferably form heterocyclic ring shown by (d) below.

[Formula 18]

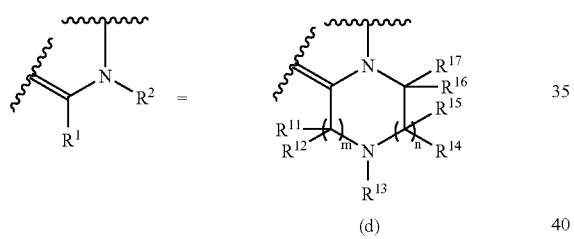

(d)

(wherein, $R^{11}$, $R^{12}$, $R^{14}$, $R^{15}$, $R^{16}$, and $R^{17}$ each is independently hydrogen, optionally substituted lower alkyl, optionally substituted aryl, optionally substituted heteroaryl, optionally substituted amino, optionally substituted hydroxy, optionally substituted thiol, optionally substituted sulfonyl, optionally substituted aminosulfonyl, or optionally substituted carbamoyl, or $R^{11}$ and $R^{12}$, $R^{14}$ and $R^{15}$, and $R^{16}$ and $R^{17}$ may respectively form "=O".

$R^{13}$ is hydrogen, optionally substituted lower alkyl, optionally substituted lower alkylcarbonyl, optionally substituted lower alkylsulfonyl, optionally substituted carbamoyl, optionally substituted arylcarbonyl or optionally substituted heteroarylcarbonyl;

m is 0, 1, 2 or 3; n is 0, 1, 2 or 3, provided that 1=m+n=3).

Preferably, m is 1 or 2 and n is 0 or 1, and more preferably m is 1 and n is 0 or 1, and particularly preferably m is 1 and n is 0.

Preferably, $R^{11}$ and $R^{12}$ both are lower alkyls (e.g., methyl).

Preferably, $R^{14}$ and $R^{15}$ both are hydrogens or together form "=O".

($R^{16}$, $R^{17}$) is preferably (H, H), (H, aryl), (H, lower alkyl) or (lower alkyl, lower alkyl).

$R^{13}$ is preferably hydrogen, lower alkyl, optionally substituted lower alkylcarbonyl (example of substituent: oxo, amino, mono- or di-lower alkylamino), lower alkylsulfonyl, optionally substituted carbamoyl (example of substituent: lower alkyl), optionally substituted arylcarbonyl, optionally substituted aralkyl, optionally substituted heteroaralkyl or optionally substituted heteroarylcarbonyl. As a substituent in optionally substituted arylcarbonyl, optionally substituted aralkyl, optionally substituted heteroaralkyl or optionally substituted heteroarylcarbonyl, hydroxy, amino, mono- or di-lower alkylamino, lower alkylcarbonylamino, lower alkoxy, and halogen are exemplified.

The followings are concrete examples of heterocyclic ring shown by (d).

[Formula 63]

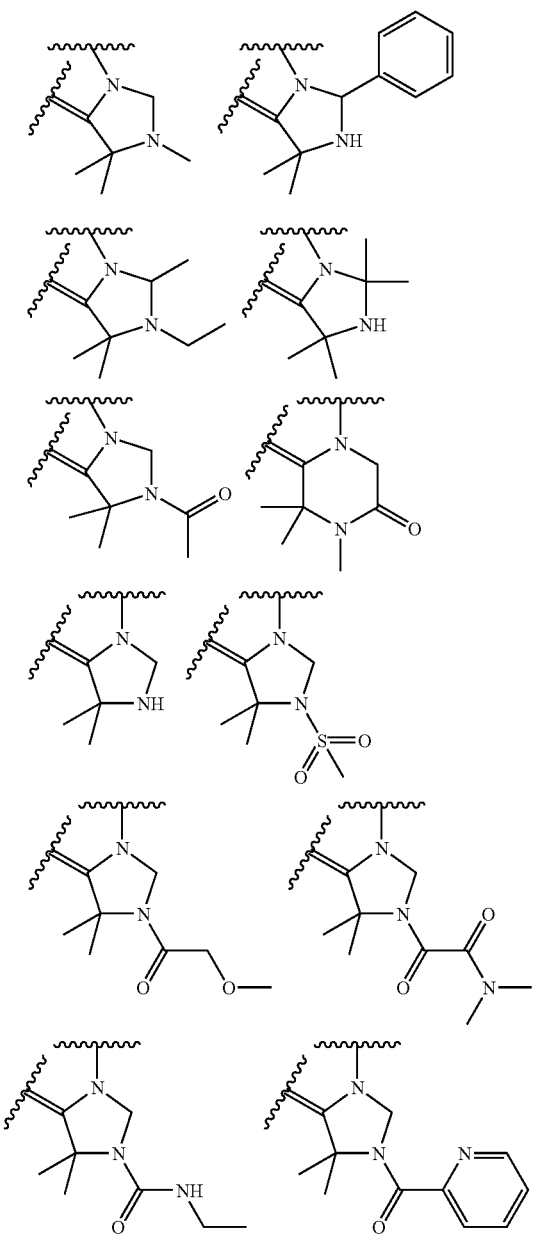

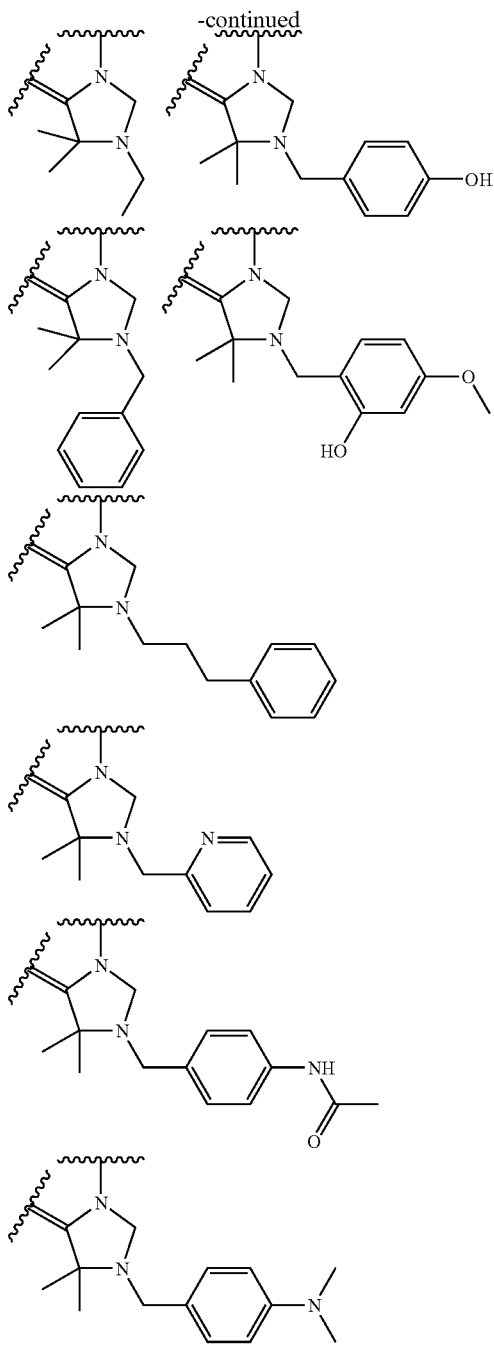

More preferably, Compound (I) includes the following forms.

(1) $Z^1$ is a single bond or O; $Z^2$ is a single bond, methylene or ethylene; $Z^3$ is a single bond; Ar is optionally substituted phenyl.

(2) C ring is group recited in the above (5) or (6) (Formula 5 or 6); and $R^1$ is a group recited in the above (7) or (8) (e.g., Formula 8). More preferably, C ring is a group recited in the above (6); and $R^1$ is a group recited in the above (8).

(3) $R^2$ is hydrogen atom or lower alkyl, more preferably methyl.

(4) All of the above (1) to (3) are satisfied.

(5) —$Z^1$—$Z^2$—$Z^3$—Ar is optionally substituted benzyl (e.g., 4-fluorobenzyl) or optionally substituted benzyloxy (e.g., 4-fluorophenyloxy); X is a group shown by (a) and C ring is oxazole-2-yl, thiazole-2-yl, or 1,3,4-oxadiazole-2-yl; $R^2$ is hydrogen or methyl; and $R^1$ is optionally substituted aralkyl, optionally substituted N-containing aliphatic 5 to 7-membered, or lower alkyl substituted with optionally substituted amino. In this case, more preferably, for example $R^1$ is 1) optionally substituted benzyl (example of substituent: halogen), 2) optionally substituted N-containing aliphatic 5- to 7-membered ring (example of substituent: optionally substituted lower alkylcarbonyl, optionally substituted lower alkylsulfonyl), 3) lower alkyl substituted with optionally substituted amino (example of substituent on amino: lower alkyl, optionally substituted lower alkylcarbonyl (substituent: lower alkoxy, halogen, oxo, amino, lower alkylamino), cycloalkylcarbonyl, carboxycarbonyl, optionally substituted lower alkylsulfonyl (substituent: lower alkoxy, halogen, oxo, amino, lower alkylamino), heterocyclic carbonyl)), or 4) optionally substituted phenyl (example of substituent: optionally substituted heterocyclic ring, optionally substituted lower alkylcarbonylamino, optionally substituted lower alkylsulfonylamino).

(6) —$Z^1$—$Z^2$—$Z^3$—Ar is optionally substituted benzyl (e.g., 4-fluorobenzyl) or optionally substituted benzyloxy (e.g., 4-fluorophenyloxy); X is a group shown by (a), C ring is oxazole-2-yl, thiazole-2-yl, or 1,3,4-oxadiazole-2-yl; and $R^1$ and $R^2$ together form a heterocyclic ring shown by (d).

(7) —$Z^1$—$Z^2$—$Z^3$—Ar is optionally substituted benzyl (e.g., 4-fluorobenzyl) or optionally substituted benzyloxy (e.g., 4-fluorophenyloxy); X is a group shown by (b); $R^1$ and $R^2$ together form a heterocyclic ring shown by (d).

(8) —$Z^1$—$Z^2$—$Z^3$—Ar is optionally substituted benzyl (e.g., 4-fluorobenzyl) or optionally substituted benzyloxy (e.g., 4-fluorophenyloxy); X is a group shown by (c); $R^2$ is hydrogen or methyl; and $R^1$ is optionally substituted aralkyl, optionally substituted N-containing aliphatic 5- to 7-membered, or lower alkyl substituted with optionally substituted amino.

(9) —$Z^1$—$Z^2$—$Z^3$—Ar is optionally substituted benzyl (e.g., 4-fluorobenzyl) or optionally substituted benzyloxy (e.g., 4-fluorophenyloxy); X is a group shown by (c); $R^1$ and $R^2$ together form a heterocyclic ring shown by (d).

Compound (I) has significantly improved pharmacological activity compared with a resembling compound described in WO 03/16275, for example, as a result of introduction of a relatively bulky group as a substituent particularly for $R^1$ moiety. In another form, $R^1$ and $R^2$ moieties form, together with an adjacent atom, an optionally substituted heterocyclic ring, so that the pharmacological activity is significantly improved. Compound (I) shows inhibitory activity against integrase and/or inhibitory activity against proliferation of HIV cells.

The present invention also provides a pharmaceutically acceptable salt of Compound (I) and solvates thereof. All of the theoretical possible tautomers and geometrical isomers of a compound of the present invention are also within the scope of the present invention.

Pharmaceutically acceptable salts of a compound of the present invention include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine, meglumine, diethanolamine or ethylenediamine salts; aralkyl amine salts such as N,N-dibenzylethylenediamine or benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid salts include, for example, inorganic acid salts such as hydrochloride, sulfates salts, nitrate salts, phosphates salts, carbonates salts, hydrogencarbonates or perchlorate; organic acid salts such as acetates, propionates, lactates, maleates, fumarates, tararic acid salts, malates, citrates salts, or ascorbates; sulfonates such as methanesulfonates, isethionates, benzenesulfonates, or p-toluenesulfonates; and acidic amino acid salts such as aspartates or glutamates.

As a solvate of compound of the present invention, alcoholate, hydrate and the like are exemplified.

General process for producing compounds of the present invention will be exemplified below.

(1) In the case where X is a group shown by (a)

(Process A)

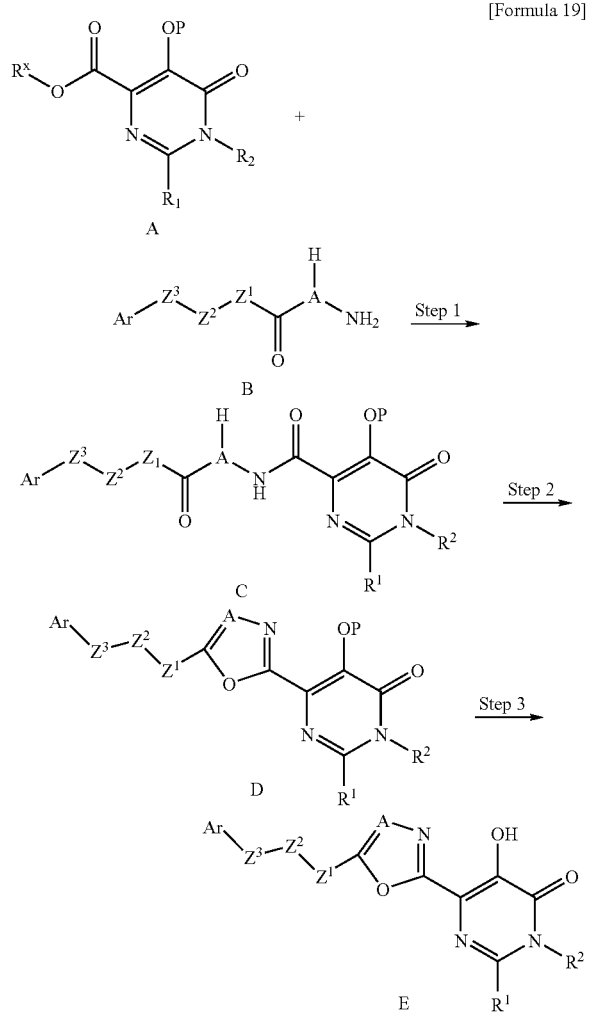

[Formula 19]

(wherein, P is hydrogen atom or hydroxy protecting group; A is CH or N; $R^x$ is lower alkyl (e.g., methyl, ethyl); other symbols are the same meanings as above.)

(Step 1)

This step is to produce Compound C by condensation between Compound A and Compound B. Namely, it is amidation of carboxylic derivative described, for example, in Advanced Organic Chemistry. $3^{Rd}$ ed. John Wiley & Sons, 1985, p 370-376.

Compound A may be directly caused to react, or caused to react after conversion to a corresponding acid chloride or active ester. Preferably, Compound A is converted into a corresponding carboxylic acid before it is caused to react in the presence of Compound B and a condensing agent in an appropriate solvent.

As a condensing agent, dicyclohexylcarbodiimide or 1-ethyl-3-(3-dimethylaminopropyl)carbodiimide hydrochloride can be used. If necessary, another reagent such as 1-hydroxybenzotriazole or N-hydroxysuccinimide or base such as triethylamine, N-methylmorpholine or pyridine may be added.

The reaction temperature is 0 to 150° C., preferably from room temperature to 70° C.

As a reaction solvent, a variety of aprotic solvents may be used, with tetrahydrofuran, 1,4-dioxane, dimethylformaide, methylene chloride, chloroform and the like being preferred.

Compound A may be a compound described in WO 03/035077, or may be synthesized according to a method described in that patent document or J. Heterocycl. Chem., 16, 1423-1424 (1979) or according to Examples disclosed herein. That is, Compound A (P=hydrogen atom) is obtainable by causing dimethyl acetylenedicarboxylate to react with amide oxime ($R^1$—C (NH$_2$)=N—OH or $R^1$—C (=NH)—NR$^2$—OH) obtained by reaction between cyano compound ($R^1$—CN) and hydroxyamines (NHR$^2$—OH). Thereafter, the hydroxy may be protected as necessary.

Examples of the hydroxy protecting group P include acyl (e.g., acetyl, pivaloyl, benzoyl), aralkyl (e.g., benzyl), lower alkyl (e.g., methyl), alkoxyalkyl (e.g., methoxymethyl, methoxyethyl), lower alkylsulfonyl (e.g., methane sulfonyl), aryl sulfonyl (e.g., benzenesulfonyl, toluenesulfonyl) and alkoxycarbonyl (e.g., methoxycarbonyl).

Compound B is known in the art, or may be easily synthesized by one skilled in the art.

(Step 2)

This step is to produce Compound D from Compound C. Namely, dehydrating ring closure of oxazole or oxadiazole ring.

As a dehydrating agent, phosphorus oxychloride, phosphorus oxybromide, thionyl chloride, polyphosphoric acid, dibromotriphenyl phosphorane, 2-chloro-1,3-dimethylimidazolinium chloride, (methoxycarbonylsulfamoyl)triethyl ammonium hydroxide and the like may be used, and triphenylphosphine-carbon tetrachloride, and triphenylphosphine-iodine are preferred. Bases such as triethylamine and N,N-diethylaniline may be added as necessary.

The reaction temperature is from 0 to 150° C., and when triphenylphosphine-carbon tetrachloride or triphenylphosphine-iodine is used as a dehydrating agent, it is preferably from room temperature to 60° C.

As a reaction solvent, a wide variety of aprotic solvents can be used, and methylene chloride, chloroform, toluene, tetrahydrofuran and the like are preferred. When phosphorus oxychloride, thionyl chloride or polyphosphoric acid is used as the dehydrating agent, the reaction may be conducted in absence of solvent.

(Step 3)

This step is to produce Compound E from Compound D. Namely, it is deprotection of the hydroxy protecting group P and conducted as necessary.

When the hydroxy protecting group P is aralkyl or alkyl, trimethylsilyl chloride-sodium iodide, boron tribromide, hydrobromic acid and the like can be used as the deprotecting reagent. When the hydroxy protecting group is benzyl, the reaction may be achieved by catalytic hydrogenation under hydrogen atmosphere at 1 to 5 atmospheric pressure using palladium carbon, palladium hydroxide, platinum oxide and the like as a catalyst.

The reaction temperature is from 0 to 110° C., preferably from room temperature to 90° C. when trimethylsilyl chloride-sodium iodide or hydrobromic acid is used as the deprotecting reagent. It is from −78° C. to room temperature when boron tribromide is used as the deprotecting reagent. It is from 0 to 60° C., preferably room temperature when catalytic hydrogenation is conducted.

As to a reaction solvent, a polar solvent such as acetonitrile is preferably used when trimethylsilyl chloride-sodium iodide is used as the deprotecting reagent. When boron tribromide is used as the deprotecting reagent, aprotic solvents such as methylene chloride, chloroform and the like are preferably used. When hydrobromic acid is used as the deprotecting reagent, acetic acid or the like is preferably used. In catalytic hydrogenation, ethyl acetate, methanol, ethanol, tetrahydrofuran, 1,4-dioxane, dimethylformamide and the like solvents are preferably used.

(Process B)

[Formula 20]

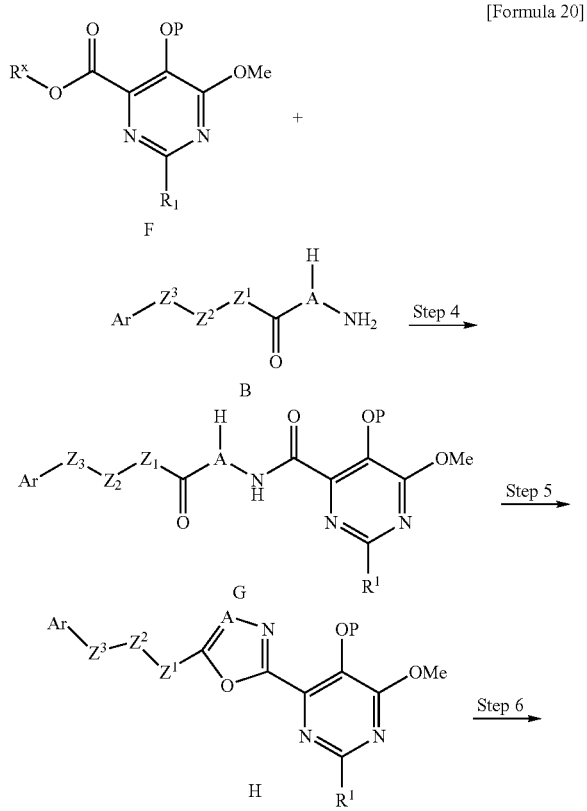

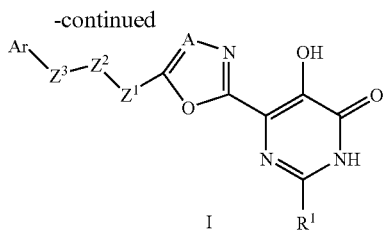

(wherein, P is hydrogen atom or hydroxy protecting group; A is CH or N; $R^x$ is lower alkyl (e.g., methyl or ethyl); Me is methyl; other symbols are the same meanings as above.)

(Step 4)

This step is to produce Compound G by condensation between Compound F and Compound B. This may be performed similarly to Step 1.

Compound F may be a compound described in WO 03/035077, or may be synthesized according to WO 03/035077 or examples given herein.

(Step 5)

This step is to produce Compound H from Compound G. This may be performed similarly to Step 2.

(Step 6)

This step is to produce Compound I from Compound H. Namely, it is deprotection of the hydroxy protecting group P and the methoxy protecting group. Similarly to Step 3, deprotection of methoxy protecting group may be conducted in a different stage following deprotection of the hydroxy protecting group P.

As a deprotecting reagent, trimethylsilylchloride-sodium iodide, boron tribromide, hydrobromic acid and the like can be used.

The reaction temperature is from 0 to 110° C., preferably from room temperature to 90° C. when trimethylsilylchloride-sodium iodide or hydrobromic acid is used as the deprotecting reagent, and from −78° C. to room temperature when boron tribromide is used as the deprotecting reagent.

As a reaction solvent, a polar solvent such as acetonitrile is preferably used when trimethylsilyl chloride-sodium iodide is used as the deprotecting reagent. When boron tribromide is used as the deprotecting reagent, an aprotic solvent such as methylene chloride or chloroform is preferably used. When hydrobromic acid is used as the deprotecting reagent, acetic acid or the like is preferably used.

(Process C)

[Formula 21]

-continued

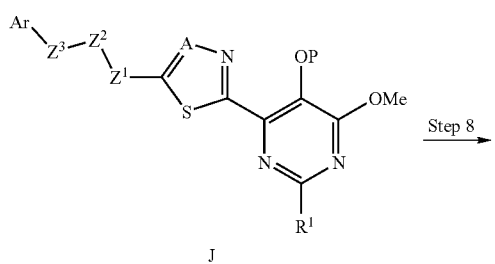

J

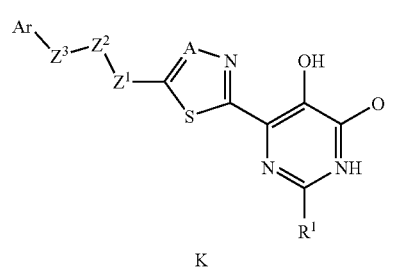

K (wherein, P is hydrogen atom or hydroxy protecting group; A is CH or N; $R^x$ is lower alkyl (e.g., methyl, ethyl); other symbols are the same meanings as above.)

(Step 7)

This is a step to produce Compound J from Compound G. Namely, it is ring closure reaction of the thiazole or thiadiazole ring.

As a reaction reagent, phosphorus pentasulfide and Lawson's reagent are used.

The reaction temperature is from 50 to 150° C., preferably from 80 to 120° C.

As a reaction solvent, toluene, tetrahydrofuran, pyridine and the like are preferred.

(Step 8)

This step is to produce Compound K from Compound J. It may be performed similarly to Step 6.

In the above Processes A to C, a salt or a reactive derivative may be used as a starting material. When there is a functional group on the moieties Ar, $R^1$ and $R^2$, it may be protected before a respective reaction. Deprotection of such a protecting group may be conducted prior to a final step, or concurrently with the step.

In Processes A to C, chemical modification of substituent may be conducted on the moieties Ar, $R^1$ and $R^2$, especially on the moiety $R^1$ during an interval of any steps. For example, in synthesis of Compound E in which $R^1$ is lower alkyl that is substituted with substituted amino, the amino moiety may be chemically modified after obtaining Compound E in which $R^1$ is amino lower alkyl according to Process A.

(2) In the case where X is a group shown by (b)

(Process D)

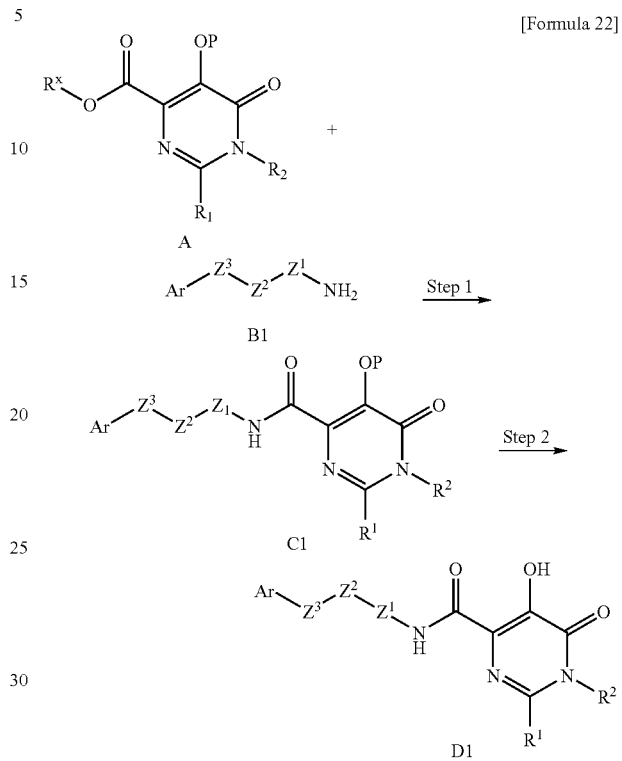

[Formula 22]

(wherein, P is hydrogen atom or hydroxy protecting group; $R^x$ is lower alkyl (e.g., methyl, ethyl); other symbols are the same meanings as above.)

(Step 1)

This step is to produce Compound C1 by condensation between Compound A and Compound B1. Namely, it is amidation of a carboxylic acid derivative described in, for example, "Advanced Organic Chemistry. $3^{Rd}$ ed." John Wiley & Sons, 1985, p 370-376, and may be performed according to Step 1 of Process A.

(Step 2)

This step is to produce Compound D1 from Compound C1. Namely, it is deprotection of the hydroxy protecting group P, and is performed as needed. The reaction may be performed in accordance with Step 3 of Process A.

The aforementioned amidation can be performed similarly by using Compound F which is the staring material of Process B.

(3) In the case where X is a group represented by (c)

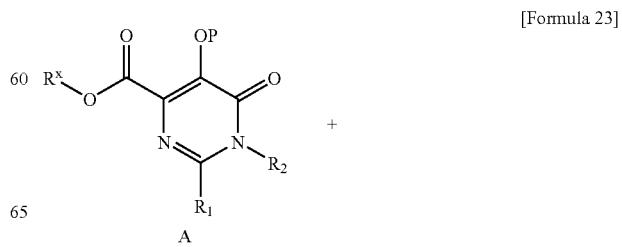

[Formula 23]

-continued

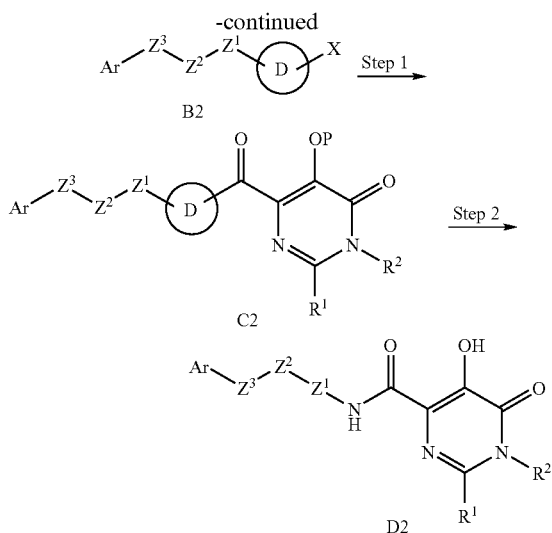

(wherein P is hydrogen atom or hydroxy protecting group; $R^x$ is lower alkyl (e.g., methyl or ethyl); X is a leaving group such as halogen; and other symbols are the same meanings as above.)

(Step 1)

This step is to produce Compound C1 by condensation between Compound A and Compound B2. Namely, it is acylation in the presence of a base, and can be performed according to the method described in Patent document (WO 03/016275).

(Step 2)

This step is to produce Compound D2 from Compound C2. Namely, it is deprotection of the hydroxy protecting group P performed as needed. The reaction may be performed in accordance with Step 3 of Process A.

The reaction of the above Step 1 can be performed similarly by using Compound F which is the starting material of Process B.

(4) In the case where $R^1$ and $R^2$ moieties form heterocyclic ring together with an adjacent atom In each of the aforementioned Processes, the moieties $R^1$ and $R^2$ may together form a ring already when they are starting materials. Alternatively, as will be described later, first Compound (I-X) in which $R^1$ and $R^2$ are not coupled with each other is obtained by each Process, and then Compound (I-X) may be subjected to ring formation to give Compound (I-Y).

[Formula 24]

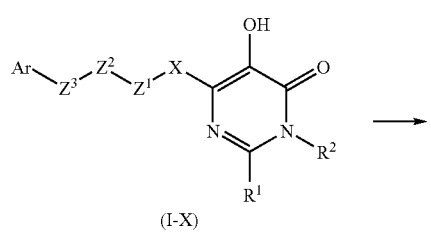

-continued

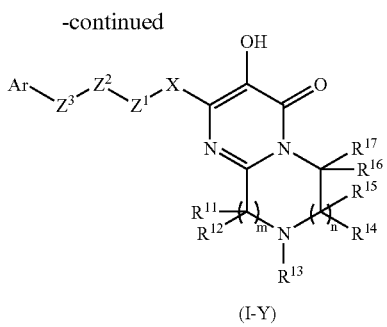

For example, as exemplified in Examples 24, 25, 28 and the like, condensation may be performed using aldehyde such as formalin or ketone such as acetone as a starting material.

The reaction temperature is from 0 to 140° C., preferably from 25 to 80° C.

As a reaction solvent, acetic acid, formic acid, methylene chloride, tetrahydrofuran and the like may be used.

Also as exemplified in Example 26, $R^1$ may be subjected to ring closure with $R^2$ moiety after extension of a carbon chain by chemical modification of the terminal amino moiety of $R^1$.

The reaction temperature is from 0 to 100° C., preferably from 25 to 50° C.

As a reaction solvent, N,N-dimethylformamide, pyridine or the like is used.

In the above Processes (2) to (4), a salt or a reactive derivative may be used as each starting material. When there is any functional group on Ar, $R^1$ and $R^2$ moieties, it may be protected prior to a respective reaction. Deprotection of such a protecting group may be conducted prior to a final step, or concurrently with the step.

The condensed ring part of Compound (I-Y) obtained in the above process (4) may further be chemically modified.

The compound of the present invention is useful as a pharmaceutical composition such as an antiviral agent. The compound of the present invention has an outstanding inhibitory activity against integrase of viruses. Therefore, the compound of the present invention is expected to prevent or treat various diseases caused by viruses producing integrase to grow in animal cells upon infection, and is useful as, for example, an integrase inhibitor against retroviruses (e.g., HIV-1, HIV-2, HTLV-1, SIV or FIV), especially, an anti-HIV agent.

The compound of the present invention can be used in a combination therapy with an anti-HIV agent possessing other inhibitory mechanism such as a reverse transcriptase inhibitory agent and/or a protease inhibitory agent. Since any integrase inhibitor has not been on sale yet, it is useful to use the compound of the present invention in combination therapy with a reverse transcriptase inhibitory agent and/or a protease inhibitory agent.

And the compound of the present invention can be used not only as an anti-HIV mixture but also as a concomitant agent enhancing the activity of the other anti-HIV agent in a cocktail therapy.

The compound of the present invention can be used so as in the gene therapy using a retrovirus vector derived from HIV or MLV to suppress the spread of the retrovirus vector infection over non-target tissues. Especially, in the case that cells infected with such a vector in vitro are put back in a body, a previous administration of the compound of the present invention prevents an unnecessary infection in the body.

The compounds of the present invention can be administered orally or parenterally. For oral administration, the compounds of the present invention can be used in any form of usual formulations, for example, solid formulations such as tablets, powders, granules, capsules; aqueous formulations; oleaginous suspensions; or solutions such as syrup or elixir. For parenteral administration, the compounds of the present invention can be used as an aqueous or oleaginous suspension injection, or nose drops. In the preparation of such formulations, conventional excipients, binding agents, lubricants, aqueous solvents, oleaginous solvents, emulsifying agents, suspending agents, preservatives or stabilizers can be optionally used. And as an anti-HIV agent, oral agents are especially preferable.

The formulation according to the present invention may be manufactured by combining (for example, admixing) a curatively effective amount of a compound of the present invention with a pharmaceutically acceptable carrier or diluent. The formulation of the present invention may be manufactured with well-known and easily available ingredients in accordance with a known method.

In the case of manufacturing a pharmaceutical composition according to the present invention, an active ingredient is admixed or diluted with a carrier, or they are contained in a carrier in the form of capsule, sacheier, paper, or another container. In the case of a carrier functioning as a diluent, the carrier is a solid, semi-solid, or liquid material, which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to formulate a compound of the present invention prior to administration.

Any suitable carrier well known to those skilled in the art may be used for the formulation. In such formulation, a carrier is in the form of solid, liquid or a mixture thereof. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator or capsule. A tablet for oral administration contains a suitable excipient such as calcium carbonate, sodium carbonate and lactose, calcium phosphate together with a disintegrator such as corn starch and alginic acid and/or a binder such as gelatin and acacia, and a lubricant such as magnesium stearate, stearic acid and talc.

In a powder medicine, a carrier is a finely pulverized solid, which is blended with finely pulverized active ingredients. In a tablet, active ingredients are admixed with a carrier having required binding power in a suitable ratio, and it is solidified in a desired shape and size. Powder medicine and tablet contain as the active ingredient about 1 to about 99% by weight of novel compounds of the present invention. Example of suitable solid carriers include magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

A liquid formulation contains suspending agent, emulsifier, syrup agent or elixir agent. Active ingredients may be dissolved or suspended into a pharmaceutically acceptable carrier such as sterile water, a sterile organic solvent or a mixture thereof. Active ingredients may be dissolved frequently into a suitable organic solvent such as propylene glycol aqueous solution. When finely pulverized active ingredients are dispersed into aqueous starch, sodium carboxymethylcellulose solution or suitable oil, the other compositions can be prepared.

Although an appropriate dosage of the compound of the present invention varies depending on the administration route, age, bodyweight, conditions of the patient, and kind of disease, in the case of oral administration, the daily dosage for an adult can be between approximately 0.05-3000 mg, preferably approximately 0.1-1000 mg, for an adult, if necessary, in divisions. In the case of parenteral administration, the daily dosage for an adult can be between approximately 0.01-1000 mg, preferably approximately 0.05-500 mg.

BEST MODE FOR CARRYING OUT THE INVENTION

Abbreviations

Me=methyl; Bn=benzyl; BZ=benzoyl; Boc=tert-butoxycarbonyl; CbZ=benzyloxycarbonyl; DMSO=dimethylsulfoxide Example 1

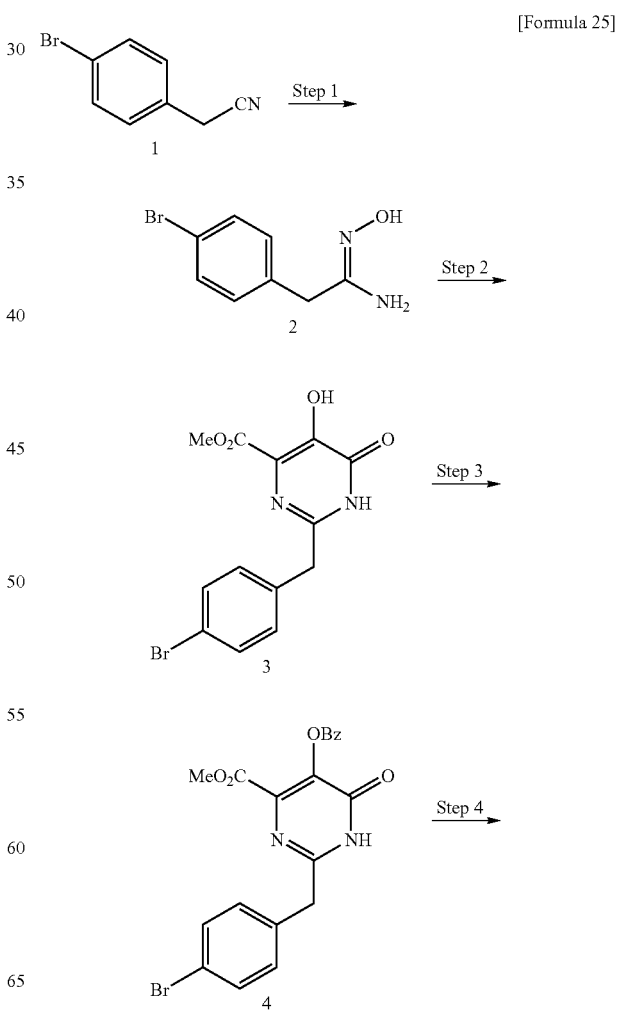

[Formula 25]

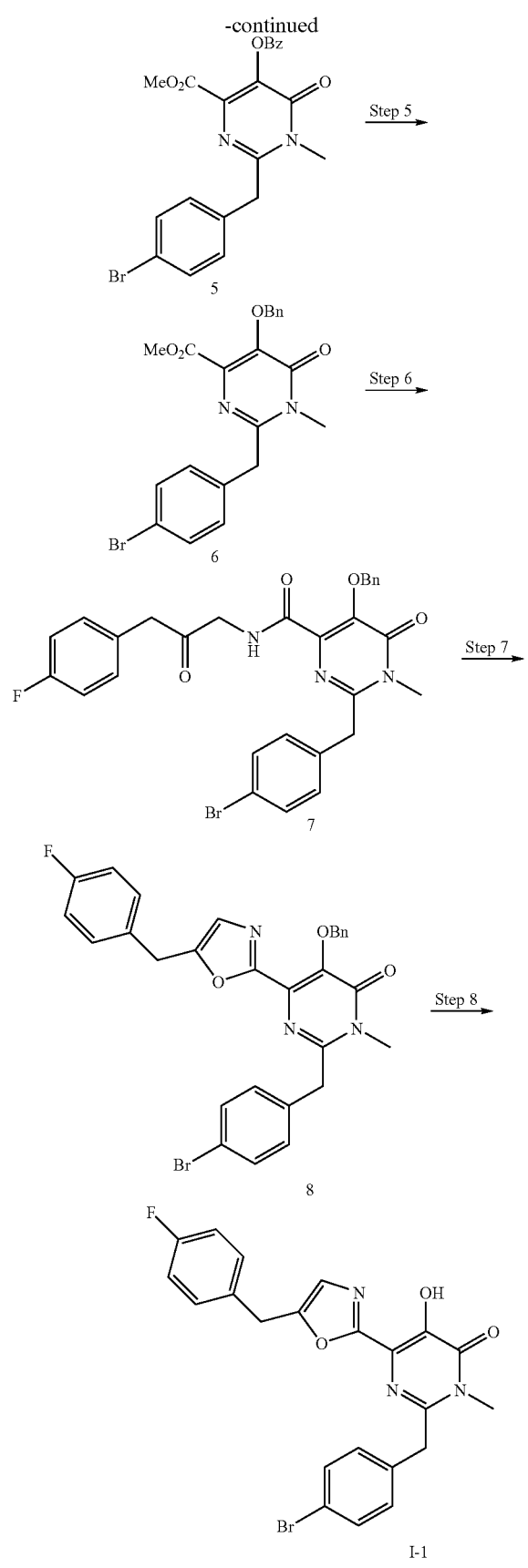

Step 1

To a methanol (200 ml) solution of potassium hydroxide (3.90 g, 69.5 mmol) was added hydroxylammonium chloride (4.80 g, 69.1 mmol) at room temperature, and the mixture was stirred for 10 minutes. To a filtrate obtained by filtering off the inorganic salt was added 4-bromophenyl acetonitrile (11.8 g, 60.2 mmol) at room temperature and stirred for 18 hours at 40° C. To a residue obtained by distilling off the solvent under reduced pressure, was added water (200 ml), and extracted with chloroform. After washing the extract with saturated brine (100 ml), it was dried over anhydrous sodium sulfate. The solvent was distilled off under reduced pressure to give a crude product of Compound 2.

Step 2

To a chloroform (300 ml) solution of the crude product of Compound 2 was added dimethyl acetylene dicarboxylate (8.10 ml, 65.9 mmol) at room temperature and the mixture was refluxed under heating for 2 hours. Brown oily xylene (150 ml) solution obtained by distilling off the solvent under reduced pressure was refluxed under heating for 16 hours. The solvent was distilled off under reduced pressure to give a crude product of Compound 3.

Step 3

To a pyridine (150 ml) solution of the above crude product of Compound 3 was added benzoic anhydride (20.4 g, 90.2 mmol) at room temperature, and the mixture was stirred for 15 hours. A residue obtained by distilling off the solvent under reduced pressure was diluted in ethyl acetate (450 ml), and washed with 1M hydrochloric acid (300 ml), water (300 ml), saturated sodium bicarbonate water (150 ml) and saturated brine (150 ml), and then dried over anhydrous sodium sulfate. A crude product obtained by distilling off the solvent under reduced pressure was subjected to silica gel chromatography. A fraction of objective product resulting from elution with hexane-ethyl acetate (3:1 v/v) was concentrated under reduced pressure, to give Compound 4 (3.15 g, 12% overall yield) as colorless crystals.

Step 4

To a tetrahydrofuran-dimethylformamide (1:1 v/v, 60 ml) solution of Compound 4 (3.15 g, 7.11 mmol) were added cesium carbonate (2.80 g, 8.59 mmol) and methyl iodide (0.880 ml, 14.1 mmol) at room temperature, and the mixture was stirred for 1 hour. The reaction solution was added with saturated ammonium chloride aqueous solution and extracted with ethyl acetate. After washing the extract with water and saturated brine, it was dried over anhydrous magnesium sulfate. A crude product obtained by distilling off the solvent under reduced pressure was subjected to silica gel chromatography. A fraction of objective product resulting from elution with hexane-ethyl acetate (1:1 v/v) was concentrated under reduced pressure to give Compound 5 (2.48 g, 76% yield) as colorless crystals.

Step 5

To a methanol (30 ml) solution of Compound 5 (2.48 g, 5.42 mmol) was added 28% methanol solution (1.60 ml) of sodium methoxide under ice-cooling, and the mixture was stirred for 5 hours at room temperature. To the reaction solution were added 1M hydrochloric acid (8 ml) and water (100 ml), and the precipitated crystals were collected by filtration and washed with water. To an acetone-dimethylformamide (1:2 v/v, 60 ml) solution of these crystals were added potassium carbonate (705 mg, 5.10 mmol) and benzyl bromide (0.600 ml, 5.04 mmol) at room temperature, and the mixture was stirred for 2 hours. To the reaction solution was added an aqueous solution of saturated ammonium chloride, followed by extraction with ethyl acetate. The extract was washed with water and saturated brine, and then dried over anhydrous magnesium sulfate. A crude product obtained by distilling off the solvent under reduced pressure was subjected to silica gel chromatography. A fraction of objective product resulting from elution with hexane-ethyl acetate (1:1 v/v) was concentrated under reduced pressure to give Compound 6 (840 mg, 41% yield) as colorless crystals.

Step 6

To a methanol (4 ml) solution of Compound 6 (840 mg, 1.89 mmol) was added 1M lithium hydroxide solution (3 ml) at room temperature and the mixture was stirred for 5 hours. The reaction mixture was added with an aqueous solution of citric acid, and extracted with chloroform. The extract was washed with water and then dried over anhydrous sodium sulfate. To a dimethylformamide (10 ml) solution of the crude product obtained by distilling off the solution under reduced pressure, 1-amino-3-(4-fluorophenyl)propane-2-on hydrochloric acid salt (448 mg, 2.20 mmol) and 1-hydroxybenzotriazole (297 mg, 2.20 mmol), were added 1-ethyl-3-(3-dimethylaminopropyl)carbodiimide hydrochloric acid salt (131 mg, 0.683 mmol) and triethylamine (0.310 ml, 2.22 mmol) at room temperature, and the mixture was stirred for 3 hours. The reaction solution was added with saturated sodium bicarbonate water and extracted with ethylacetate. The extract was washed with water and saturated brine, and then dried over anhydrous sodium sulfate. A crude product obtained by distilling off the solvent under reduced pressure was subjected to silica gel chromatography. A fraction of objective product resulting from elution with hexane-ethyl acetate (1:1 v/v) was concentrated under reduced pressure to give Compound 7 (910 mg, 83% yield) as colorless crystals.

Step 7

To an acetonitrile (10 ml) solution of Compound 7 (910 mg, 1.57 mmol), carbon tetrachloride (0.910 ml, 9.43 mmol) and triethylamine (0.700 ml, 5.02 mmol) was added triphenylphosphine (1.20 g, 4.58 mmol) at room temperature, and the mixture was stirred for 3 hours. A crude product obtained by distilling off the solvent under reduced pressure was subjected to silica gel chromatography. A fraction of objective product resulting from elution with toluene-acetone (6:1 v/v) was concentrated under reduced pressure to give Compound 8 (280 mg, 32% yield) as colorless crystals.

Step 8

To an acetonitrile (3 ml) solution of Compound 8 (280 mg, 0.500 mmol) and sodium iodide (599 mg, 4.00 mmol) was added chlorotrimethylsilane (0.500 ml, 3.94 mmol) at room temperature, and the mixture was stirred for 1 hour. The reaction solution was added with an aqueous solution of sodium hydrogen nitrite, and extracted with chloroform. The extract was washed with water and dried over anhydrous sodium sulfate. A crystalline residue obtained by distilling off solvent under reduced pressure was recrystallized from acetonitrile to give Compound I-1 (157 mg, 67% yield) as colorless crystals.

Melting point: 227-228° C. Recrystallization solvent: acetonitrile

NMR (CDCl3) d: 3.46 (3H, s), 4.12 (2H, s), 4.15 (2H, s), 6.89 (1H, s), 7.02-7.09 (4H, m), 7.23-7.28 (2H, m), 7.45-7.47 (2H, m).

Elemental analysis for $C_{22}H_{17}BrFN_3O_3$

Calcd. (%): C, 56.19; H, 3.64; N, 8.93; Br, 16.99; F, 4.04.
Found. (%): C, 56.35; H, 3.57; N, 8.93; Br, 17.08; F, 4.11.

Example 2

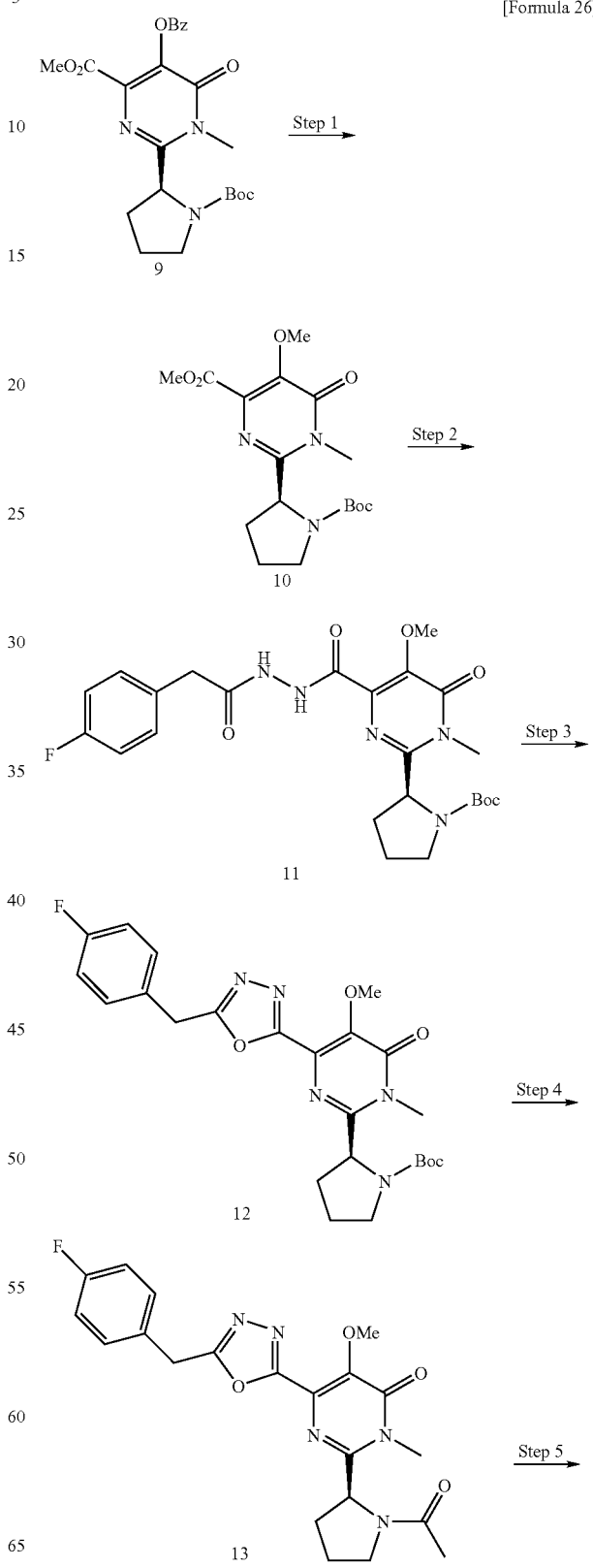

[Formula 26]

-continued

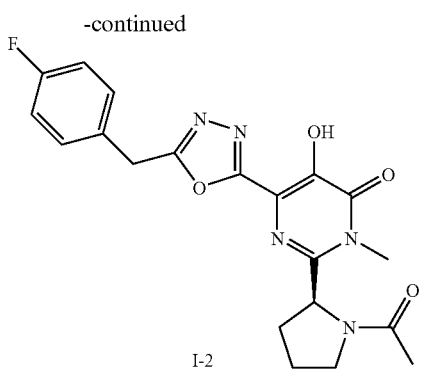

I-2

Step 1

To a methanol (70 ml) solution of Compound 9 (7.15 g, 15.6 mmol) disclosed in Patent (WO 03/035077) was added 28% methanol solution (4.70 ml) of sodium methoxide under ice-cooling, and the mixture was stirred for 30 minutes. The reaction solution was added with 2M hydrochloric acid (11.5 ml) under ice-cooling, and extracted with ethyl acetate. The extract was washed with saturated brine and then dried over anhydrous sodium sulfate. To a dimethylformamide (50 ml) solution of the crude product obtained by distilling off the solvent under reduced pressure were added potassium carbonate (2.58 g, 18.7 mmol) and methyl iodide (2.00 ml, 32.1 mmol) at room temperature, and the mixture was stirred for 2 hours at 60° C. The reaction solution was poured into 1M hydrochloric acid (100 ml) and then extracted with ethyl acetate. The extract was washed with water (100 ml) and saturated brine (100 ml), and then dried over anhydrous sodium sulfate. A crude product obtained by distilling off the solvent under reduced pressure was subjected to silica gel chromatography. A fraction of objective product resulting from elution with ethyl acetate was concentrated under reduced pressure to give Compound 10 (5.32 g, 93% yield) as brown oil.

Step 2

To a methanol (50 ml) solution of Compound 10 (5.32 g, 14.5 mmol) was added 1M lithium hydroxide solution (22 ml) at room temperature, and the mixture was stirred for 1 hour. The reaction solution was added with 2 M hydrochloric acid (10 ml), extracted with chloroform, and dried over anhydrous sodium sulfate. To a tetrahydrofuran (80 ml) solution of a crude product obtained by distilling off solvent under reduced pressure, 4-fluorophenylacetic acid hydrazide (2.30 g, 13.7 mmol) and 1-hydroxybenzotriazole (154 mg, 1.14 mmol), was added 1-ethyl-3-(3-dimethylaminopropyl)carbodiimide hydrochloric acid salt (2.62 g, 13.7 mmol) at room temperature, and the mixture was stirred for 2 hours. The reaction solution was added with water (160 ml), and extracted with ethyl acetate. The extract was washed with water (200 ml) and saturated brine (100 ml), and then dried over anhydrous sodium sulfate. The solvent was distilled off under reduced pressure to give a crude product (5.58 g) of Compound 11.

Step 3

To an acetonitrile (50 ml) solution of the above crude product (5.58 g) of Compound 11, carbon tetrachloride (6.80 ml, 70.5 mmol) and triethylamine (5.00 ml, 35.9 mmol), was added triphenylphosphine (8.73 g, 33.3 mmol) at room temperature, and the mixture was stirred for 1 hour. The reaction solution was diluted in ethyl acetate (500 ml), washed with saturated sodium bicarbonate water (200 ml), water (200 ml) and saturated brine (100 ml), and then dried over anhydrous sodium sulfate. A crude product obtained by distilling off the solvent under reduced pressure was subjected to silica gel chromatography. A fraction of objective product resulting from elution with ethyl acetate was concentrated under reduced pressure to give Compound 12 (5.07 g, 72% overall yield) as brown oil.

Step 4

To Compound 12 (5.07 g, 10.4 mmol) was added trifluoroacetic acid-methylene chloride (1:2 v/v, 50 ml) at room temperature, and the mixture was stirred for 1.5 hours. A solvent was distilled off under reduced pressure to give crude product (8.98 g). To a pyridine (3 ml) solution of this crude product (608 mg) and 4-dimethylaminopyridine (15.0 mg, 0.123 mmol) was added acetic anhydride (0.115 ml, 1.22 mmol) at room temperature, and the mixture was stirred for 19 hours. The reaction solution was diluted in ethyl acetate (50 ml), washed with 1M hydrochloric acid (20 ml), water (20 ml) and saturated brine (20 ml), and then dried over anhydrous sodium sulfate. A crude product obtained by distilling off the solvent under reduced pressure was subjected to silica gel chromatography. A fraction of objective product resulting from elution with chloroform-methanol (30:1 v/v) was concentrated under reduced pressure to give Compound 13 (217 mg, 72% yield) as brown oil.

Step 5

To a methylene chloride (4 ml) solution of Compound 13 (5.32 g, 14.5 mmol) was added 1.0 M methylene chloride solution (2.00 ml, 2.00 mmol) of boron tribromide under ice-cooling, and the mixture was stirred for 1 hour. The reaction solution was added with water (4 ml) and saturated sodium bicarbonate water (4 ml), and extracted with ethyl acetate. The extract was washed with water and saturated brine, and then dried over anhydrous sodium sulfate. A crystalline residue obtained by distilling off the solvent under reduced pressure was recrystallized from isopropanol, to give Compound I-2 (63.9 mg, 30% yield) as colorless crystals.

Melting point: 170-172° C. Recrystallization solvent: isopropanol

NMR (CDCl3) d: 1.90-2.34 (4H, m), 2.04 (3H, s), 3.57-3.81 (2H, m), 3.73 (3H, s), 4.29 (2H, s), 5.16 (1H, m), 7.06 (2H, m), 7.33 (2H, m), 9.34 (1H, brs).

Elemental analysis for $C_{20}H_{20}FN_5O_4$

Calcd. (%): C, 58.11; H, 4.88; N, 16.94; F, 4.60.

Found. (%): C, 57.88; H, 4.90; N, 16.65; F, 4.24.

Example 3

[Formula 27]

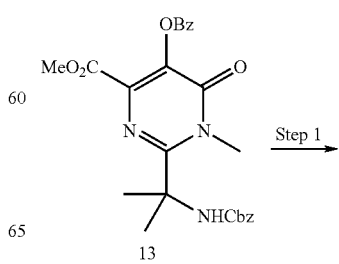

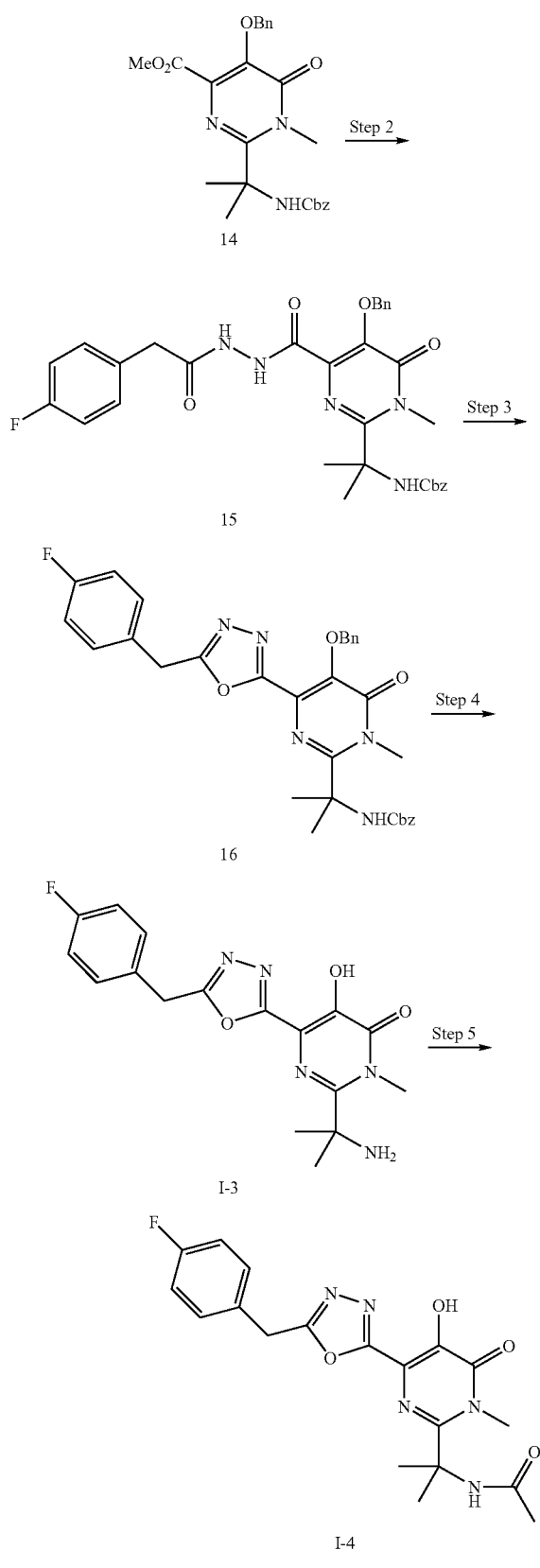

Step 1

Reaction was performed in accordance with the method described in Step 5 of Example 1 using Compound 13 described in Patent (WO 03/035077) to give Compound 14.

Step 2

Reaction was performed in accordance with the method described in Step 2 of Example 2 using Compound 14 to give a crude product of Compound 15.

Step 3

To a methylene chloride (40 ml) solution of iodine (2.15 g, 16.9 mmol) was added a methylene chloride (20 ml) solution of triphenylphosphine (3.55 g, 13.5 mmol), triethylamine (3.80 ml, 27.3 mmol) and the above crude product (4.08 g) of Compound 15 at room temperature, and the mixture was stirred for 3.5 hours. A crude product obtained by distilling off the solvent under reduced pressure was subjected to silica gel chromatography. A fraction of objective product resulting from elution with hexane-ethyl acetate (1:1 v/v) was concentrated under reduced pressure to give Compound 16 as colorless crystals.

Step 4

An ethyl acetate-methanol (1:1 v/v, 200 ml) suspension of Compound 16 and 10% palladium carbon (494 mg) was stirred at room temperature for 17 hours in hydrogen atmosphere of 1 atmospheric pressure. The reaction solution was added with dimethylformamide, and the precipitated crystal was dissolved and then filtered. A crystalline residue obtained by distilling off the solvent under reduced pressure was washed with methanol, and Compound I-3 (2.29 g, 94% overall yield) was obtained as light brown crystals.

Melting point: 226-228° C.

NMR (DMSO-$d_6$) d: 1.53 (6H, s), 3.84 (3H, s), 4.33 (2H, s), 7.19 (2H, m), 7.40 (2H, m).

MS (positive FABMS): m/Z 360 $(M+H)^+$, 719 $(2M+H)^+$.

Step 5

To a methylene chloride (4 ml) solution of Compound I-3 (200 mg, 0.557 mmol) and triethylamine (0.230 ml, 1.65 mmol) was added acetic anhydride (0.156 ml, 1.65 mmol) at room temperature, and the mixture was stirred for 17 hours. The reaction solution was added with 0.5 M hydrochloric acid (10 ml), and extracted with ethyl acetate. The extract was washed with water (10 ml) and saturated brine (5 ml), and then dried over anhydrous sodium sulfate. To a methanol (5 ml) solution or a crude product obtained by distilling off solvent under reduced pressure, was added 1M lithium hydroxide solution (1 ml) at room temperature, and the mixture was stirred for 20 minutes. The reaction solution was added with 2M hydrochloric acid (0.5 ml) and water (6 ml), and the precipitated crystals were collected by filtration, and washed with water to give Compound I-4 (160 mg, 72% yield) as colorless crystals.

Melting point: 215-216° C.

NMR (DMSO-$d_6$) d: 1.56 (6H, s), 1.84 (3H, s), 3.54 (3H, s), 4.37 (2H, s), 7.19 (2H, m), 7.41 (2H, m), 8.47 (1H, s), 10.45 (1H, brs).

MS (positive FABMS): m/Z 402 $(M+H)^+$, 803 $(2M+H)^+$.

Example 4

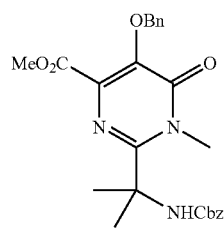

14

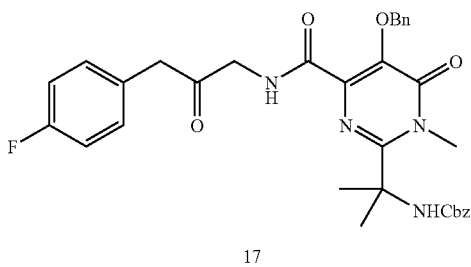

17

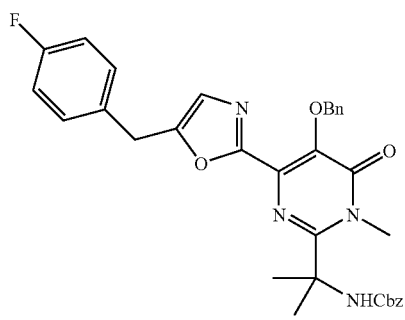

18

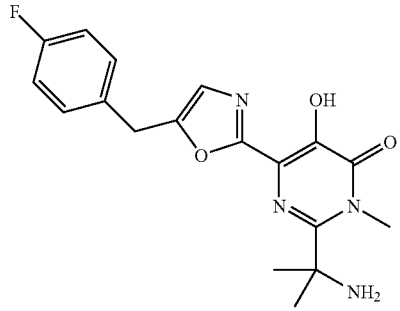

I-5

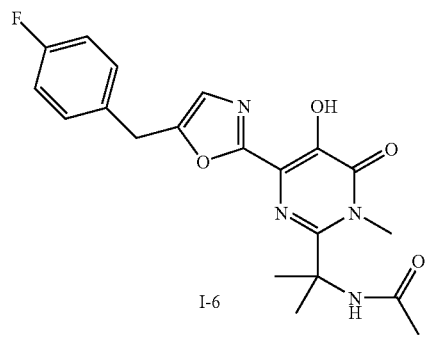

I-6

[Formula 28]

Step 1

Step 2

Step 3

Step 4

Step 1
Reaction was performed in accordance with the method described in Step 6 of Example 1 using Compound 14 obtained from Step 1 of Example 3, to give Compound 17.

Step 2
Reaction was performed in accordance with the method described in Step 7 of Example 1 using Compound 17, to give Compound 18.

Step 3
Reaction was performed in accordance with the method described in Step 8 of Example 1 using Compound 18 to give Compound I-5.

Melting point: 213-215° C. Recrystallization solvent: chloroform-ethyl acetate

NMR (DMSO-$d_6$) d: 1.71 (6H, s), 3.60 (3H, s), 4-0.17 (2H, s), 7.18 (2H, m), 7.24 (1H, s), 7.37 (2H, m), 8.42 (2H, brs), 10.67 (1H, brs).

MS (positive FABMS): m/Z 359 (M+H)$^+$, 717 (2M+H)$^+$.

Step 4
Reaction was performed in accordance with the method described in Step 5 of Example 3 using Compound I-5 to give Compound I-6.

Melting point: 237-238° C.

NMR (DMSO-$d_6$) d: 1.57 (6H, s), 1.84 (3H, s), 3.52 (3H, s), 4.17 (2H, s), 7.17 (2H, m), 7.17 (1H, s), 7.37 (2H, m), 8.46 (1H, s), 10.46 (1H, brs).

MS (positive FABMS): m/Z 401 (M+H)$^+$, 801 (2M+H)$^+$.

Example 5

[Formula 29]

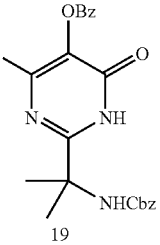

19

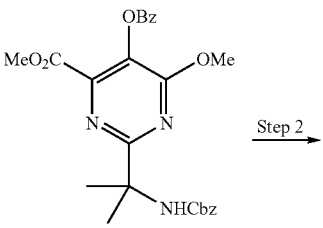

20

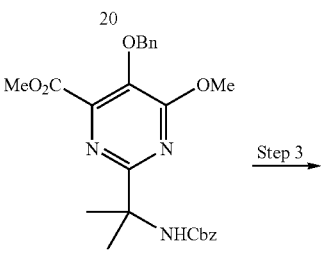

21

Step 1

Step 2

Step 3

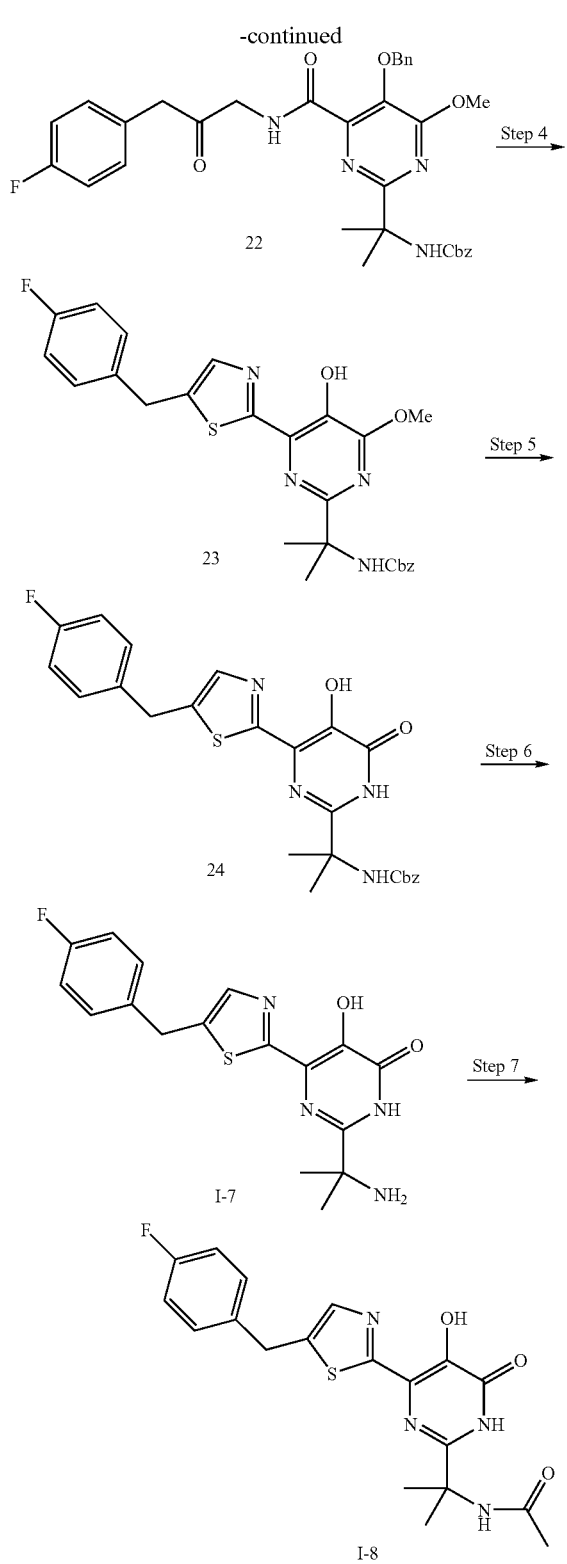

Step 1

Reaction was performed in accordance with the method described in Step 4 of Example 1 using Compound 19 described in Patent (WO 03/035077) to give Compound 20 (and Compound 9).

Step 2

Reaction was performed in accordance with the method described in Step 5 of Example 1 using Compound 20 to give Compound 21.

Step 3

Reaction was performed in accordance with the method described in Step 6 of Example 1 using Compound 21 to give Compound 22.

Step 4

To a toluene (60 ml) solution of Compound 22 (3.03 g, 5.04 mmol) was added Lawson's reagent (4.09 g, 10.1 mmol) at room temperature, and the mixture was refluxed under heat for 1 hour. The reaction solution was added with 1M hydrochloric acid (50 ml) under ice-cooling and extracted with ethyl acetate. The extract was washed with water (50 ml), saturated sodium bicarbonate water (50 ml) and saturated brine (50 ml), and then dried over anhydrous sodium sulfate. A crude product obtained by distilling off solvent under reduced pressure was subjected to silica gel column chromatography. A fraction of objective product resulting from elution with ethyl acetate was concentrated under reduced pressure to give a crude product of Compound 23. To a methylene chloride (50 ml) solution of the crude product (1.94 g) of Compound 23, triethylamine (1.40 ml, 10.0 mmol) and 4-dimethylaminopyridine (61.5 mg, 0.503 mmol) was added acetic anhydride (0.940 ml, 9.94 mmol) at room temperature, and the mixture was stirred for 24 hours. The reaction solution was added with water (50 ml), and extracted with ethyl acetate. The extract was washed with saturated brine (50 ml), and then dried over anhydrous sodium sulfate. A crude product obtained by distilling off the solvent under reduced pressure was subjected to silica gel chromatography. A fraction of objective product resulting from elution with hexane-ethyl acetate (3:1 v/v) was concentrated under reduced pressure to give an acetyl compound of Compound 23. To a methanol (20 ml) solution of the acetyl compound of Compound 23 (1.35 g, 2.45 mmol) was added 1M lithium hydroxide solution (5 ml) at room temperature, and the mixture was stirred for 1 hour. The reaction solution was added with 2M hydrochloric acid (2 ml), and extracted with ethyl acetate. The extract was washed with water and saturated brine, and then dried over anhydrous sodium sulfate. The solvent was distilled off under reduced pressure to give Compound 23 (1.25 g, 49% yield) as yellow oil.

Step 5

To an acetic acid (15 ml) solution of Compound 23 (1.25 g, 2.46 mmol) was added 47% hydrobromic acid at room temperature, and the mixture was stirred for 15 hours. The reaction solution was added with water (30 ml) and sodium hydroxide, extracted with chloroform, and the extract was dried over anhydrous sodium sulfate. The solvent was distilled off under reduced pressure to give Compound 24 (1.20 g, 99% yield) as yellow oil.

Step 6

To an acetonitrile (30 ml) solution of Compound 24 (1.20 g, 2.43 mmol) and sodium iodide (3.00 g, 20.0 mmol) was added chlorotrimethylsilane (2.50 ml, 19.7 mmol) under ice-cooling, and the mixture was stirred at room temperature four 26 hours. The reaction solution was added with water (10 ml), an aqueous solution of sodium hydrogen nitrite (10 ml) and 2M sodium hydroxide aqueous solution, and extracted with ethyl acetate. The extract was washed with water and saturated brine, and then dried over anhydrous sodium sulfate. A crystalline residue obtained by distilling off the solvent under reduced pressure was washed with methanol to give Compound I-7 (508 mg, 58% yield) as yellow crystals.

Melting point: 135-137° C.

NMR (DMSO-$d_6$) d: 1.40 (6H, s), 4.23 (2H, s), 7.15 (2H, m), 7.34 (2H, m), 7.79 (1H, s).

MS (positive FABMS): m/Z 361 (M+H)$^+$, 721 (2M+H)$^+$.

Step 7

Reaction was performed in accordance with Step 5 of Example 3 using Compound I-7 to give Compound I-8.

Melting point: 238-240° C.

NMR (DMSO-$d_6$) d: 1.46 (6H, s), 1.83 (3H, s), 4.27 (2H, s), 7.16 (2H, m), 7.36 (2H, m), 7.89 (1H, s), 8.04 (1H, s), 12.22 (1H, brs).

MS (positive FABMS): m/Z 403 (M+H)$^+$, 805 (2M+H)$^+$.

The present invention also involves the following compounds. These compounds may be synthesized in a similar manners as described in the above Examples.

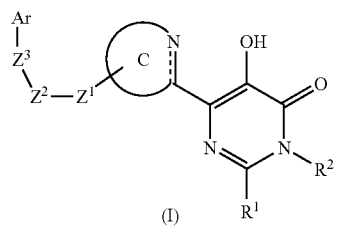

[Formula 30]

$R^2$: hydrogen atom or methyl

Ar—$Z^3$—$Z^2$—$Z^1$—C ring:

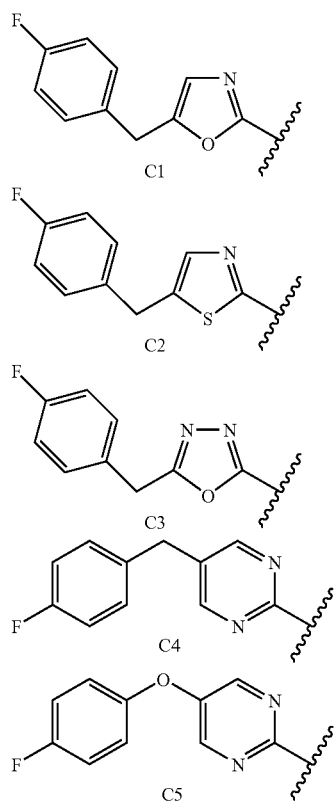

[Formula 31]

$R^1$:

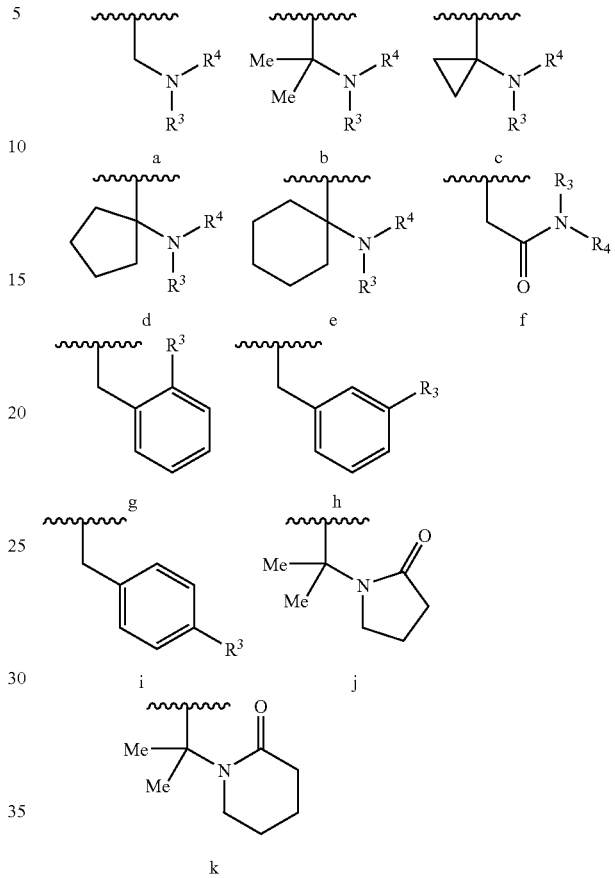

[Formula 32]

$R^3$: hydrogen atom (1), hydroxy (2), methoxy (3), amino (4), methylamino (5), dimethylamino (6), diethylamino (7), 1-pyrrolidino (8), 1-piperidino (9), 1-morpholino (10), 4-methylpiperazino (11), acetylamino (12), benzoylamino (13), acetylmethylamino (14), methane sulfonylamino (15), methyl (16), benzyl (17), formyl (18), acetyl (19), benzoyl (20), pyridine-2-carbonyl (21), pyridine-3-carbonyl (22), pyridine-4-carbonyl (23), carbamoyl (24), methylcarbamoyl (25), dimethylcarbamoyl (26), dimethylaminoacetyl (27), oxalyl (28), amino oxalyl (29), methylamino oxalyl (30), dimethylamino oxalyl (31), 4-methylpiperadino oxalyl (32), methane sulfonyl (33), benzene sulfonyl (34)

$R^4$: hydrogen atom or methyl

As a preferred combination of C ring moiety of the above Compound and $R^1$ and $R^3$ moieties, the followings are exemplified.

(1) When Ar—$Z^3$—$Z^2$—$Z^1$—C ring is C1

$R^1$ is a, and $R^3$ is (1), (16) to (34).

$R^1$ is b, $R^3$ is (16) to (18), (20) to (34).

$R^1$ is c, $R^3$ is (1), (16) to (34).

$R^1$ is d, $R^3$ is (1), (16) to (34).

$R^1$ is e, $R^3$ is (1), (16) to (34).

$R^1$ is f, $R^3$ is (1) to (17).

$R^1$ is g, $R^3$ is (1) to (26).

$R^1$ is h, $R^3$ is (2) to (26).
$R^1$ is i, $R^3$ is (2) to (26).
$R^1$ is j and k.

(2) When Ar—$Z^3$—$Z^2$—$Z^1$—C ring is C2
$R^1$ is a, $R^3$ is (1), (16) to (34).
$R^1$ is b, $R^3$ is (16) to (18), (20) to (34).
$R^1$ is c, $R^3$ is (1), (16) to (34).
$R^1$ is d, $R^3$ is (1), (16) to (34).
$R^1$ is e, $R^3$ is (1), (16) to (34).
$R^1$ is f, $R^3$ is (1) to (17).
$R^1$ is g, $R^3$ is (1) to (26).
$R^1$ is h, $R^3$ is (2) to (26).
$R^1$ is i, $R^3$ is (2) to (26).
$R^1$ is j and k.

(3) When Ar—$Z^3$—$Z^2$—$Z^1$—C ring is C3
$R^1$ is a, $R^3$ is (1), (16) to (34).
$R^1$ is b, $R^3$ is (16) to (18), (20) to (34).
$R^1$ is c, $R^3$ is (1), (16) to (34).
$R^1$ is d, $R^3$ is (1), (16) to (34).
$R^1$ is e, $R^3$ is (1), (16) to (34).
$R^1$ is f, $R^3$ is (1) to (17).
$R^1$ is g, $R^3$ is (1) to (26).
$R^1$ is h, $R^3$ is (2) to (26).
$R^1$ is i, $R^3$ is (2) to (26).
$R^1$ is j and k.

(4) When Ar—$Z^3$—$Z^2$—$Z^1$—C ring is C4
$R^1$ is a, $R^3$ is (1), (16) to (34).
$R^1$ is b, $R^3$ is (16) to (18), (20) to (34).
$R^1$ is c, $R^3$ is (1), (16) to (34).
$R^1$ is d, $R^3$ is (1), (16) to (34).
$R^1$ is e, $R^3$ is (1), (16) to (34).
$R^1$ is f, $R^3$ is (1) to (17).
$R^1$ is g, $R^3$ is (1) to (26).
$R^1$ is h, $R^3$ is (2) to (26).
$R^1$ is i, $R^3$ is (2) to (26).
$R^1$ is j and k.

(5) When Ar—$Z^3$—$Z^2$—$Z^1$—C ring is C5
$R^1$ is a, $R^3$ is (1), (16) to (34).
$R^1$ is b, $R^3$ is (16) to (18), (20) to (34).
$R^1$ is c, $R^3$ is (1), (16) to (34).
$R^1$ is d, $R^3$ is (1), (16) to (34).
$R^1$ is e, $R^3$ is (1), (16) to (34).
$R^1$ is f, $R^3$ is (1) to (17).
$R^1$ is g, $R^3$ is (1) to (26).
$R^1$ is h, $R^3$ is (2) to (26).
$R^1$ is i, $R^3$ is (2) to (26).
$R^1$ is j and k.

Example 6

[Formula 33]

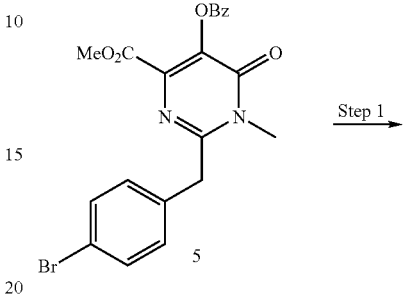

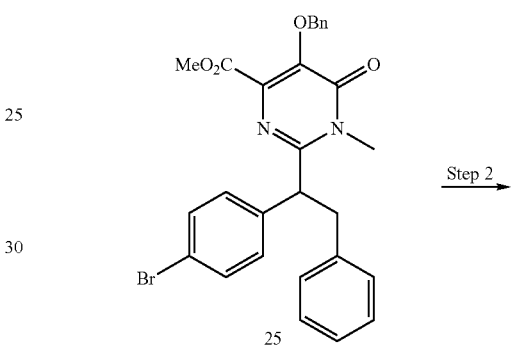

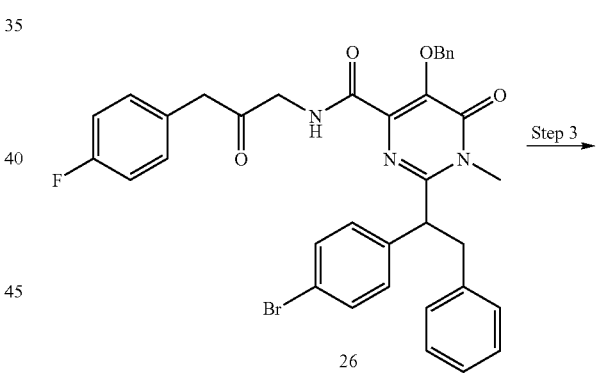

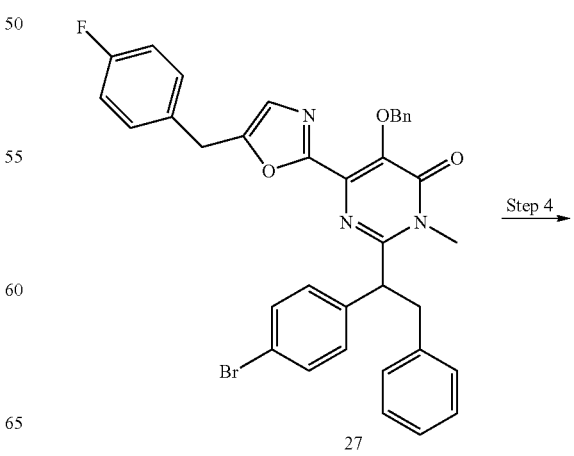

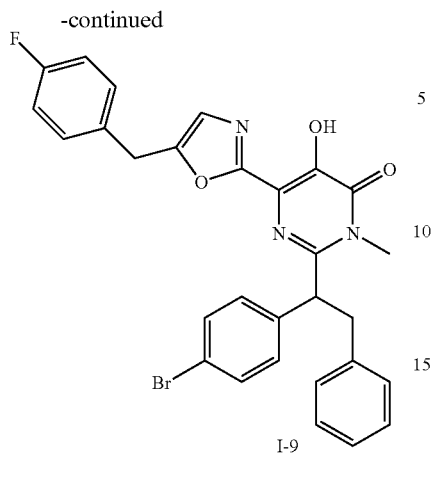

I-9

Step 1

Reaction was performed in accordance with the method described in Step 5 of Example 1 using Compound 5 (1.65 g, 4.67 mmol) obtained from Step 4 of Example 1 to give Compound 25 (1.57 g, 63% yield) as an oily product.

Step 2

Reaction was performed in accordance with the method described in Step 6 of Example 1 using Compound 25 (1.57 g, 2.94 mmol) to give Compound 26 (1.53 g, 78% yield) as an oily product.

Step 3

Reaction was performed in accordance with the method described in Step 7 of Example 1 using Compound 26 (1.53 g, 2.29 mmol) to give Compound 27 (760 mg, 51% yield) as an oily product.

Step 4

Reaction was performed in accordance with the method described in Step 8 of Example 1 using Compound 27 (760 mg, 1.17 mmol) to give Compound I-9 (420 mg, 63% yield) as pale yellow crystals.

Melting point: 179-181° C. Recrystallization solvent: methanol

NMR (CDCl3) d: 3.12 (1H, dd, J=6.5, 13.5 Hz), 3.36 (3H, s), 3.72 (1H, dd, J=8.0, 13.5 Hz), 4.17-4.21 (3H, m), 6.97 (1H, s), 7.01-7.16 (10H, m), 7.30-7.35 (2H, m), 7.38-7.42 (2H, m).

Elemental analysis for $C_{29}H_{22}BrFN_3O_3$

Calcd. (%): C, 62.15; H, 4.14; N, 7.50; Br, 14.26; F, 3.39.
Found. (%): C, 62.13; H, 4.07; N, 7.51; Br, 14.20; F, 3.32.

Example 7

[Formula 34]

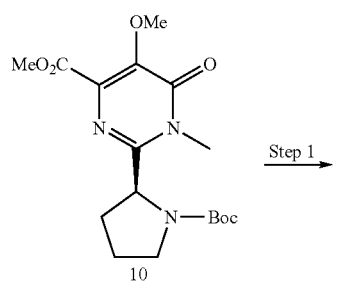

10

Step 1

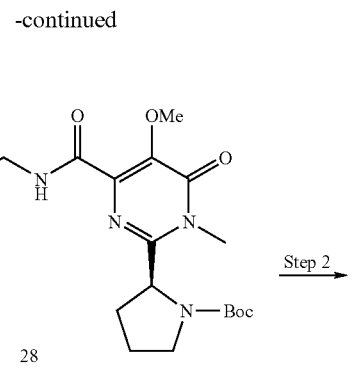

28

Step 2

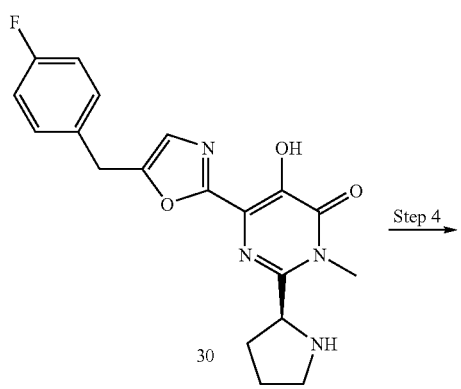

29

Step 3

30

Step 4

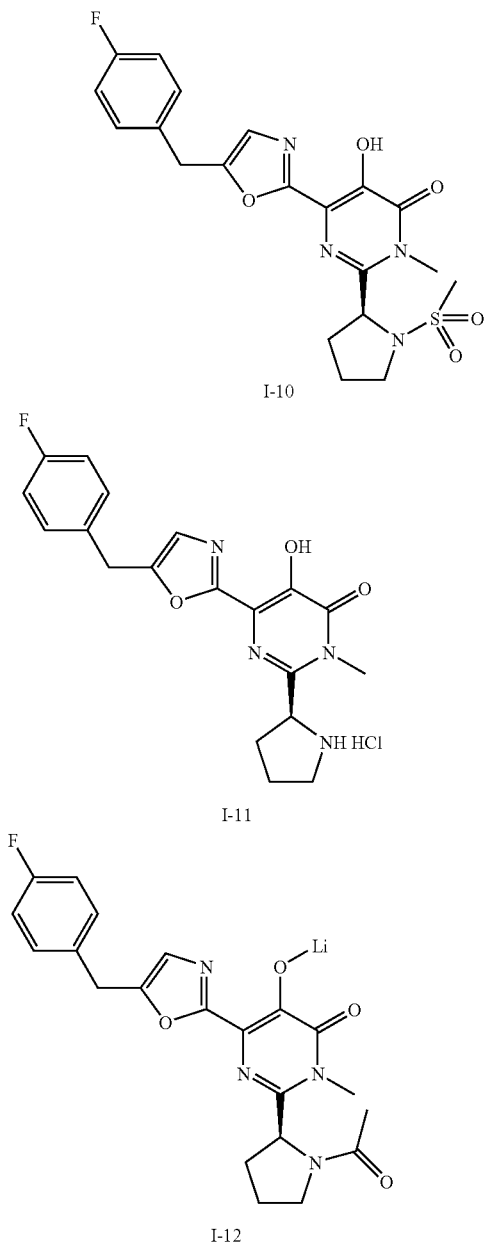

I-10

I-11

I-12

Step 1

Reaction was performed in accordance with the method described in Step 6 of Example 1 using Compound 10 obtained from Step 1 of Example 2 to give Compound 28 as colorless crystals.

Step 2

To a tetrahydrofuran (16 ml) suspension of Compound 28 (1.53 g, 3.04 mmol) was added (methoxycarbonylsulfamoyl) triethyl ammonium hydroxide (1.09 g, 4.56 mmol), and the mixture was allowed to react for 7 minutes at 150° C. under microwave radiation. The reaction solution was added with water, and extracted with ethylacetate. The extract was washed with water and saturated brine, and then dried over anhydrous sodium sulfate. A crude product obtained by distilling off the solvent under reduced pressure was subjected to silica gel chromatography. The fraction containing the target product obtained by eluting with ethyl acetate was concentrated under reduced pressure, to give Compound 29 (671 mg, 45% yield) as colorless crystals.

Step 3

Reaction was performed in accordance with the method described in Step 8 of Example 1 using Compound 29 (671 mg, 1.38 mmol) to give Compound 30 (341 mg, 67% yield) as an oily product.

Step 4

To a methylene chloride (3 ml) solution of Compound 30 (144 mg, 0.389 mmol) were added triethylamine (0.163 ml, 1.17 mmol) and methanesulfonyl chloride (0.075 ml, 0.973 mmol) under ice-cooling, and the mixture was stirred for 1 hour under room temperature. The reaction solution was added with 1N hydrochloric acid and extracted with ethyl acetate. The extract was washed with water and saturated brine, and then dried over anhydrous sodium sulfate. A crude product obtained by distilling off solvent under reduced pressure was dissolved in methanol (1.5 ml), added with 1N lithium hydroxide solution (1 ml), and stirred at room temperature for 14 hours. The reaction solution was added with 1N hydrochloric acid and water, and the precipitated crystals were collected by filtration to give Compound I-10 (81 mg, 46% yield) as colorless crystals.

Melting point: 155-157° C. Recrystallization solvent: diethyl ether

NMR (CDCl3) d: 1.89-1.97 (1H, m), 2.06-2.15 (2H, m), 2.39-2.52 (1H, m), 2.85 (3H, s), 3.59-3.66 (2H, m), 3.61 (3H, s), 4.06-4.08 (2H, m), 5.15-5.18 (1H, m), 6.99 (1H, brs), 7.00-7.06 (2H, m), 7.18-7.22 (2H, m).

Elemental analysis for $C_{20}H_{21}FN_4O_5S(H_2O)_{0.1}$

Calcd. (%): C, 53.35; H, 4.75; N, 12.44; S, 7.12; F, 4.22.

Found. (%): C, 53.50; H, 5.01; N, 11.85; S, 6.62; F, 3.96.

MS (positive FABMS): m/Z 499 (M+H)+.

In the same manner, Compounds I-11 and I-12 were obtained.

Compound I-11

Melting point: 234-236° C. Recrystallization solvent: ethyl acetate

NMR (DMSO-d6) d: 1.93-2.19 (3H, m), 2.33-2.45 (1H, m), 3.20-3.51 (2H, m), 3.52 (3H, s), 4.16 (2H, s), 4.90-4.97 (1H, m), 7.15-7.20 (2H, m), 7.20 (1H, s), 7.34-7.39 (2H, m), 8.79 (1H, bs), 10.10 (1H, bs).

Elemental analysis for $C_{19}H_{19}FN_4O_3(HCl)_{1.8}(H_2O)_{2.0}$

Calcd. (%): C, 48.34; H, 5.30; N, 11.87; Cl, 13.52; F, 4.02.

Found. (%): C, 47.60; H, 4.65; N, 11.49; Cl, 13.33; F, 4.44.

MS (positive FABMS): m/Z 371 (M+H)+, 741 (2M+H)+.

Compound I-12

Melting point: 300° C. or more Recrystallization solvent: methanol-water

NMR (DMSO-d6) d: 1.82-2.06 (3H, m), 1.88 (3H, s), 2.10-2.27 (1H, m), 3.43 (3H, s), 3.47-3.66 (2H, m), 4.03 (2H, s), 4.98-5.00 (1H, m), 6.82 (1H, s), 7.11-7.17 (2H, m), 7.32-7.38 (2H, m).

Elemental analysis for $C_{21}H_{20}FLiN_4O_4(H_2O)_{2.0}(MeOH)_{0.9}$

Calcd. (%): C, 54.43; H, 5.76; N, 11.59; Li, 1.44; F, 3.93.

Found. (%): C, 54.03; H, 4.83; N, 11.61; Li, 1.52; F, 3.98.

MS (positive FABMS): m/Z 419 (M+H)⁺, 425 (M+Li)⁺, 843 (2M+Li)⁺.

Example 8

[Formula 35]

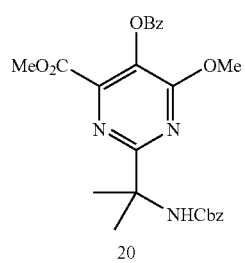
20

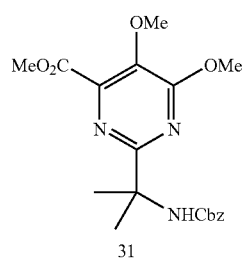
31

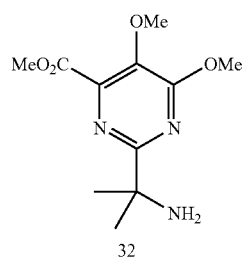
32

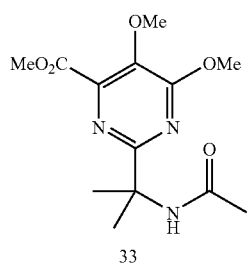
33

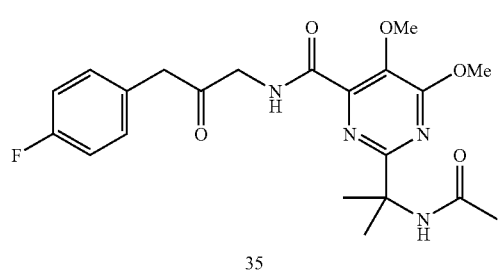
35

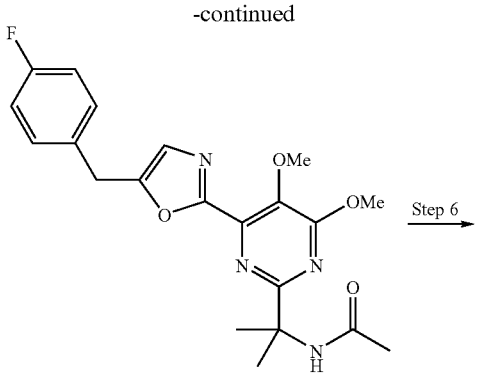
35

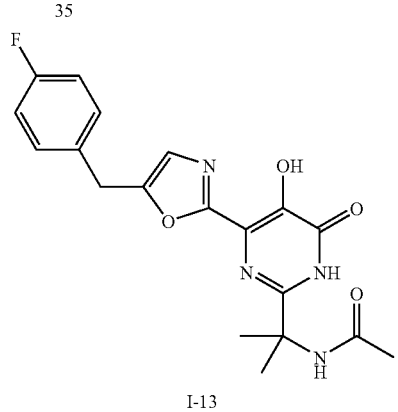
I-13

Step 1

Reaction was performed in accordance with the method described in Step 1 of Example 2 using Compound 20 (25.70 g, 53.60 mmol) obtained from Step 1 of Example 5 to give Compound 31 (20.80 g, 98% yield) as pale yellow oil.

Step 2

To a methanol (200 ml) solution of Compound 31 (9.98 g, 25.6 mmol) was added 10% palladium-carbon (1.0 g) under ice-cooling, and the mixture was stirred for 3 hours in hydrogen atmosphere at 1 atmospheric pressure. The reaction solution was filtered and the filtrate was distilled off under reduced pressure to give Compound 32 (6.27 g, 96% yield) as colorless oil.

Step 3

Reaction was performed in accordance with the method described in Step 5 of Example 3 using Compound 32 to give Compound 33 as a crude product.

Step 4

Reaction was performed in accordance with the method described in Step 6 of Example 1 using the crude product of Compound 33 to give Compound 34 as light brown crystals.

Step 5

Reaction was performed in accordance with the method described in Step 7 of Example 1 using Compound 34 (845 mg, 1.95 mmol) to give Compound 35 (121 mg, 15% yield) as an oily product.

Step 6

Compound 35 (119 mg, 0.287 mmol) was dissolved in methylene chloride (25 ml), added with aluminum chloride (1.72 g, 12.9 mmol), and allowed to react for 20 hours at room temperature. The reaction solution was added with 10% citric acid aqueous solution, and extracted with chloroform. The extract was washed with water, and then dried over anhydrous sodium sulfate. A crude product obtained by distilling off solvent under reduced pressure was recrystallized from acetone-diisopropyl ether to give Compound I-13 (34 mg, 31% yield) as light brown crystals.

Melting point: 118-120° C. Recrystallization solvent: acetone-diisopropyl ether

NMR (CDCl3) d: 1.72 (6H, s), 2.01 (3H, s), 4.11 (2H, s), 6.73 (1H, brs), 6.87 (1H, s), 7.02-7.08 (2H, m), 7.24-7.29 (2H, m), 12.30 (1H, brs).

Example 9

[Formula 36]

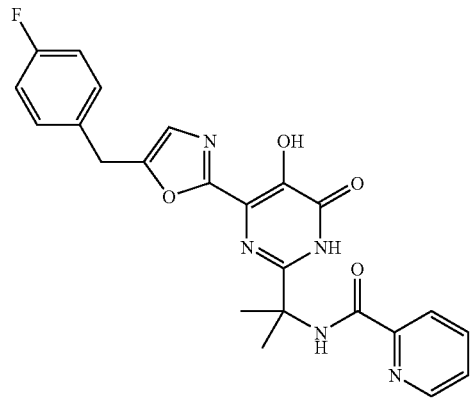

Step 1

Reaction was performed in accordance with the method of Step 7 of Example 1 using Compound 22 (2.10 g, 3.59 mmol) obtained from Step 3 of Example 5 to give Compound 36 (233 mg, 12% yield) as an oily product.

Step 2

Reaction was performed in accordance with the method of Step 8 of Example 1 using Compound 36 (233 mg, 0.399 mmol) to give Compound 37 (34 mg, 25% yield) as an oily product.

Step 3

To a methylene chloride (1.0 ml) solution of 2-picoline acid (13.1 mg, 0.106 mmol), 1-hydroxybenzotriazole (17.0 mg, 0.126 mmol) and 1-ethyl-3-(3-dimethylaminopropyl) carbodiimide hydrochloric acid salt (24.2 mg, 0.126 mmol) was added diisopropylethylamine (0.0219 ml, 0.126 mmol) at room temperature, and the mixture was stirred for 30 minutes. This reaction solution was added to a methylene chloride (0.5 ml) solution of Compound 37 (33.3 mg, 0.0967 mmol) under ice-cooling, and stirred at room temperature for 1 hour. The reaction solution was added with 0.5N hydrochloric acid, and extracted with chloroform. The extract was washed with saturated sodium bicarbonate water and saturated brine, and then dried over anhydrous sodium sulfate. A crude product obtained by distilling off solvent under reduced pressure was recrystallized from methanol-diethyl ether to give Compound I-14 (25.3 mg, 58% yield) as pale yellow crystals.

Melting point: 205-207° C. Recrystallization solvent: methanol-diethyl ether

NMR (CDCl3) d: 1.74 (6H, s), 2.01 (3H, s), 3.69 (3H, s), 4.18 (2H, s), 6.11 (1H, brs), 6.70-7.06 (2H, m), 7.19-7.23 (2H, m), 7.62 (1H, s).

Example 10
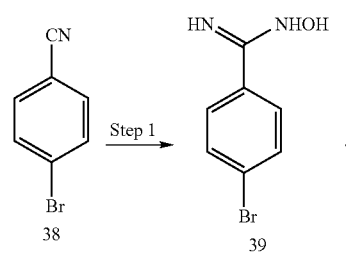
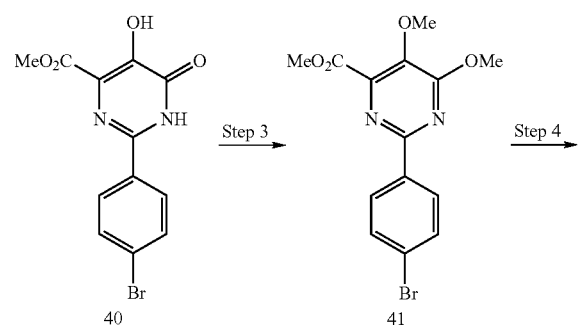
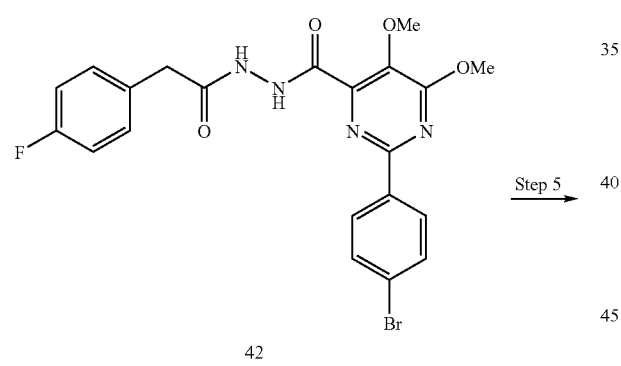
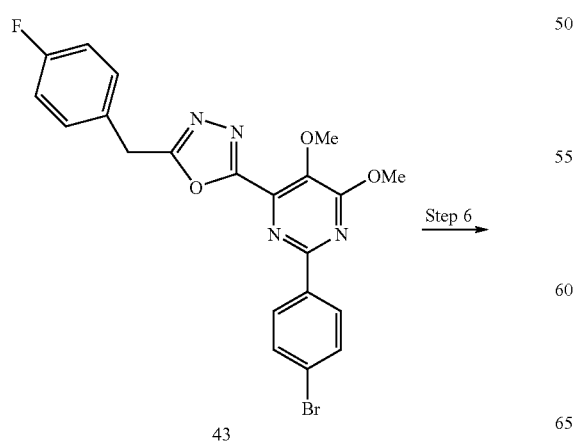
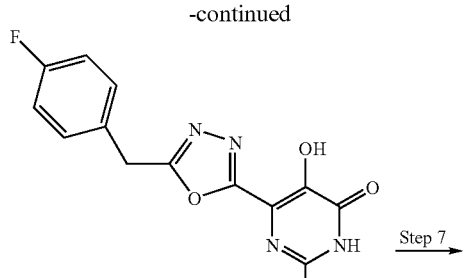
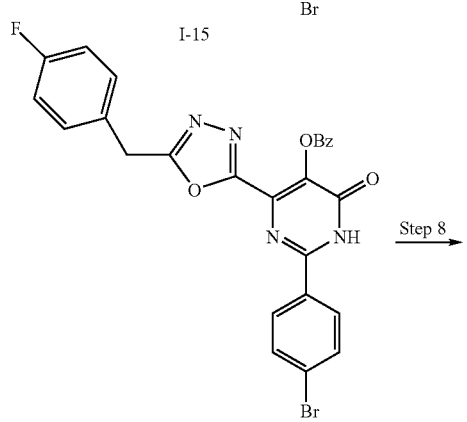
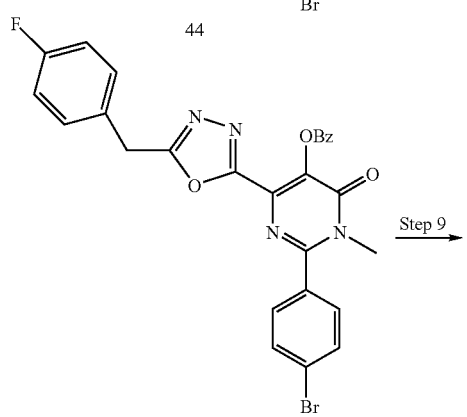
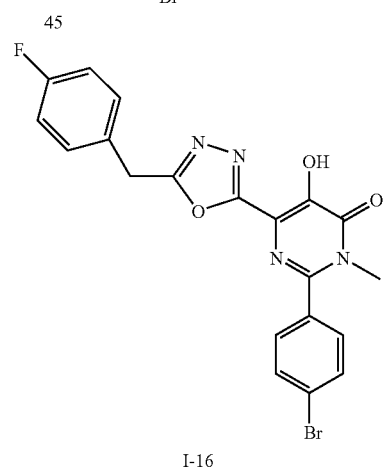

Step 1

Reaction was performed in accordance with the method of Step 1 of Example 1 using 4-bromobenzonitrile (51.44 g, 282.6 mmol) to give Compound 39 (60.38 g, 99% yield) as colorless crystals.

Step 2

Reaction was performed in accordance with the method of Step 2 of Example 1 using Compound 39 (60.38 g, 280.8 mmol) to give Compound 40 (54.25 g, 59% yield) as light brown crystals.

Step 3

To a N,N-dimethylformamide (550 ml) solution of Compound 40 (54.25 g, 166.9 mmol) were added potassium carbonate (69.19 g, 500.6 mmol) and methyl iodide (32.0 ml, 514 mmol) at room temperature, and the mixture was stirred for 18 hours. After stirring for another 1 hour at 80° C., the reaction solution was added with water (200 ml) and 2N hydrochloric acid (200 ml) under ice-cooling, and extracted twice with ethyl acetate. The extract was washed with saturated sodium bicarbonate water (100 ml), water (100 ml) and saturated brine, and then dried over anhydrous sodium sulfate. A crude product obtained by distilling off the solvent under reduced pressure was subjected to silica gel chromatography. A fraction of objective product resulting from elution with hexane-ethyl acetate (2:1 v/v) was concentrated under reduced pressure to give Compound 41 (33.2 g, 56% yield) as pale yellow crystals.

Step 4

Reaction was performed in accordance with the method of Step 2 of Example 2 using Compound 41 (15.00 g, 42.47 mmol) to give Compound 42 (10.96 g) as a crude product.

Step 5

Reaction was performed in accordance with the method of Step 3 of Example 2 using the crude product of Compound 42 (10.94 g) to give Compound 43 (6.11 g) as colorless crystals.

Step 6

Reaction was performed in accordance with the method of Step 8 of Example 1 using Compound 43 (2.0 g, 4.24 mmol) to give Compound I-15 (2.5 g) as a crude product. This was then washed with methanol to give Compound I-15 (94 mg) as colorless crystals.

Melting point: >250° C. Recrystallization solvent: methanol

NMR (DMSO-d6) d: 4.45 (2H, s), 7.22-7.28 (2H, m), 7.45-7.49 (2H, m), 7.79 (2H, d, J=9.2 Hz), 8.03 (2H, d, J=9.2 Hz).

Elemental analysis for $C_{19}H_{12}BrFN_4O_3(H_2O)_{0.2}$

Calcd. (%): C, 51.07; H, 2.80; N, 12.54; Br, 17.88; F, 4.25.

Found. (%): C, 51.13; H, 2.71; N, 12.63; Br, 17.81; F, 4.04.

Step 7

Reaction was performed in accordance with the method of Step 3 of Example 1 using the crude product of Compound I-15 (2.5 g) to give Compound 44 (2.01 g) as colorless crystals.

Step 8

Reaction was performed in accordance with the method of Step 4 of Example 1 using Compound 44 (1.98 g, 3.62 mmol) to give Compound 45 (232 mg, 11% yield) as colorless crystals.

Step 9

To a 1,4-dioxane (3 ml) solution of Compound 45 (80 mg, 0.14 mmol) was added 1N sodium hydroxide aqueous solution (0.5 ml), and the mixture was stirred for 1 hour at 100° C. The reaction solution was added with an aqueous solution of saturated ammonium chloride, and extracted with ethyl acetate. The extract was washed with water and saturated brine, and then dried over anhydrous sodium sulfate. A crude product obtained by distilling off solvent under reduced pressure was recrystallized from ethanol to give Compound I-16 (29 mg, 44% yield) as colorless crystals.

Melting point: 143-153° C. Recrystallization solvent: ethanol

NMR (DMSO-d6) d: 4.34 (2H, s), 7.10-7.22 (2H, m), 7.31-7.42 (2H, m), 7.49-7.57 (2H, m), 7.66-7.75 (2H, m).

Example 11

[Formula 38]

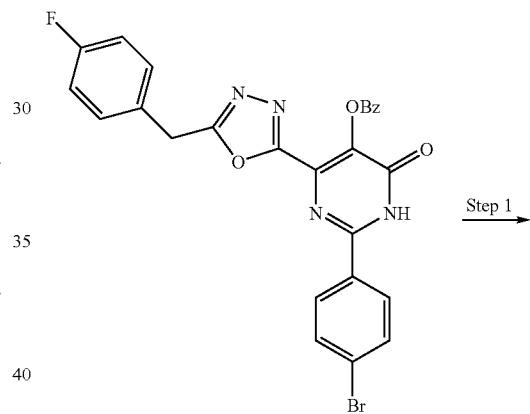

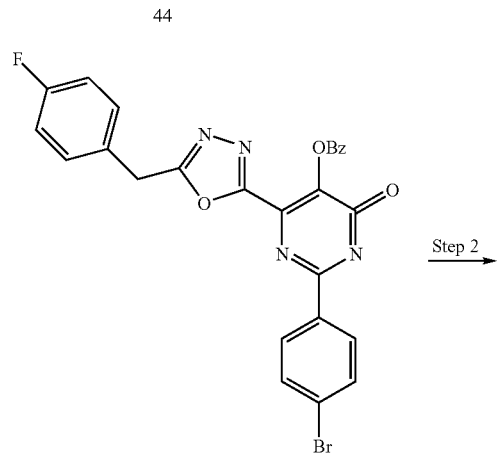

46

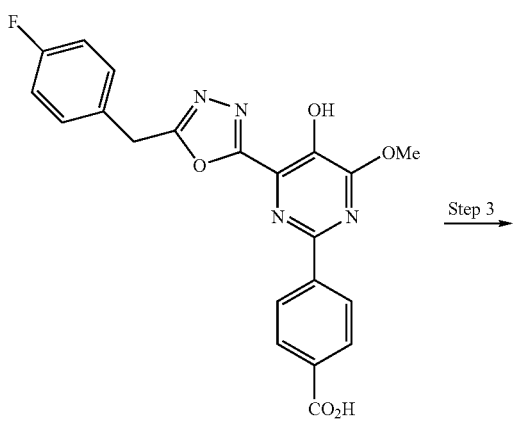

47

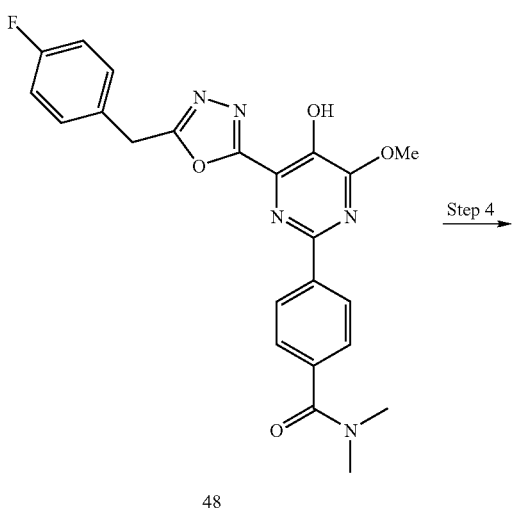

48

Step 1

Reaction was performed in accordance with the method of Step 8 of Example 10 using Compound 44 (1.98 g, 3.62 mmol) obtained from Step 7 of Example 10 to give Compound 46 (940 mg, 46% yield) as colorless crystals.

Step 2

To a dimethylsulfoxide (8 ml) suspension of Compound 46 (660 mg, 1.17 mmol), palladium acetate (II) (53 mg, 0.23 mmol) and 1,3-bis(diphenylphosphino)propane (121 mg, 0.29 mmol), triethylamine (1.64 ml, 11.7 mmol) and water (2 ml) were sequentially added at room temperature, and the mixture was stirred in carbon monoxide atmosphere at 1 atmospheric pressure for 1 hour at room temperature and for 17 hours at 70° C. The reaction solution was added with an aqueous solution of saturated ammonium chloride, and extracted with ethyl acetate. The extract was washed with water and saturated brine, and then dried over anhydrous sodium sulfate. A crude product obtained by distilling off solvent under reduced pressure was washed with ethyl acetate and methanol to give Compound 47 (381 mg, 77% yield) as colorless crystals.

Step 3

Reaction was performed in accordance with the method of Step 3 of Example 9 using Compound 47 (380 mg, 0.90 mmol) to give Compound 48 (115 mg, 28% yield) as colorless crystals.

Step 4

Reaction was performed in accordance with the method of Step 8 of Example 1 using Compound 48 (110 mg, 0.25 mmol) to give Compound I-17 (25 mg, 23% yield) as pale yellow crystals.

Melting point: 211-213° C. Recrystallization solvent: ethyl acetate-hexane

NMR (DMSO-d6) d: 2.92 (3H, s), 3.01 (3H, s), 4.41 (2H, s), 7.18-7.24 (2H, m), 7.41-7.45 (2H, m), 7.54 (2H, d, J=8.5 Hz), 8.09 (2H, d, J=8.5 Hz), 8.19-8.26 (1H, m).

Example 12

[Formula 39]

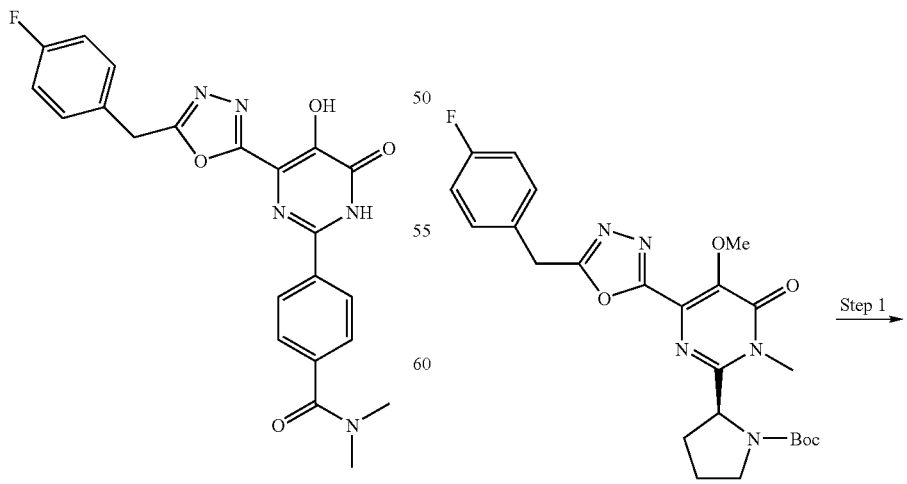

I-17    12

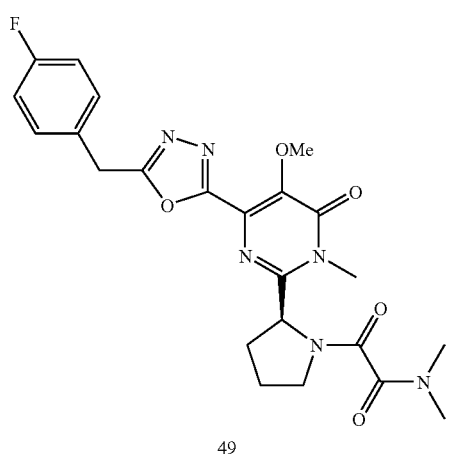

49

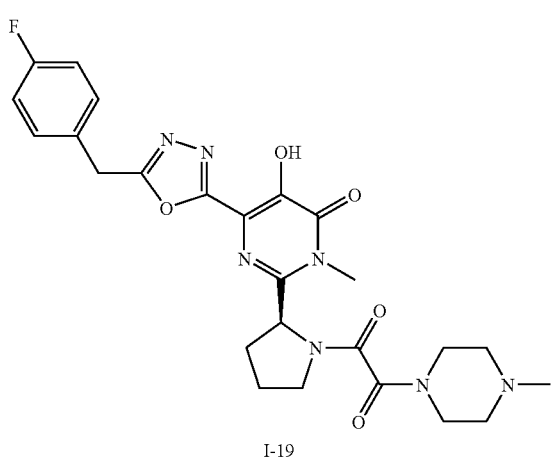

I-18

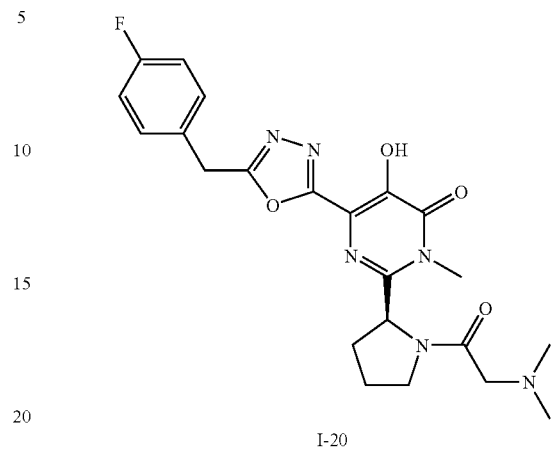

I-20

Step 1
Reaction was performed in accordance with the method of Step 4 of Example 2 using Compound 12 obtained in Step 3 of Example 2 to give Compound 49 as a crude product.

Step 2
Reaction was performed in accordance with the method of Step 5 of Example 2 using the crude product of Compound 49 to give Compound I-18 as a crude product. This was then recrystallized from isopropanol to give Compound I-18 as colorless crystals.

Melting point: 252-255° C. Recrystallization solvent: isopropanol

NMR (CDCl3) d: 1.91-2.26 (3H, m), 2.36-2.49 (1H, m), 2.67 (3H, s), 2.90 (3H, s), 3.61-3.84 (2H, m), 3.73 (3H, s), 4.21 (1H, d, J=16.2 Hz), 4.38 (1H, d, J=16.2 Hz), 5.14-5.18 (1H, m), 7.05-7.11 (2H, m), 7.26-7.32 (2H, m), 9.45 (1H, brs).

MS (positive FABMS): m/Z 471 (M+H)$^+$, 941 (2M+H)$^+$.

In a similar manner, Compounds I-19 and I-20 were obtained.

Compound I-19

Melting point: 194-196° C. Recrystallization solvent: isopropanol-diethyl ether

NMR (CDCl3) d: 1.95-2.43 (8H, m), 2.33 (3H, s), 3.45-3.87 (6H, m), 3.73 (3H, s), 4.32 (2H, s), 5.15-5.19 (1H, m), 7.03-7.09 (2H, m), 7.33-7.37 (2H, m).

MS (positive FABMS): m/Z 526 (M+H)$^+$.

Compound I-20

Melting point: 108-110° C. Recrystallization solvent: isopropanol-diethyl ether

NMR (CDCl3) d: 1.90-2.35 (4H, m), 2.28 (6H, s), 3.14 (2H, d, J=6.6 Hz), 3.66-3.90 (2H, m), 3.74 (3H, s), 4.28 (2H, d, J=6.0 Hz), 5.14-5.17 (1H, m), 7.04-7.09 (2H, m), 7.30-7.34 (2H, m).

MS (positive FABMS): m/Z 457 (M+H)$^+$, 913 (2M+H)$^+$.

Example 13

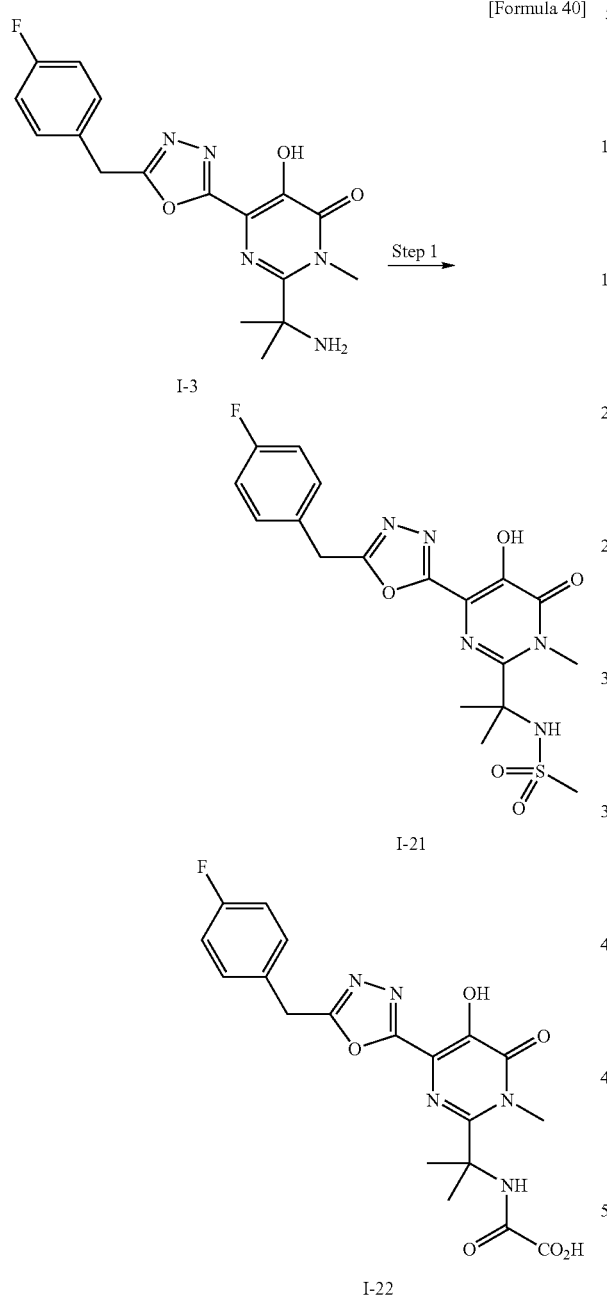

Step 1

Reaction was performed in accordance with the method of Step 5 of Example 3 using Compound I-3 obtained from Step 4 of Example 3 to give Compound I-21 as colorless crystals.

Melting point: 236-239° C. Recrystallization solvent: ethyl acetate

NMR (CDCl3) d: 1.79 (6H, s), 3.03 (3H, s), 3.92 (3H, s), 4.30 (2H, s), 7.03-7.08 (2H, m), 7.33-7.36 (2H, m), 7.51 (1H, s).

MS (positive FABMS): m/Z 438 (M+H)$^+$, 875 (2M+H)$^+$.

In a similar manner, Compound I-22 was obtained.

Compound I-22

Melting point: 236-239° C. Recrystallization solvent: methanol-water

NMR (DMSO-d6) d: 1.64 (6H, s), 3.52 (3H, s), 4.38 (2H, s), 7.16-7.22 (2H, m), 7.40-7.44 (2H, m), 9.38 (1H, s), 10.65 (1H, brs).

MS (positive FABMS): m/Z 432 (M+H)$^+$, 863 (2M+H)$^+$.

Example 14

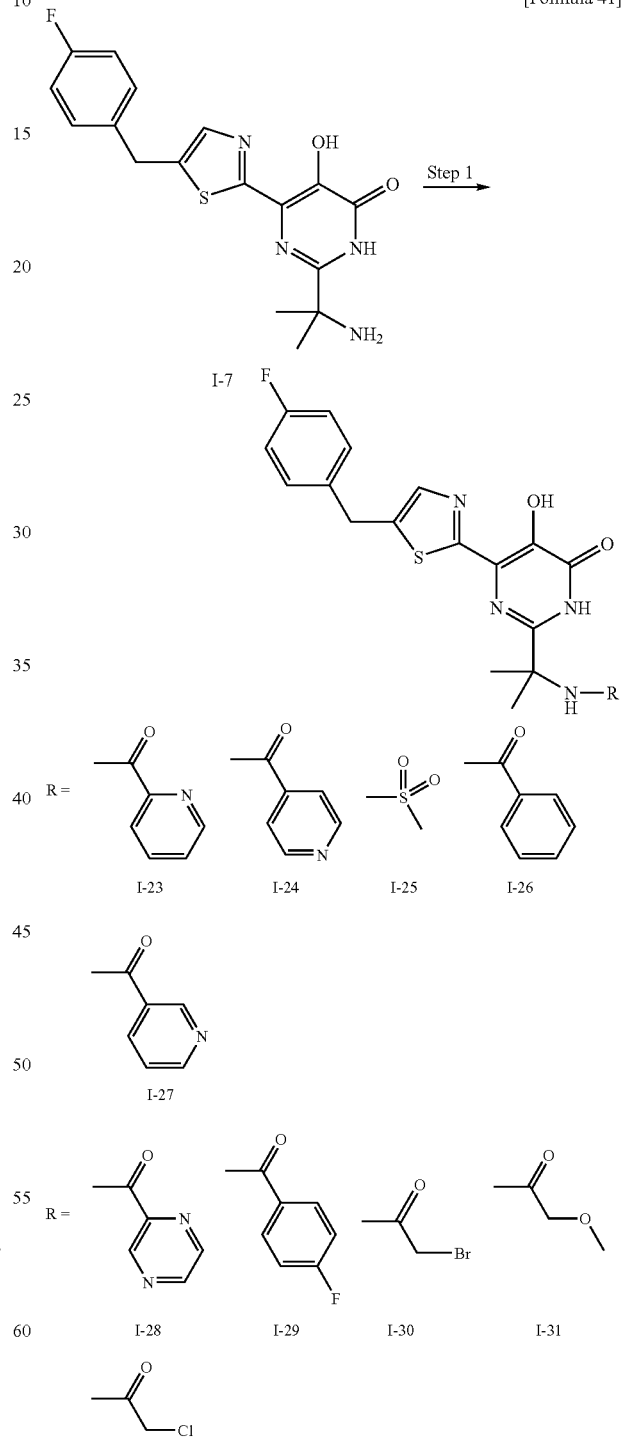

Step 1

Reaction was performed in accordance with the method of Step 3 of Example 9 using Compound I-7 obtained from Step 6 of Example 5 to give Compound I-23 as pale yellow crystals.

Melting point: >300° C. Recrystallization solvent: tetrahydrofuran-methanol

NMR (CDCl3) d: 1.84 (6H, s), 4.20 (2H, s), 7.01-7.07 (2H, m), 7.21-7.27 (2H, m), 7.47-7.51 (1H, m), 7.87-7.93 (1H, m), 8.19 (1H, d, J=7.5 Hz), 8.54 (1H, d, 3=4.5 Hz), 8.64 (1H, s), 11.40 (1H, brs).

Elemental analysis for $C_{23}H_{20}FN_5O_3S$

Calcd. (%): C, 59.34; H, 4.33; N, 15.04; F, 4.08; S, 6.81.
Found. (%): C, 59.15; H, 4.14; N, 14.78; F, 3.88; S, 6.80.
MS (positive FABMS): m/Z 466 (M+H)$^+$, 931 (2M+H)$^+$.

In a similar manner, Compounds I-24 to I-32 were obtained.

Compound I-24

Melting point: 245-248° C. Recrystallization solvent: methanol-diisopropyl ether NMR (CDCl3) d: 1.79 (6H, s), 4.21 (2H, s), 7.05 (2H, t, J=8.4 Hz), 7.22-7.26 (2H, m), 7.39 (1H, s), 7.66 (1H, s), 7.83 (2H, d, J=6.0 Hz), 8.65 (2H, d, J=6.3 Hz), 12.94 (1H, brs).

MS (positive FABMS): m/Z 466 (M+H)$^+$, 931 (2M+H)$^+$.

Compound I-25

Melting point: 134-136° C. Recrystallization solvent: methanol-diisopropyl ether NMR (CDCl3) d: 1.76 (6H, s), 3.05 (3H, s), 4.18 (2H, s), 6.17 (1H, s), 7.00-7.06 (2H, m), 7.18-7.26 (2H, m), 7.62 (1H, s), 11.95 (1H, brs).

MS (positive FABMS): m/Z 439 (M+H)$^+$.

Compound I-26

Melting point: 281-283° C. Recrystallization solvent: methanol-diisopropyl ether NMR (CDCl3) d: 1.80 (6H, s), 4.20 (2H, s), 7.05 (2H, t, J=8.4 Hz), 7.15-7.24 (2H, m), 7.30-7.34 (2H, m), 7.64 (1H, s), 7.90 (2H, d, J=6.0 Hz), 12.60 (1H, brs).

Elemental analysis for $C_{24}H_{21}FN_4O_3S$

Calcd. (%): C, 62.06; H, 4.56; N, 12.06; F, 4.09; S, 6.90.
Found. (%): C, 61.77; H, 4.45; N, 11.97; F, 3.96; S, 6.93.
MS (positive FABMS): m/Z 465 (M+H)$^+$, 929 (2M+H)$^+$.

Compound I-27

Melting point: 250-251° C. Recrystallization solvent: methanol-diisopropyl ether NMR (CDCl3) d: 1.78 (6H, s), 4.20 (2H, s), 7.05 (2H, t, J=8.7 Hz), 7.21-7.26 (2H, m), 7.63 (1H, s), 7.75 (1H, s), 8.31 (1H, d, J=7.8 Hz), 8.54 (1H, d, J=4.2 Hz), 12.93 (1H, brs).

MS (positive FABMS): m/Z 466 (M+H)$^+$, 931 (2M+H)$^+$.

Compound I-28

Melting point: 293° C. Recrystallization solvent: methanol-diisopropyl ether

NMR (DMSO-d6) d: 1.71 (6H, s), 4.31 (2H, s), 7.20 (2H, d, J=8.70 Hz), 7.38-7.42 (2H, m), 7.93 (1H, s), 8.70 (1H, m), 8.94 (1H, d, J=2.70 Hz), 9.14-9.17 (2H, m), 12.80 (1H, brs).

Compound I-29

Melting point: 288-290° C. Recrystallization solvent: methanol-diisopropyl ether NMR (CDCl3) d: 1.77 (6H, s), 4.21 (2H, s), 6.96 (2H, t, J=8.70 Hz), 7.02-7.13 (2H, m), 7.13 (1H, s), 7.22-7.26 (1H, m), 7.65 (1H, s), 7.92 (2H, dd, J=8.70 Hz, 5.40 Hz), 12.80 (1H, brs).

Elemental analysis for $C_{24}H_{20}F_2N_4O_3S$

Calcd. (%): C, 59.74; H, 4.18; N, 11.61; F, 7.87; S, 6.65.
Found. (%): C, 59.81; H, 4.33; N, 11.42; F, 7.52; S, 6.38.
MS (positive FABMS): m/Z 483 (M+H)$^+$, 965 (2M+H)$^+$.

Compound I-30

Melting point: 208° C. Recrystallization solvent: methanol-diisopropyl ether

NMR (CDCl3) d: 1.74 (3H, s), 1.76 (3H, s), 3.90 (1H, s), 4.14 (1H, s), 4.19 (2H, s), 7.02 (2H, m), 7.16 (2H, m), 7.70 (2H, s), 12.40 (1H, brs).

MS (positive FABMS): m/Z 481 (M+H)$^+$.

Compound I-31

Melting point: 258-260° C. Recrystallization solvent: methanol-diisopropyl ether NMR (CDCl3) d: 1.73 (6H, s), 3.42 (3H, s), 3.89 (2H, s), 4.19 (2H, s), 7.01-7.08 (2H, m), 7.20-7.24 (2H, m), 7.63 (1H, s), 11.60 (1H, brs).

MS (positive FABMS): m/Z 433 (M+H)$^+$, 865 (2M+H)$^+$.

Compound I-32

Melting point: 114-116° C. Recrystallization solvent: methanol

NMR (CDCl3) d: 1.76 (6H, s), 4.08 (2H, s), 4.19 (2H, s), 7.03 (2H, t, J=8.71 Hz), 7.20-7.24 (2H, m), 7.62 (1H, s), 7.72 (1H, s), 12.54 (1H, brs).

MS (positive FABMS): m/Z 437 (M+H)$^+$, 873 (2M+H)$^+$.

Example 15

[Formula 42]

67

-continued

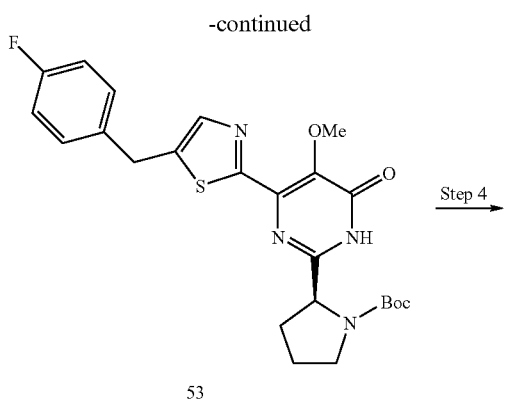

53

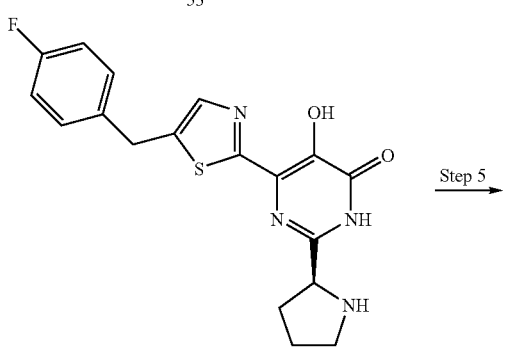

54

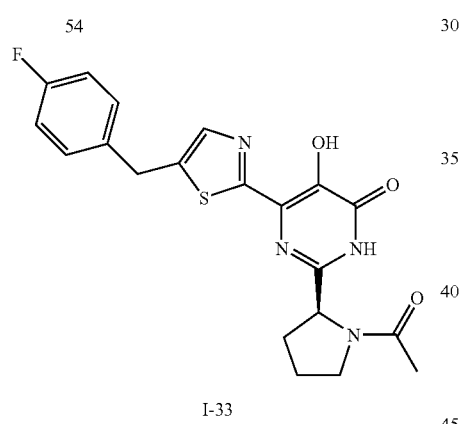

I-33

Step 1

Reaction was performed in accordance with the method described in Step 1 of Example 2 using Compound 50 synthesized in accordance with the method described in Patent (WO 03/035077) to give Compound 51 as a crude product.

Step 2

Reaction was performed in accordance with the method described in Step 6 of Example 1 using the crude product of Compound 51 to give Compound 52 as a crude product.

Step 3

Reaction was performed in accordance with the method described in Step 4 of Example 5 using the crude product of Compound 52 to give Compound 53 as a crude product.

Step 4

Reaction was performed in accordance with the method described in Step 8 of Example 1 using the crude product of Compound 53 to give Compound 54 as a crude product.'

68

Step 5

Reaction was performed in accordance with the method described in Step 5 of Example 3 using the crude product of Compound 54 to give Compound I-33 as pale yellow crystals.

Melting point: 138-140° C. Recrystallization solvent: ethyl acetate-diethyl ether NMR (CDCl3) d: 1.90-2.30 (3H, m), 2.14 (3H, s), 2.85-2.95 (1H, m), 3.46-3.58 (2H, m), 4.18 (2H, s), 5.06-5.09 (1H, m), 7.01-7.06 (2H, m), 7.19-7.24 (2H, m), 7.63 (1H, s).

MS (positive FABMS): m/Z 415 (M+H)$^+$, 437 (M+Na)$^+$.

Example 16

[Formula 43]

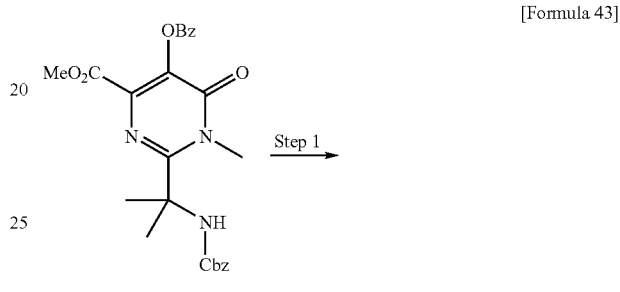

13

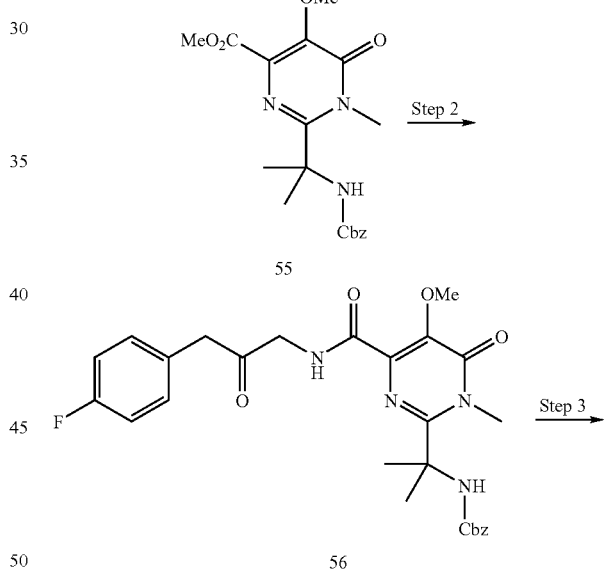

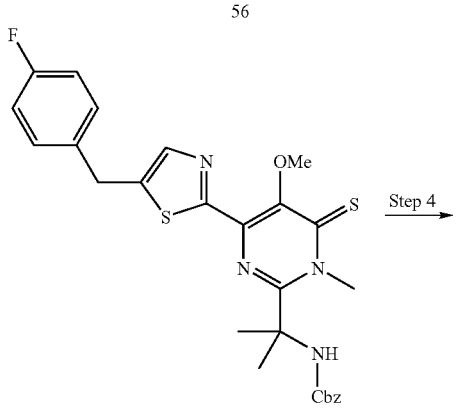

57

-continued

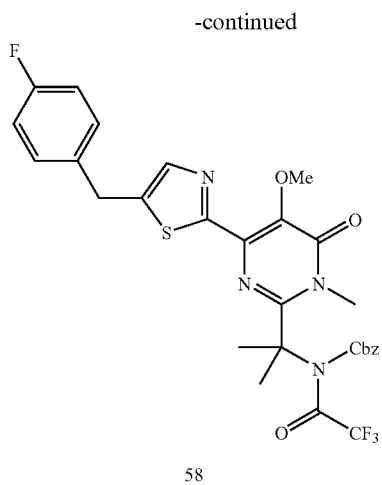
58

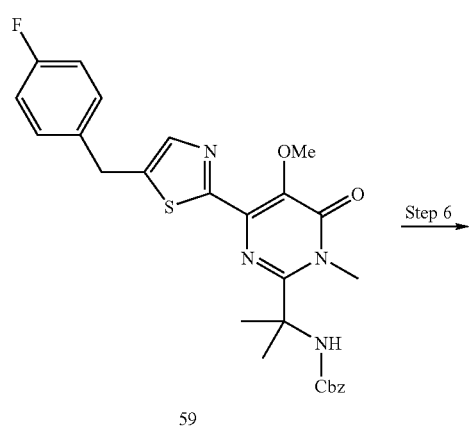
59

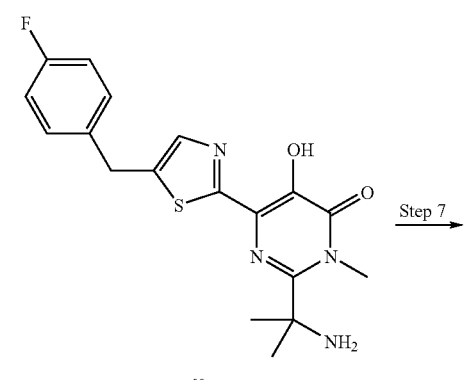
60

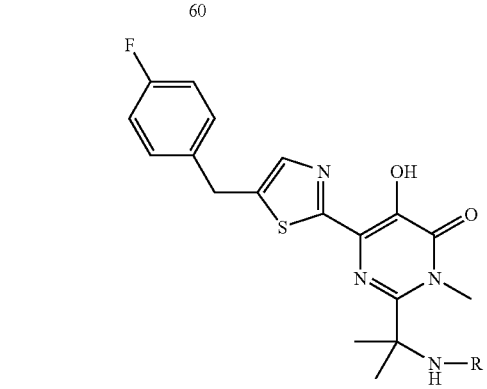

-continued

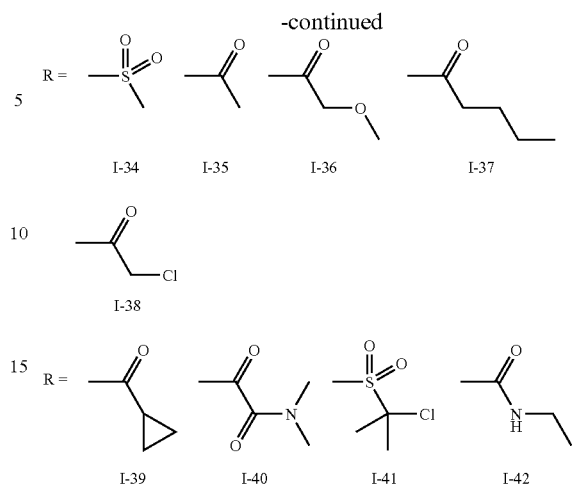

Step 1
Reaction was performed in accordance with the method described in Step 1 of Example 2 using Compound 13 described in (WO 03/035077) to give Compound 55.

Step 2
Reaction was performed in accordance with the method described in Step 6 of Example 1 using Compound 55 to give Compound 56.

Step 3
To a toluene solution of Compound 56 (1.27 g, 2.42 mmol) was added Lawson's reagent (1.96 g, 4.84 mmol) at room temperature, and the mixture was refluxed for 1.5 hours under heating. The reaction solution was added with 1N hydrochloric acid (25 ml) under ice-cooling, and extracted with ethyl acetate. The extract was washed with water and saturated brine, and then dried over anhydrous sodium sulfate. A crude product obtained by distilling off the solvent under reduced pressure was subjected to silica gel chromatography. A fraction of objective product resulting from elution with hexane-ethyl acetate (1:1 v/v) was concentrated under reduced pressure to give Compound 57 (615 mg) and Compound 59 (338 mg) as crude products.

Step 4
To an acetonitrile solution of the crude product (542 mg) of Compound 57 was added trifluoroacetic anhydride (2.8 ml, 20.2 mmol) at room temperature, and stirred at 80° C. for 45 minutes. The reaction solution was cooled to room temperature, and then added with 10% sodium carbonate aqueous solution (30 ml), stirred for 10 minutes, and extracted with ethyl acetate. The extract was washed with saturated brine, and dried over anhydrous sodium sulfate. The solvent was distilled off under reduced pressure to give a crude product of Compound 58.

Step 5
To a methanol (20 ml) suspension of the crude product of Compound 58 was added 1N lithium hydroxide solution (2 ml) at room temperature, and the mixture was stirred for 5 minutes. The reaction solution was added with 10% citric acid aqueous solution, and extracted with ethyl acetate. The extract was washed with saturated brine, and then dried over anhydrous sodium sulfate. A crude product obtained by distilling off the solvent under reduced pressure was subjected to silica gel chromatography. The fraction of target product obtained by elution with ethyl acetate was distilled off under reduced pressure to give Compound 59 (348 mg) as yellow oil (total 686 mg, 54% overall yield).

Step 6

Reaction was performed in accordance with the method described in Step 8 of Example 1 using Compound 59 (349 mg, 0.667 mmol) to give Compound 60 (150 mg, 60% yield).

Step 7

Reaction was performed in accordance with the method described in Step 5 of Example 3 using Compound 60 (150 mg, 0.401 mmol) to give Compound I-34 (86 mg, 47% yield) as pale yellow crystals.

Melting point: 137-139° C. Recrystallization solvent: methanol-isopropanol

NMR (CDCl3) d: 1.83 (6H, s), 3.06 (3H, s), 3.88 (3H, s), 4.17 (2H, s), 5.06 (1H, s), 7.00-7.06 (2H, m), 7.20-7.23 (2H, m), 7.61 (1H, s).

Elemental analysis for $C_{19}H_{21}FN_4O_4S_2(H_2O)_{0.4}(MeOH)_{0.6}$

Calcd. (%): C, 49.15; H, 5.09; N, 11.70; S, 13.39; F, 3.97.
Found. (%): C, 49.14; H, 5.09; N, 11.50; S, 13.50; F, 3.83.

In a similar manner, Compounds I-35 to I-42 were obtained.

Compound I-35

Melting point: 205-207° C. Recrystallization solvent: methanol-diethyl ether

NMR (CDCl3) d: 1.74 (6H, s), 2.01 (3H, s), 3.69 (3H, s), 4.18 (2H, s), 6.11 (1H, brs), 6.70-7.06 (2H, m), 7.19-7.23 (2H, m), 7.62 (1H, s).

Compound I-36

Melting point: 200-201° C. Recrystallization solvent: methanol-isopropanol

NMR (CDCl3) d: 1.78 (6H, s), 3.41 (3H, s), 3.66 (3H, s), 3.84 (2H, s), 4.18 (2H, s), 7.00-7.05 (2H, m), 7.20-7.23 (2H, m), 7.63 (1H, s).

Elemental analysis for $C_{21}H_{23}FN_4O_4S(H_2O)_{0.8}$

Calcd. (%): C, 54.72; H, 5.38; N, 12.16; S, 6.96; F, 4.12.
Found. (%): C, 54.67; H, 5.54; N, 12.17; S, 7.13; F, 4.01.

Compound I-37

Melting point: 271-274° C. Recrystallization solvent: methanol-isopropanol

NMR (CDCl3) d: 0.93 (3H, t, J=7.2 Hz), 1.57-1.66 (4H, m), 1.73 (6H, s), 2.16 (2H, t, J=7.2 Hz), 3.67 (3H, s), 4.17 (2H, s), 5.92 (1H, s), 7.00-7.05 (2H, m), 7.21-7.22 (2H, m), 7.60 (1H, s).

Elemental analysis for $C_{23}H_{27}FN_4O_3S(H_2O)_{1.0}$

Calcd. (%): C, 57.97; H, 6.13; N, 11.76; S, 6.73; F, 3.99.
Found. (%): C, 57.87; H, 5.48; N, 11.91; S, 6.75; F, 3.80.

Compound I-38

Melting point: 224-227° C. Recrystallization solvent: methanol-isopropanol

NMR (CDCl3) d: 1.83 (6H, s), 3.67 (3H, s), 4.03 (2H, s), 4.18 (2H, s), 7.00-7.06 (2H, m), 7.19-7.24 (2H, m), 7.61 (1H, s), 7.73 (1H, bs).

MS (positive FABMS): m/Z 451 (M+H)+, 901 (2M+H)+.

Compound I-39

Melting point: 261-262° C. Recrystallization solvent: methanol-isopropanol

NMR (CDCl3) d: 0.71-0.76 (2H, m), 0.87-0.92 (2H, m), 1.32-1.39 (1H, m), 1.73 (6H, s), 3.69 (3H, s), 4.16 (2H, s), 6.05 (1H, s), 6.99-7.05 (2H, m), 7.17-7.21 (2H, m), 7.59 (1H, s).

Elemental analysis for $C_{22}H_{23}FN_4O_3S$

Calcd. (%): C, 59.71; H, 5.24; N, 12.66; S, 7.25; F, 4.29.
Found. (%): C, 59.59; H, 5.26; N, 12.62; S, 7.24; F, 4.12.

Compound I-40

Melting point: 226-227° C. Recrystallization solvent: methanol-isopropanol

NMR (CDCl3) d: 1.76 (6H, s), 3.02 (3H, s), 3.34 (3H, s), 3.64 (3H, s), 4.18 (2H, s), 7.00-7.05 (2H, m), 7.18-7.23 (2H, m), 7.61 (1H, s), 7.88 (1H, bs).

Elemental analysis for $C_{22}H_{24}FN_5O_4S(HCl)_{0.1}(H_2O)_{0.4}$

Calcd. (%): C, 54.55; H, 5.18; N, 14.46; S, 6.62; Cl, 0.73; F, 3.92.
Found. (%): C, 54.56; H, 5.03; N, 14.34; S, 6.61; Cl, 0.55; F, 3.74.

Compound I-41

Melting point: 185-188° C. Recrystallization solvent: methanol-isopropanol

NMR (CDCl3) d: 1.95 (6H, s), 3.85 (3H, s), 4.17 (2H, s), 5.66 (1H, s), 7.00-7.06 (2H, m), 7.19-7.22 (2H, m), 7.60 (1H, s).

MS (positive FABMS): m/Z 515 (M+H)+.

Compound I-42

Melting point: 240-241° C. Recrystallization solvent: methanol-diethyl ether

NMR (CDCl3) d: 1.06 (3H, t, J=7.2 Hz), 1.70 (6H, s), 3.13 (2H, q, J=7.2 Hz), 3.77 (3H, s) 4.17 (2H, s), 4.99 (1H, bs), 7.00-7.06 (2H, m), 7.18-7.22 (2H, m), 7.59 (1H, s).

MS (positive FABMS): m/Z 446 (M+H)+, 891 (2M+H)+.

Example 17

[Formula 44]

-continued

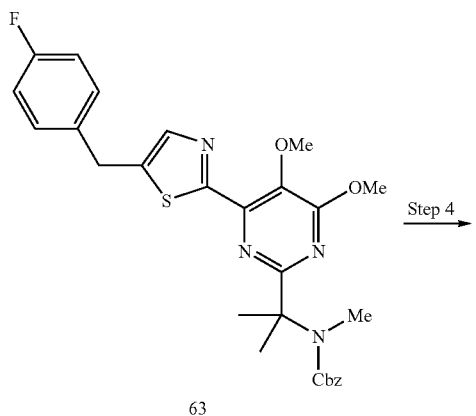

63

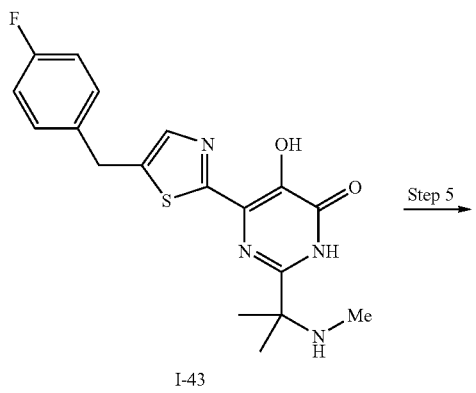

I-43

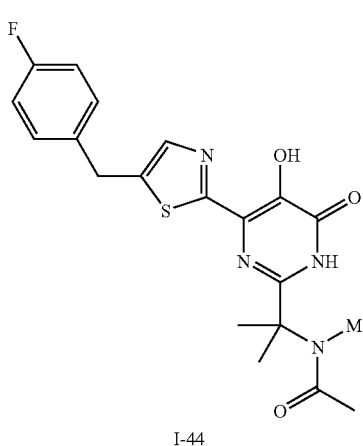

I-44

-continued

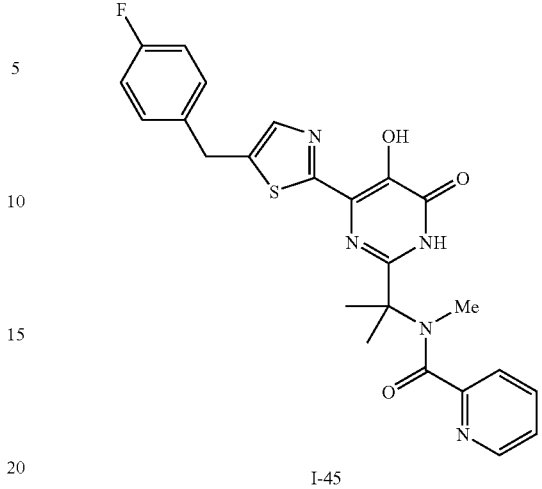

I-45

Step 1

To a dimethylformamide-tetrahydrofuran (1:10, v/v, 50 ml) suspension of sodium hydride (60% oil suspension, 1.54 g, 38.5 mmol), was added a dimethylformamide-tetrahydrofuran solution (1:10, v/v, 10 ml) of Compound 31 (3.00 g, 7.70 mmol) obtained from Step 1 of Example 8 and methyl iodide (15 ml, 241 mmol) at room temperature, and the mixture was refluxed under heating for 2 hours at 70° C. The reaction solution was added with an aqueous solution of saturated ammonium chloride (70 ml), and extracted three times with ethyl acetate (70 ml). The extract was washed with water (100 ml), and dried over anhydrous sodium sulfate. The solvent was distilled off under reduced pressure to give Compound 61 (2.59 g, 83% yield) as yellow oil.

Step 2

Reaction was performed in accordance with the method described in Step 3 of Example 5 using Compound 61 (2.40 g, 6.16 mmol) to give Compound 62 as a crude product.

Step 3

Reaction was performed in accordance with the method described in Step 4 of Example 5 using the crude product of Compound 62 to give Compound 63 (2.27 g, 69% yield) as brown oil.

step 4

To an acetonitrile (70 ml) solution of Compound 63 (2.27 g, 4.23 mmol) and sodium iodide (15.9 g, 106 mmol) was added chlorotrimethylsilane (13.5 ml, 106 mmol) under ice-cooling, and the mixture was refluxed under heating for 6 hours at 90° C. The reaction solution was added with 10% sodium hydrogen sulfite aqueous solution (50 ml), and pH thereof was adjusted to 7.1 with 2N sodium hydroxide aqueous solution. Following three-time extractions with chloroform (70 ml), the extract was dried over anhydrous sodium sulfate. A crude product obtained by distilling off solvent under reduced pressure was recrystallized from methanol-diisopropyl ether to give Compound I-43 (917 mg, 58% yield) as yellow crystals.

Melting point: 120-124° C. Recrystallization solvent: methanol-chloroform

NMR (CDCl3) d: 1.54 (6H, s), 2.36 (3H, s), 4.18 (2H, s), 7.03 (2H, t, J=8.71 Hz), 7.20-7.24 (2H, m), 7.60 (1H, s).

MS (positive FABMS): m/Z 375 (M+H)$^+$, 749 (2M+H)$^+$.

Step 5

Reaction was performed in accordance with the method described in Step 5 of Example 3 using Compound I-43 (183 mg, 0.397 mmol) to give Compound I-44 (126 mg, 76% yield) as pale yellow crystals.

Melting point: 230° C. Recrystallization solvent: methanol-diisopropyl ether

NMR (CDCl3) d: 1.60 (6H, s), 2.09 (3H, s), 3.17 (3H, s), 4.18 (2H, s), 7.03 (2H, t, J=8.70 Hz), 7.19-7.23 (2H, m), 7.59 (1H, s), 11.88 (1H, brs).

MS (positive FABMS): m/Z 417 (M+H)+, 833 (2M+H)+.

In a similar manner, Compound I-45 was obtained.

Compound I-45

Melting point: 245° C. Recrystallization solvent: methanol-diisopropyl ether

NMR (CDCl3) d: 1.76 (6H, s), 3.12 (3H, s), 4.19 (2H, s), 7.20-7.24 (2H, m), 7.32-7.36 (2H, m), 7.60-7.65 (2H, m), 7.74-7.78 (1H, m), 11.60 (1H, brs).

MS (positive FABMS): m/Z 480 (M+H)+, 959 (2M+H)+.

Example 18

[Formula 45]

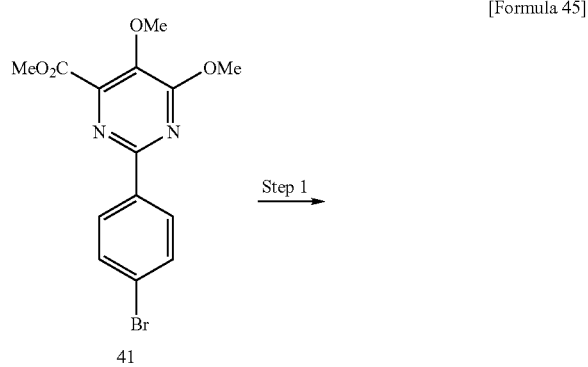

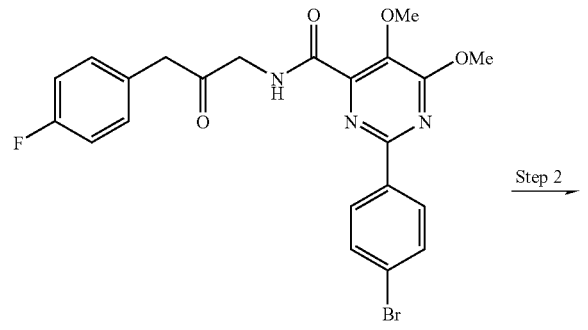

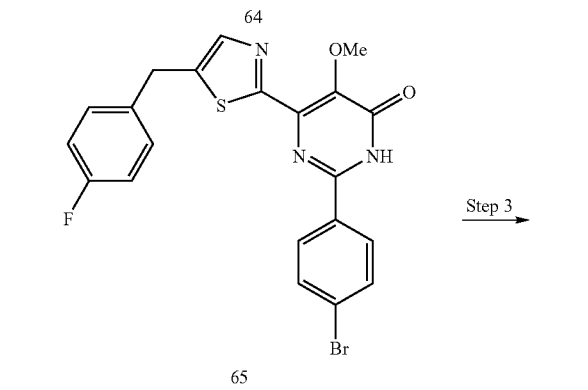

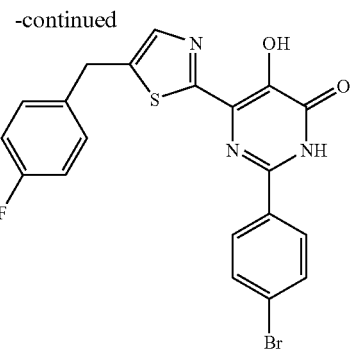

Step 1

Reaction was performed in accordance with the method described in Step 6 of Example 1 using Compound 41 obtained from Step 3 of Example 10 to give Compound 64 as a crude product.

Step 2

Reaction was performed in accordance with the method described in Step 4 of Example 5 using the crude product of Compound 64 to give Compound 65.

Step 3

Reaction was performed in accordance with the method described in Step 8 of Example 1 using Compound 65 (100 mg, 0.212 mmol) to give Compound I-46 (67.7 mg, 70% yield) as colorless crystals.

Melting point: >300° C. Recrystallization solvent: methanol

NMR (DMSO-d6) d: 4.28 (2H, s), 7.12-7.18 (2H, m), 7.34-7.38 (2H, m), 7.70 (2H, d, J=8.4 Hz), 7.91 (1H, s), 7.97 (2H, d, J=8.4 Hz), 12.97 (1H, brs).

Elemental analysis for $C_{20}H_{13}BrFN_3O_2S$

Calcd. (%): C, 52.41; H, 2.86; N, 9.17; Br, 17.43; F, 4.15; S, 7.00.

Found. (%): C, 51.94; H, 2.89; N, 9.09; Br, 17.04; F, 4.15; S, 7.20.

Example 19

[Formula 46]

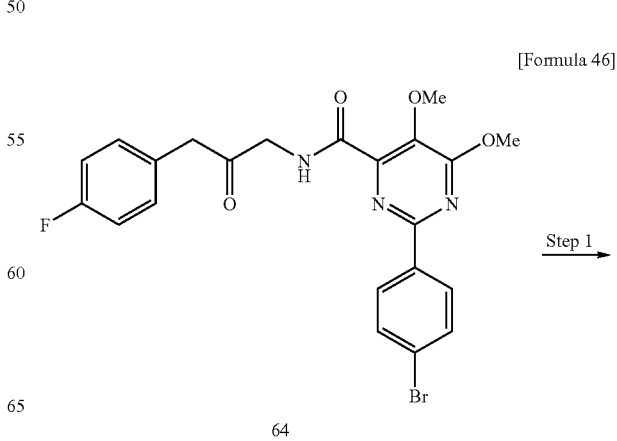

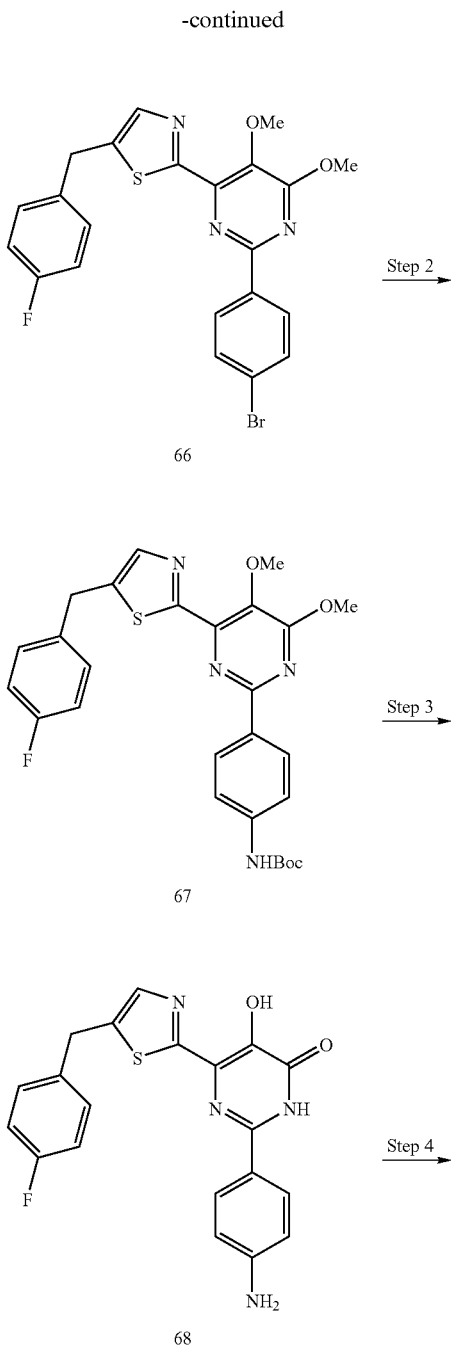

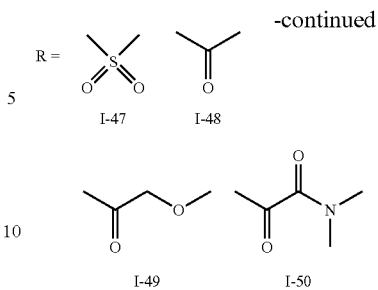

Step 1

Reaction was performed in accordance with the method described in Step 4 of Example 5 using the crude product of Compound 64 obtained from Step 1 of Example 18 to give Compound 66.

Step 3

To a dioxane (12 ml) solution of Compound 66 (600 mg, 1.23 mmol) were added palladium tris dibezylidene acetone (90.4 mg, 0.0987 mmol), 4,5-bis(diphenylphosphino)-9,9 dimethylxanthene (171 mg, 0.295 mmol), cesium carbonate (1.12 g, 3.44 mmol) and t-butylcarbamate (346 mg, 2.95 mmol) at room temperature, and the mixture was stirred for 17 hours at 100° C. The reaction solution was added with ice water, 10% citric acid aqueous solution and ethyl acetate, and insoluble matters were filtered off through celite, followed by extraction with ethyl acetate. The extract was washed with saturated brine, and dried over anhydrous sodium sulfate. A crude product obtained by distilling off the solvent under reduced pressure was subjected to silica gel chromatography. A fraction of objective product resulting from elution with hexane-ethyl acetate (4:1 v/v) was concentrated under reduced pressure to give Compound 67 (466 mg, 73% yield) as colorless crystals.

Step 4

To an acetic acid (8 ml) solution of Compound 67 (416 mg, 0.796 mmol) was added 47% hydrobromic acid (8 ml) at room temperature, and the mixture was refluxed under heating for 1 hour. After cooling to room temperature, the reaction solution was added with 5N sodium hydroxide aqueous solution for neutralization, and the precipitated crystals were collected by filtration. The obtained crude crystals were recrystallized from acetone to give Compound 68 (294 mg, 94% yield) as yellow crystals.

Step 5

To a tetrahydrofuran (4 ml) solution of Compound 68 (83.0 mg, 0.210 mmol) were added triethylamine (200 μl, 1.44 mmol) and methanesulfonyl chloride (78 μl, 1.01 mmol) at room temperature, and the mixture was stirred for 1 hour at room temperature. The reaction solution was added with 1N hydrochloric acid, and extracted with ethyl acetate. The extract was washed with 5N hydrochloric acid, water and saturated brine, and then dried over anhydrous sodium sulfate. A crude product obtained by distilling off solvent under reduced pressure was dissolved in 28% sodium methylate solution (2 ml), and stirred for 10 minutes at 60° C. After cooling to room temperature, 10% citric acid aqueous solution was added, and the precipitated crystals were collected by filtration. The obtained crude crystals were recrystallized from acetone to give Compound I-47 (17.4 mg, 18% overall yield) as pale yellow crystals.

Melting point: 283-285° C. Recrystallization solvent: acetone

NMR (DMSO-d6) d: 3.07 (3H, s), 4.28 (2H, s), 7.13-7.19 (2H, m), 7.27 (2H, d, J=8.7 Hz), 7.35-7.40 (2H, m), 7.90 (1H, s), 8.00 (2H, d, J=8.7 Hz).

MS (positive FABMS): m/Z 473 (M+H)+.

In a similar manner, Compounds I-47 to 49 were obtained.

Compound I-48

Melting point: >300° C. Recrystallization solvent: acetone

NMR (DMSO-d6) d: 2.08 (3H, s), 4.30 (2H, s), 7.14-7.19 (2H, m), 7.35-7.40 (2H, m), 7.69 (2H, d, J=8.4 Hz), 7.92 (1H, s), 8.00 (2H, d, J=8.4 Hz), 10.20 (1H, brs), 11.39 (1H, brs), 12.79 (1H, brs).

Elemental analysis for $C_{22}H_{17}FN_4O_3S$

Calcd. (%): C, 60.54; H, 3.93; N, 12.84; F, 4.35; S, 7.34.

Found. (%): C, 60.54; H, 3.91; N, 12.54; F, 4.23; S, 7.07.

MS (positive FABMS): m/Z 437 (M+H)+.

Compound I-49

Melting point: >300° C. Recrystallization solvent: acetone

NMR (DMSO-d6) d: 3.38 (3H, s), 4.04 (2H, s), 4.30 (2H, s), 7.14-7.20 (2H, m), 7.36-7.39 (2H, m), 7.80 (2H, d, J=8.7 Hz), 7.92 (1H, s), 8.02 (2H, d, J=8.7 Hz), 10.04 (1H, brs), 12.82 (1H, brs).

Elemental analysis for $C_{23}H_{19}FN_4O_4S(HCl)_{0.3}(H_2O)_{0.5}$

Calcd. (%): C, 56.79; H, 4.21; N, 11.52; F, 3.91; S, 6.59; Cl, 2.19.

Found. (%): C, 56.75; H, 4.17; N, 11.35; F, 3.77; S, 6.52; Cl, 2.06.

Compound I-50

Melting point: >300° C. Recrystallization solvent: acetone

NMR (DMSO-d6) d: 2.92 (3H, s), 3.02 (3H, s), 4.28 (2H, s), 7.12-7.18 (2H, m), 7.35-7.40 (2H, m), 7.76 (2H, d, J=9.0 Hz), 7.90 (1H, s), 8.00 (2H, d, J=9.0 Hz), 10.95 (1H, brs), 12.84 (1H, brs).

MS (positive FABMS): m/Z 494 (M+H)+, 987 (2M+H)+.

Example 20

[Formula 47]

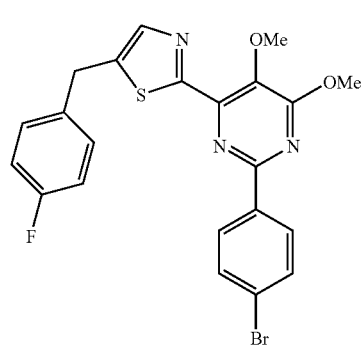

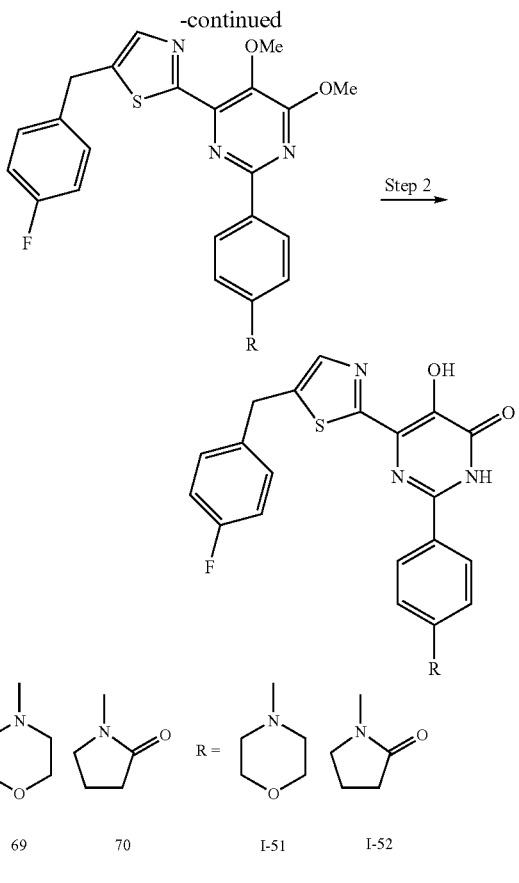

Step 1

Reaction was performed in accordance with the method described in Step 2 of Example 19 using Compound 66 (100 mg, 0.206 mmol) obtained in Step 1 of Example 19 to give Compound 69 (79.7 mg, 79% yield) as an oily product. In a similar manner, Compound 70 was obtained.

Step 2

Reaction was performed in accordance with the method described in Step 8 of Example 1 using Compound 69 (79.7 mg, 0.162 mmol) to give Compound I-51 (34.7 mg, 46% yield) as yellow crystals.

Melting point: >300° C. Recrystallization solvent: acetone

NMR (DMSO-d6) d: 3.22 (4H, t, J=4.8 Hz), 3.72 (4H, t, J=4.8 Hz), 4.27 (2H, s), 7.00 (2H, d, J=9.0 Hz), 7.13-7.18 (2H, m), 7.34-7.38 (2H, m), 7.89 (1H, s), 7.95 (2H, d, J=9.0 Hz), 12.62 (1H, brs).

MS (positive FABMS): m/Z 465 (M+H)+.

In a similar manner, Compound I-52 was obtained.

Compound I-52

Melting point: 290-292° C. Recrystallization solvent: acetone

NMR (DMSO-d6) d: 2.00-2.18 (2H, m), 2.49-2.56 (2H, m), 3.85-3.95 (2H, m), 4.30 (2H, s), 7.14-7.20 (2H, m), 7.36-7.41 (2H, m), 7.80 (2H, d, J=9.0 Hz), 7.92 (1H, s), 8.08 (2H, d, J=9.0 Hz), 12.87 (1H, brs).

MS (positive FABMS): m/Z 463 (M+H)+, 925 (2M+H)+.

Example 21

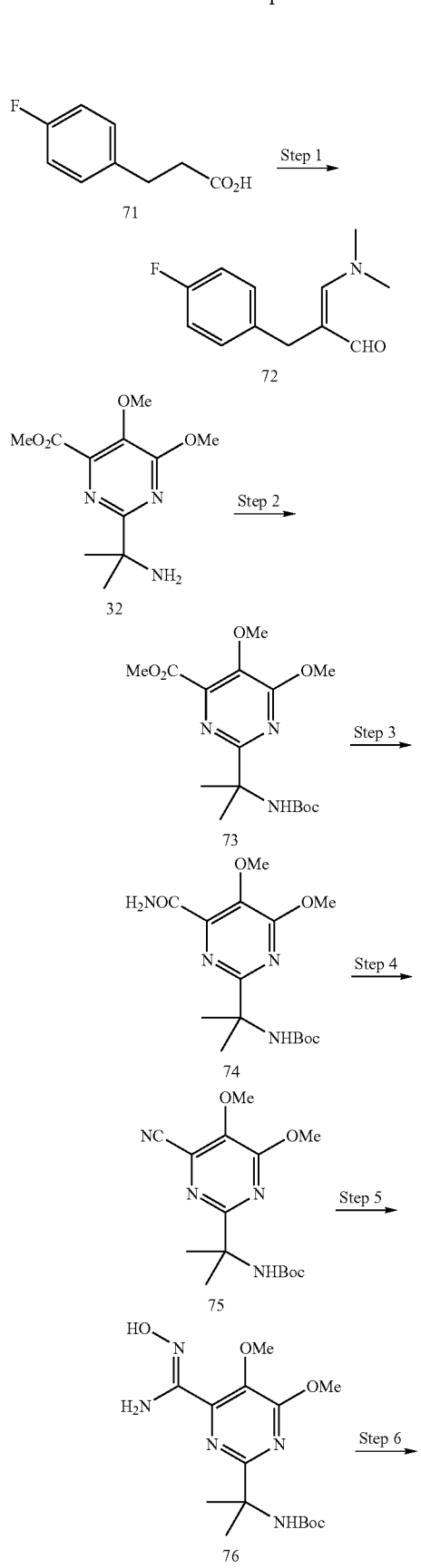

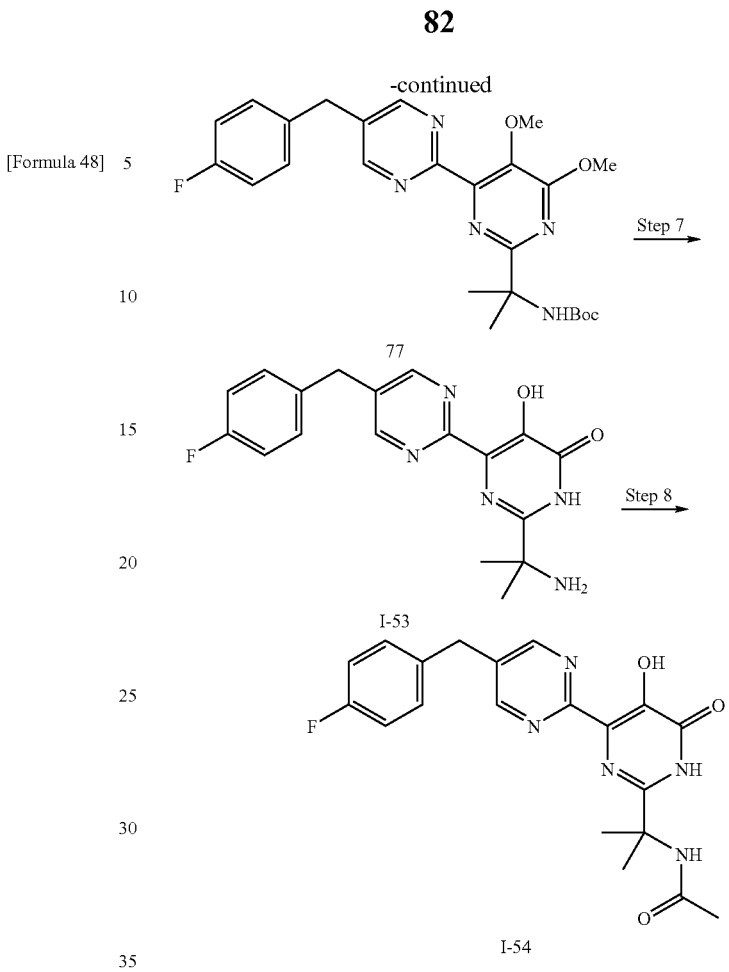

Step 1

To N,N-dimethylformamide (46.0 ml, 594 mmol) was added phosphorus oxychloride (16.5 ml, 177 mmol) under ice-cooling, and the mixture was stirred for 5 minute. Then the mixture was added with Compound 71 (10.08 g, 59.94 mmol) described in Patent (WO 03/121726) and stirred for 5 hours at 90° C. The reaction solution was added with ice (180 g), added with sodium hydroxide (24 g), and then added slowly with 10N sodium hydroxide aqueous solution (120 ml). After stirring for 1.5 hours at room temperature, the precipitated crystals were collected by filtration, washed with water, and dissolved in chloroform. A crude product obtained by distilling off solvent under reduced pressure was recrystallized from ethyl acetate-diethyl ether to obtain Compound 72 (2.41 g, 19% yield) as light brown crystals.

Step 2

To a tetrahydrofuran (200 ml) solution of Compound 32 (6.80 g, 26.6 mmol) obtained from Step 2 of Example 8 were added triethylamine (4.25 ml, 30.5 mmol) and di-tert-butyl-dicarbonate (6.70 ml, 29.2 mmol) under ice-cooling, and the mixture was stirred for 20 hours at room temperature. The reaction solution was distilled off under reduced pressure to give a crude product of Compound 73.

Step 3

Reaction was performed in accordance with the method described in Step 6 of Example 1 using the crude product of Compound 73 to give a crude product of Compound 74.

Step 4

To a methylene chloride (200 ml) solution of the crude product of Compound 74 were added triethylamine (7.50 ml, 53.8 mmol) and trifluoroacetic anhydride (3.80 ml, 26.9 mmol) under ice-cooling, and the mixture was stirred for 2.5 hours at room temperature. The reaction solution was added with saturated sodium bicarbonate water (100 ml), and extracted with chloroform. A crude product obtained by distilling off the solvent under reduced pressure was subjected to silica gel chromatography. A fraction of objective product resulting from elution with hexane-ethyl acetate (3:2 v/v) was concentrated under reduced pressure to give Compound 75 (6.19 g, 69% overall yield) as yellow oil.

Step 5

Compound 75 (4.00 g, 12.4 mmol) was dissolved in ethanol (16 ml), and added with hydroxylamine hydrochloric acid salt (1.20 g, 17.3 mmol) and triethylamine (2.96 ml, 21.2 mmol), and allowed to react for 5 minutes at 80° C. under microwave radiation. The reaction solution was added with water (200 ml), and extracted with ethyl acetate (300 ml). The extract was washed with saturated brine (200 ml), and dried over anhydrous sodium sulfate. The solvent was distilled off under reduced pressure to give Compound 76 (4.17 g, 95% yield) as colorless crystals.

Step 6

Compound 76 (1.07 g, 3.01 mmol) was dissolved in acetic acid (30 ml), added with acetic anhydride (0.425 ml, 4.50 mmol), and stirred for 5 minutes. Further, 10% palladium-carbon (150 mg) was added, and stirred for 2.5 hours in hydrogen atmosphere at 1 atmospheric pressure. A crude product obtained by filtering the reaction solution and distilling off the filtrate under reduced pressure and Compound 72 (750 mg, 3.62 mmol) were dissolved in methanol (15 ml), and added with 28% methanol solution (3.0 ml) of sodium methoxide and refluxed for 3 hours under heating. The reaction solution was cooled to 0° C., added with an aqueous solution of saturated ammonium chloride (15 ml) and water (15 ml), and extracted with chloroform. The extract was dried over anhydrous sodium sulfate, and the crude product obtained by distilling off the solvent under reduced pressure was subjected to silica gel chromatography. A fraction of objective product resulting from elution with hexane-ethyl acetate (3:2 v/v) was concentrated under reduced pressure to give Compound 77 (390 mg, 27% yield) as light brown oil.

Step 9

Compound 77 (390 mg, 0.807 mmol) was added with pyridine hydrochloric acid salt (4.0 g), and stirred for 5 minutes at 180° C. The reaction solution was cooled to 0° C., and added with water (10 ml) and 2N sodium hydroxide aqueous solution, and the water layer was washed three times with chloroform. Crystals that were precipitated by addition of 10% citric acid aqueous solution to the water layer were collected by filtration, and washed with water and diethyl ether, to give Compound I-53 (250 mg, 87% yield) as light brown crystals.

Melting point: 139-141° C. Recrystallization solvent: diethyl ether

NMR (DMSO-d6) d: 1.40 (6H, s), 4.07 (2H, s), 7.13-7.19 (2H, m), 7.34-7.39 (2H, m), 8.92 (2H, s).

MS (positive FABMS): m/Z 356 (M+H)+, 378 (M+Na)+, 711 (2M+H)+, 733 (2M+Na)+.

Step 10

Reaction was performed in accordance with the method described in Step 5 of Example 3 using Compound I-53 (150 mg, 0.422 mmol) to give title Compound I-54 (146 mg, 87% yield) as colorless crystals.

Melting point: 216-217° C. Recrystallization solvent: diethyl ether

NMR (DMSO-d6) d: 1.49 (6H, s), 1.84 (3H, s), 4.09 (2H, s), 7.12-7.18 (2H, m), 7.34-7.39 (2H, m), 8.02 (1H, s), 8.95 (2H, s), 12.18 (1H, brs), 12.78 (1H, brs).

MS (positive FABMS): m/Z 398 (M+H)+, 795 (2M+H)+.

Example 22

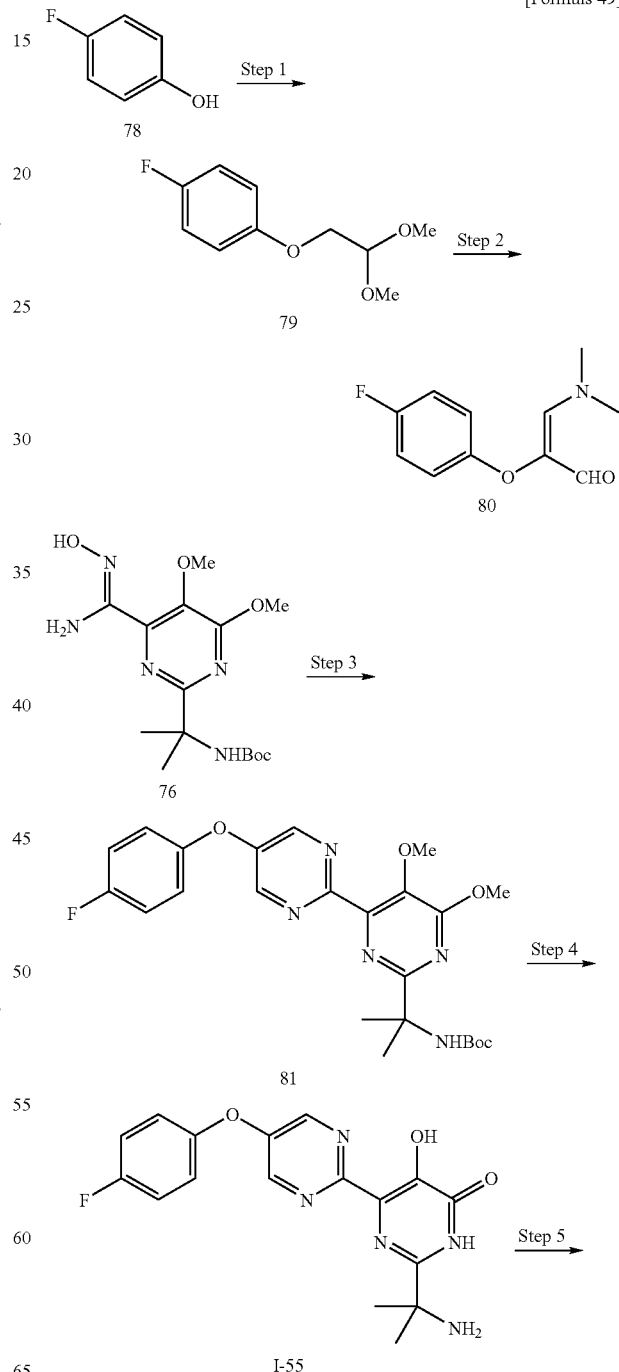

[Formula 49]

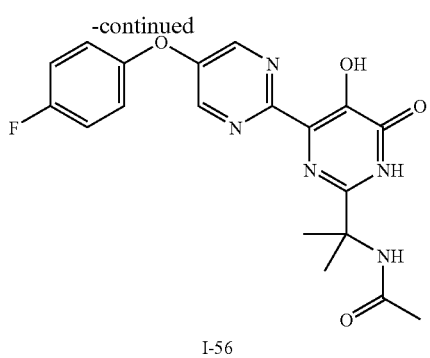

I-56

Step 1

4-fluorophenol (25.26 g, 225.3 mmol) and potassium iodide (1.84 g, 11.1 mmol) were dissolved in N,N-dimethylformamide (100 ml), added with potassium carbonate (34.31 g, 248.2 mmol) and bromoacetoaldehyde dimethylacetal (32.0 ml, 270 mmol) at room temperature, stirred for 75 minutes at 90° C., and further stirred for 20 hours at 120° C. The reaction solution was cooled to 0° C., added with water (300 ml), and extracted twice with diethyl ether (300 ml). The extract was washed with 1N sodium hydroxide aqueous solution (200 ml), water (200 ml) and saturated brine (100 ml), and then dried over anhydrous sodium sulfate. The solvent was distilled off under reduced pressure to give a crude product of Compound 79.

Step 2

To N,N-dimethylformamide (48.0 ml, 620 mmol) was added phosphorus oxychloride (57.0 ml, 612 mmol) under ice-cooling, and the mixture was stirred for 45 minutes at 50° C. The reaction solution was added with chloroform (60 ml), and added with a chloroform (40 ml) solution of the crude product of Compound 79 over 25 minutes at 70° C., and then refluxed for 7 hours under heating. After leaving for 12 hours at room temperature, the reaction solution was slowly added to 50% potassium carbonate aqueous solution (1000 ml), toluene (450 ml) and an ethanol (50 ml) suspension under ice-cooling, and extracted twice with chloroform. The extract was dried over anhydrous magnesium sulfate, and the crude product obtained by distilling off the solvent under reduced pressure was subjected to silica gel chromatography. A fraction of objective product resulting from elution with chloroform-methanol (30:1 v/v) was concentrated under reduced pressure to give a crude product which was then recrystallized from diethyl ether-diisopropyl ether to give Compound 80 (18.13 g, 39% overall yield) as light brown crystals.

Step 3

Reaction was performed in accordance with the method described in Step 6 of Example 21 using Compound 76 (1.07 g, 3.01 mmol) obtained in Step 5 of Example 21 and the above Compound 80 (756 mg, 3.61 mmol) to give Compound 81 (548 mg, 38% yield) as pale yellow oil.

Step 4

Reaction was performed in accordance with the method described in Step 9 of Example 21 using Compound 81 (529 mg, 1.09 mmol) to give Compound I-55 (292 mg, 75% yield) as colorless crystals.

Melting point: 198-199° C. Recrystallization solvent: diethyl ether

NMR (DMSO-d6) d: 1.63 (6H, s), 7.33-7.35 (4H, m), 8.58 (2H, brs), 8.86 (2H, s), 12.65 (1H, brs).

MS (positive FABMS): m/Z 358 (M+H)+, 715 (2M+H)+.

Step 5

Reaction was performed in accordance with the method described in Step 5 of Example 3 using Compound I-55 (152 mg, 0.425 mmol) to give Compound I-56 (137 mg, 81% yield) as colorless crystals.

Melting point: 147-148° C. Recrystallization solvent: diethyl ether

NMR (DMSO-d6) d: 1.50 (6H, s), 1.84 (3H, s), 7.31-7.33 (4H, m), 8.03 (1H, s), 8.83 (2H, s), 12.26 (1H, brs), 12.39 (1H, brs).

MS (positive FABMS): m/Z 400 (M+H)+, 799 (2M+H)+.

Example 23

[Formula 50]

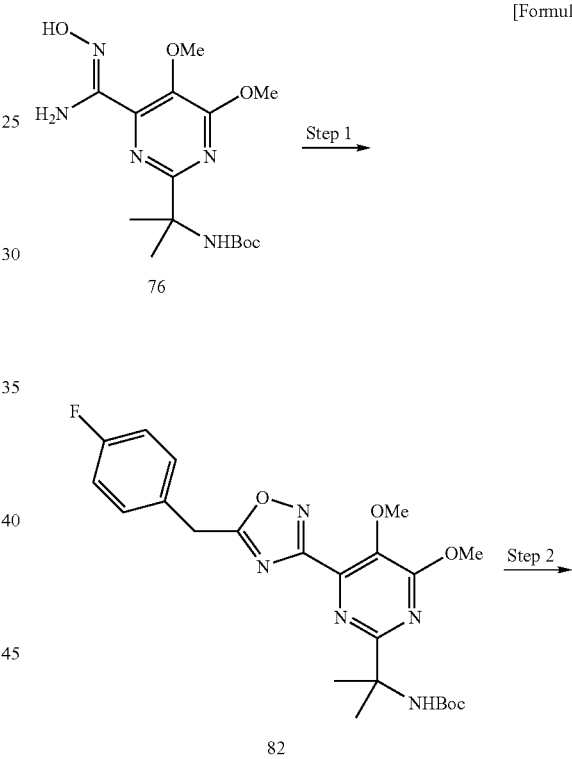

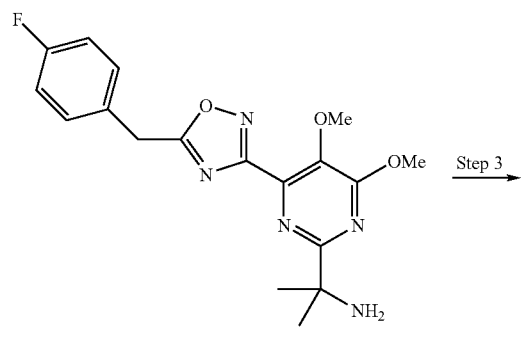

-continued

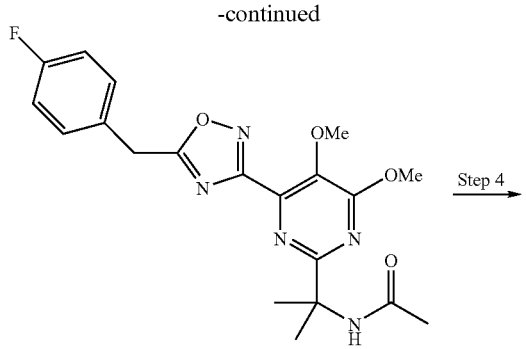

84

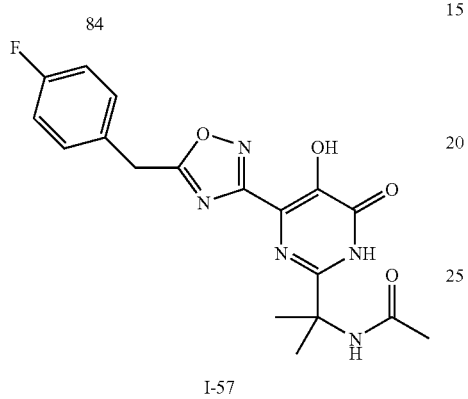

I-57

Step 1

Compound 76 (3.99 g, 11.2 mmol) was dissolved in pyridine (9 ml), and added dropwise with parafluorophenylacetyl chloride (1.93 ml, 13.44 mmol) at room temperature over 10 minutes, and directly stirred for 5 minutes, and then stirred for 3 hours at 100° C. The reaction solution was added to ice water (100 ml), and extracted with ethyl acetate. The extract was washed with saturated sodium hydrogen carbonate aqueous solution and saturated brine, and then dried over anhydrous sodium sulfate. A crude product obtained by distilling off the solvent under reduced pressure was subjected to silica gel chromatography. A fraction of target product obtained by elution with hexane-ethyl acetate (3:1 v/v) was concentrated under reduced pressure to give Compound 82 (2.42 g, 46% yield) as colorless crystals.

Step 2

Compound 82 (710 mg, 1.50 mmol) was dissolved in acetic acid (13.5 ml), added with 47% hydrobromic acid (4.5 ml) at room temperature, and directly stirred for 2.5 hours. The reaction solution was added with 5N sodium hydroxide aqueous solution (33 ml) and saturated sodium hydrogen carbonate aqueous solution (50 ml) under ice-cooling, and extracted twice with chloroform. The extract was washed with saturated brine, and then dried over anhydrous sodium sulfate. The solvent was distilled off under reduced pressure to give a crude product of Compound 83 (754 mg).

Step 3

Reaction was performed in accordance with the method described in Step 5 of Example 3 using the crude product of Compound 83 (754 mg) to give a crude product of Compound 84 (640 mg).

Step 4

Compound 84 (740 mg, 1.78 mmol) was dissolved in methylene chloride (36 ml), and added with 1.0M methylene chloride solution (53 ml) of boron tribromide at room temperature, and directly stirred for 4 days. The reaction solution was added to ice water, and 5N sodium hydroxide aqueous solution (55 ml), 5N hydrochloric acid (15 ml) and 10% citric acid aqueous solution (40 ml) were added, followed by extraction with chloroform. The extract was washed with saturated brine, and dried over anhydrous sodium sulfate. A crude product obtained by distilling off solvent under reduced pressure was recrystallized from ethyl acetate-diisopropyl ether to give Compound I-57 (111 mg, 16% yield) as colorless crystals.

Melting point: 202-203° C. Recrystallization solvent: ethyl acetate-diisopropyl ether NMR (CDCl3) d: 1.73 (6H, s), 2.04 (3H, s), 4.34 (2H, s), 6.29 (1H, brs), 7.03-7.09 (2H, m), 7.29-7.34 (2H, m) 9.46 (1H, brs), 12.24 (1H, brs).

Elemental analysis for $C_{18}H_{18}FN_5O_4$

Calcd. (%): C, 55.81; H, 4.68; N, 18.08; F, 4.90.

Found. (%): C, 55.85; H, 4.63; N, 17.93; F, 4.73.

Example 24

[Formula 51]

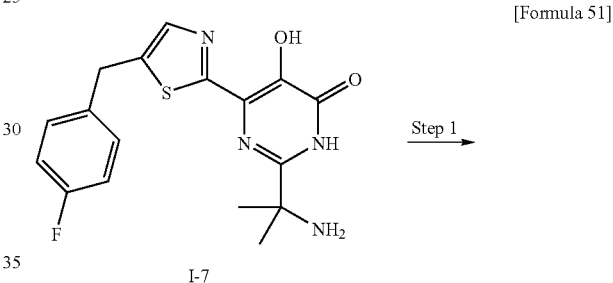

I-7

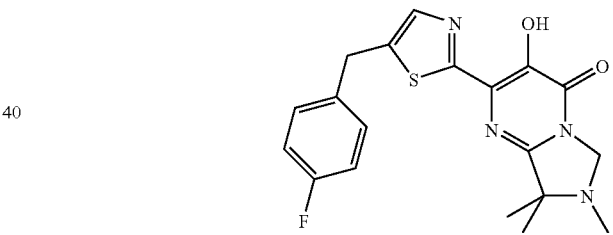

I-58

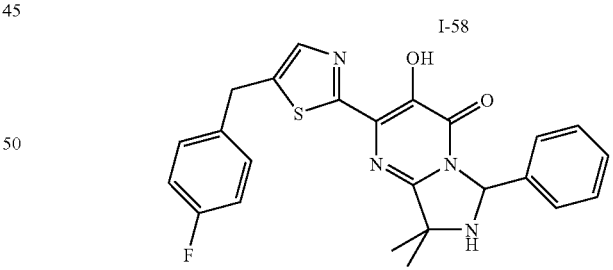

I-59

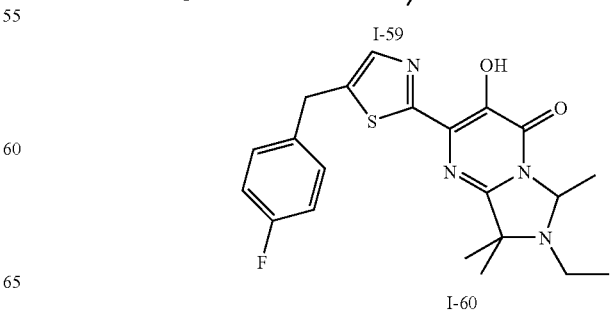

I-60

-continued

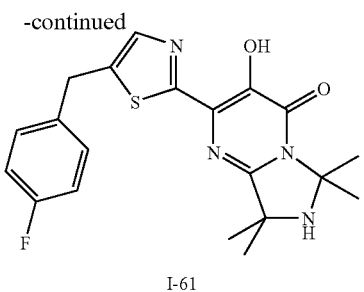

I-61

Step 1

To a methylene chloride (2 ml) solution of Compound I-7 (100 mg, 0.277 mmol) was added formalin (113 mg, 1.39 mmol), and then were added acetic acid (0.095 ml, 1.66 mmol) and sodium triacetoxy borohydride (295 mg, 1.39 mmol) at 0° C., and the mixture was stirred for 4 hours at room temperature. The reaction solution was added with saturated sodium bicarbonate water (20 ml), and extracted three times with chloroform (20 ml). The extract was washed with water (30 ml), and dried over anhydrous sodium sulfate. The solvent was distilled off under reduced pressure to give a crude product of Compound I-58. This was then recrystallized from methanol-diisopropyl ether to give Compound I-58 (115 mg, 100% yield) as colorless crystals.

Melting point: 174-175° C. Recrystallization solvent: methanol-diisopropyl ether NMR (CDCl3) d: 1.33 (6H, s), 2.43 (3H, s), 4.18 (2H, s), 4.75 (2H, s), 7.03 (2H, m), 7.22 (2H, m), 7.61 (1H, s), 11.94 (1H, brs).

Elemental analysis for $C_{19}H_{19}FN_4O_2S$

Calcd. (%): C, 59.05; H, 4.96; N, 14.50; F, 4.92; S, 8.30.
Found. (%): C, 58.91; H, 5.05; N, 14.32; F, 4.67; S, 8.37.
MS (positive FABMS): m/Z 387 (M+H)$^+$, 773 (2M+H)$^+$.

In a similar manner, Compounds I-59 to I-61 were obtained.

Compound I-59

Melting point: 210-212° C. Recrystallization solvent: methanol-diisopropyl ether NMR (CDCl3) d: 1.47 (6H, s), 4.27 (2H, s), 6.23 (1H, s), 7.04 (2H, t, J=8.7 Hz), 7.21-7.25 (2H, m), 7.35 (4H, m), 7.62 (1H, s), 11.80 (1H, brs).

Elemental analysis for $C_{24}H_{21}FN_4O_2S$

Calcd. (%): C, 64.27; H, 4.72; N, 12.49; F, 4.24; S, 7.15.
Found. (%): C, 64.08; H, 4.72; N, 12.18; F, 3.99; S, 7.05.
MS (positive FABMS): m/Z 449 (M+H)$^+$, 897 (2M+H)$^+$.

Compound I-60

Melting point: 165-168° C. Recrystallization solvent: methanol-diisopropyl ether NMR (CDCl3) d: 1.19 (3H, s), 1.38 (3H, s), 1.44 (3H, s), 1.63 (3H, d, J=5.7 Hz), 2.58 (2H, m), 4.18 (2H, s), 5.38 (1H, d, J=5.7 Hz), 7.03 (2H, t, J=8.1 Hz), 7.19-7.25 (2H, m), 7.61 (1H, s).

MS (positive FABMS): m/Z 415 (M+H)$^+$, 829 (2M+H)$^+$, 851 (2M+Na)$^+$.

Compound I-61

Melting point: 193-195° C. Recrystallization solvent: methanol

NMR (CDCl3) d: 1.49 (6H, s), 1.81 (6H, s), 4.18 (2H, s), 7.03 (2H, t, J=8.71 Hz), 7.20-7.24 (2H, m), 7.60 (1H, s), 11.81 (1H, brs).

MS (positive FABMS): m/Z 401 (M+H)$^+$, 801 (2M+H)$^+$.

Example 25

[Formula 52]

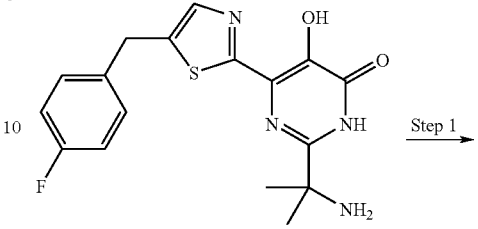

I-7

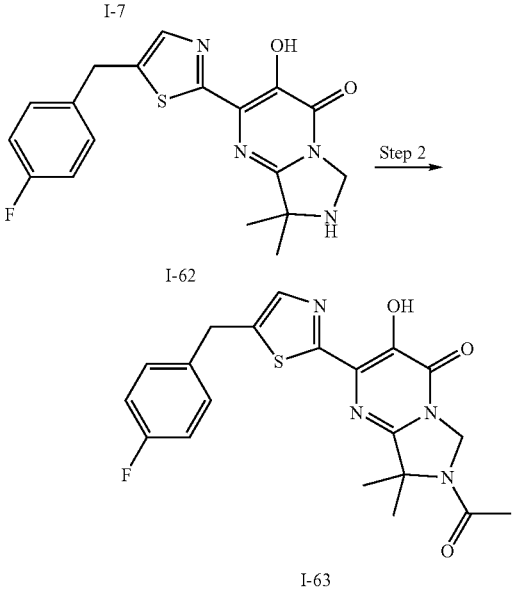

I-62

I-63

Step 1

To a methylene chloride (4 ml) solution of Compound I-7 (200 mg, 0.277 mmol) was added formalin (226 mg, 2.78 mmol), and the mixture was added with acetic acid at room temperature and stirred for 2 hours. The reaction solution was added with saturated sodium bicarbonate water (20 ml), and extracted three times with chloroform (20 ml). The extract was washed with water (30 ml), and dried over anhydrous sodium sulfate. The solvent was distilled off under reduced pressure to give a crude product (140 mg) of Compound I-62.

Step 2

The crude product (140 mg) of Compound I-62 was dissolved in methylenechloride (4 ml), and added with triethylamine (0.157 ml, 1.13 mmol), acetic anhydride (0.107 ml, 1.13 mmol) and 4-dimethylaminopyridine (10 mg) at room temperature, and stirred for 1 hour. The reaction solution was added with 2N hydrochloric acid (20 ml), and extracted three times with chloroform (20 ml). The extract was washed with water (30 ml), and dried over anhydrous sodium sulfate. A crude product obtained by distilling off the solvent under reduced pressure was subjected to silica gel chromatography. A fraction of target product obtained by elution of hexane-ethyl acetate (1:1 v/v) was concentrated under reduced pressure to give N,O-diacetyl product (92 mg, 36% yield) and O-acetyl product (70 mg, 30% yield). The N,O-diacetyl product (72 mg, 0.16 mmol) was dissolved in methanol (2 ml) and methylene chloride (1 ml), added with 1N lithium hydroxide solution (0.5 ml) at room temperature, and stirred for 45 minutes. After adding 2N hydrochloric acid (20 ml), the mixture was extracted three times with chloroform (20 ml). The extract was washed with water (30 ml), and dried over anhydrous sodium sulfate. A crude product obtained by distilling off solvent under reduced pressure was recrystallized from methanol to give Compound I-63 (30 mg, 46% yield) as colorless crystals. In a similar manner, O-acetyl product (60 mg, 0.15 mmol) was hydrolyzed to give Compound I-62 (32 mg, 59% yield) as colorless crystals.

Compound I-62

Melting point: 249-251° C. Recrystallization solvent: methanol

NMR (CDCl3) d: 1.50 (6H, s), 4.18 (2H, s), 5.07 (2H, s), 7.03 (2H, t, J=8.7 Hz), 7.20-7.26 (2H, m), 7.62 (1H, s).

MS (positive FABMS): m/Z 373 (M+H)$^+$, 745 (2M+H)$^+$.

Compound I-63

Melting point: 179-180° C. Recrystallization solvent: methanol

NMR (CDCl3) d: 1.80 (6H, s), 2.14 (3H, s), 4.19 (2H, s), 5.50 (2H, s), 7.04 (2H, t, J=8.7 Hz), 7.20-7.25 (2H, m), 7.63 (1H, s), 11.80 (1H, brs).

MS (positive FABMS): m/Z 415 (M+H)$^+$, 829 (2M+H)$^+$.

Example 26

[Formula 53]

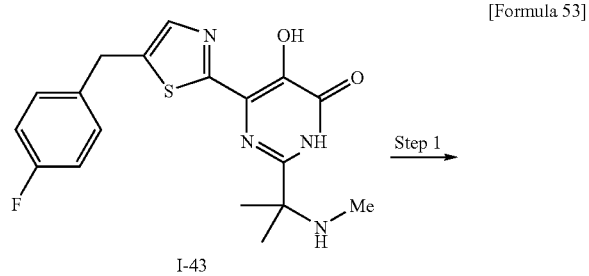

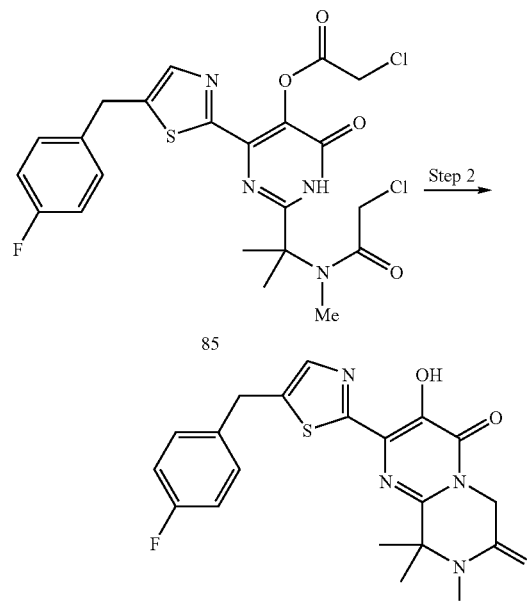

Step 1

Compound I-43 (150 mg, 0.40 mmol) obtained from Step 4 of Example 17 was dissolved in methylene chloride (9 ml), added with triethylamine (0.224 ml, 1.61 mmol) and chloroacetyl chloride (0.064 ml, 0.81 mmol), and stirred for 15 minutes at room temperature. The reaction solution was added with 10% citric acid aqueous solution, and extracted with ethyl acetate. The extract was washed with saturated brine, and then dried over anhydrous sodium sulfate. The solvent was distilled off under reduced pressure to give a crude product (182 mg) of Compound 85.

Step 2

To a N,N-dimethylformamide (8 ml) solution of the crude product (182 mg) of Compound 85 was added cesium carbonate (228 mg, 0.70 mmol), and the mixture was stirred for 15 minutes at 50° C. After cooling to room temperature, the reaction solution was added with 1N lithium hydroxide solution (4 ml), and stirred for 1 minute. Then 10% citric acid aqueous solution (16 ml) was added, followed by extraction twice with ethyl acetate. The extract was washed three times with water, and then dried over anhydrous sodium sulfate. A crystalline residue obtained by distilling off the solvent under reduced pressure was recrystallized from acetone-diethyl ether to give Compound I-64 (96 mg, 58% overall yield) as yellow crystals.

Melting point: 225-226° C. Recrystallization solvent: acetone-diethyl ether

NMR (CDCl3) d: 1.69 (6H, s), 3.08 (3H, s), 4.20 (2H, s), 4.72 (2H, s), 7.01-7.07 (2H, m), 7.21-7.23 (2H, m), 7.64 (1H, s).

Elemental analysis for $C_{20}H_{19}FN_4O_3S$

Calcd. (%): C, 57.96; H, 4.62; N, 13.52; F, 4.58; S, 7.74.

Found. (%): C, 57.56; H, 4.34; N, 13.15; F, 4.14; S, 7.16.

Example 27

[Formula 54]

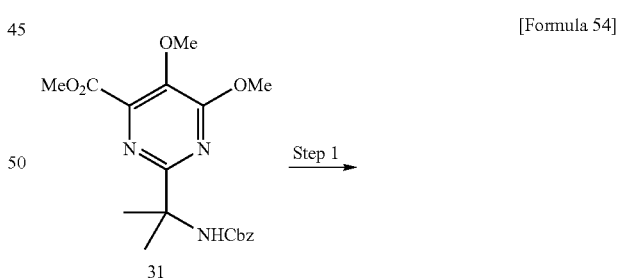

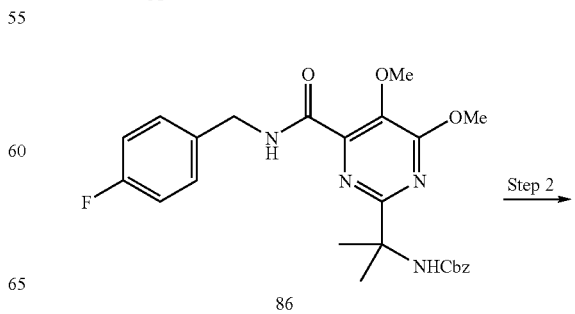

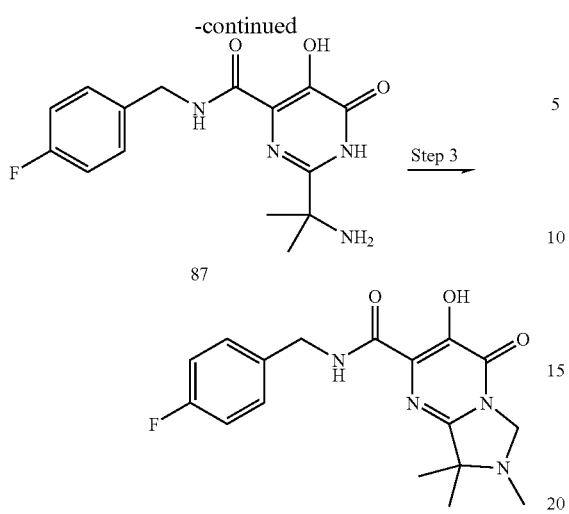

Step 1
Reaction was performed in accordance with the method described in Step 6 of Example 1 using Compound 31 obtained from Step 1 of Example 8 to give Compound 86 as a crude product.

Step 2
Reaction was performed in accordance with the method described in Step 8 of Example 1 using the crude product of Compound 86 to give Compound 87 as pale yellow crystals.

Step 3
Reaction was performed in accordance with the method described in Step 1 of Example 24 using Compound 87 (130 mg, 0.406 mmol) to give Compound I-65 (75 mg, 53% yield) as pale pink crystals.

Melting point: 149-150° C. Recrystallization solvent: methanol-diisopropyl ether NMR (CDCl3) d: 1.29 (6H, s), 2.41 (3H, s), 4.59 (2H, d, J=6.3 Hz), 4.72 (2H, s), 7.07 (2H, t, J=8.7 Hz), 7.31-7.35 (2H, m), 7.77 (1H, s), 12.25 (1H, brs).

MS (positive FABMS): m/Z 347 (M+H)+, 693 (2M+H)+.

In a similar manner, Compounds I-66 and I-67 were obtained.

Compound I-66

Melting point: 128-129° C. Recrystallization solvent: diisopropyl ether

NMR (CDCl3) d: 1.16 (3H, t, J=7.2 Hz), 1.32 (3H, s), 1.39 (3H, s), 1.60 (3H, d, J=5.7 Hz), 2.68-2.84 (2H, m), 4.57-4.60 (2H, m), 5.29 (1H, q, J=5.7 Hz), 7.02-7.08 (2H, m), 7.30-7.35 (2H, m), 7.91 (1H, brs), 12.16 (1H, s).

MS (positive FABMS): m/Z 375 (M+H)+, 749 (2M+H)+.

Compound I-67

Melting point: 136-138° C. Recrystallization solvent: ethyl acetate-diisopropyl ether NMR (CDCl3) d: 1.46 (6H, s), 4.59-4.63 (2H, m), 6.24 (1H, s), 7.04-7.10 (2H, m), 7.29-7.37 (7H, m), 7.92 (1H, brs), 12.25 (1H, s).

MS (positive FABMS): m/Z 409 (M+H)+, 817 (2M+H)+.

Example 28

[Formula 55]

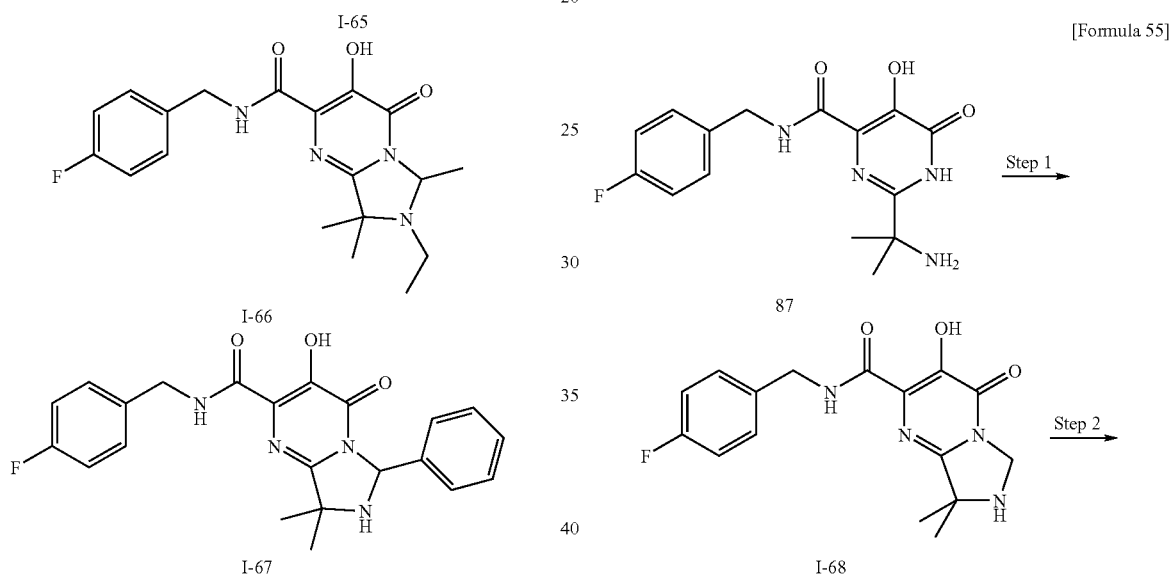

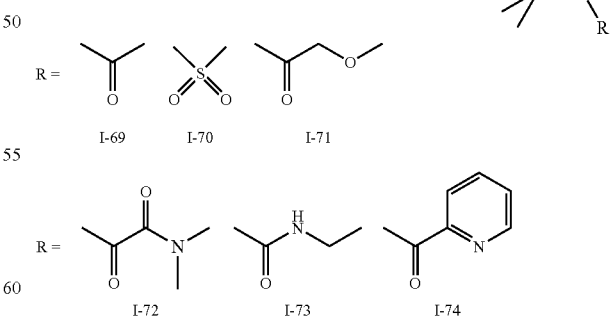

Step 1
To a methylene chloride (40 ml) solution of Compound 87 (2.0 g, 4.46 mmol) obtained from Step 2 of Example 27 were added 30% formaldehyde aqueous solution (2.7 ml, 31.2 mmol) and acetic acid (2.1 ml, 37.4 mmol) at room temperature, and the mixture was stirred for 1 hour. The reaction solution was added with saturated sodium bicarbonate water, and extracted with chloroform. The extract was washed with water, and then dried over anhydrous sodium sulfate. A crude product obtained by distilling off solvent under reduced pressure was dissolved in tetrahydrofuran (40 ml), added with trifluoroacetic acid (1 ml) at room temperature, and stirred for 30 minutes. The reaction solution was added with saturated sodium bicarbonate water, and extracted with ethylacetate. The extract was washed with water, and then dried over anhydrous sodium sulfate. A crystalline residue obtained by distilling off the solvent under reduced pressure was recrystallized from ethyl acetate-diisopropyl ether to give Compound I-68 (1.29 g, 87% yield) as pale yellow crystals.

Melting point: 216-218° C. Recrystallization solvent: ethyl acetate-diisopropyl ether NMR (DMSO-d6) d: 1.41 (6H, s), 4.48 (2H, d, J=6.6 Hz), 4.78 (2H, s), 7.14-7.17 (2H, m), 7.35-7.40 (2H, m), 9.41 (1H, brs), 12.56 (1H, s).

MS (positive FABMS): m/Z 333 (M+H)$^+$.

Step 2

To a pyridine (6 ml) solution of Compound I-68 (150 mg, 0.451 mmol) was added acetyl chloride (0.096 ml, 1.35 mmol) at room temperature, and the mixture was stirred for 1 hour. The reaction solution was added with 1N hydrochloric acid, and extracted with ethyl acetate. The extract was washed with 2N hydrochloric acid and water, and dried over anhydrous sodium sulfate. A crude product obtained by distilling off the solvent under reduced pressure was dissolved in tetrahydrofuran (6 ml), added with 1N lithium hydroxide solution (1.5 ml) at room temperature, and stirred for 30 minutes. The reaction solution was added with 1N hydrochloric acid, and extracted with ethyl acetate. The extract was washed with water, and dried over anhydrous sodium sulfate. A crystalline residue obtained by distilling off the solvent under reduced pressure was recrystallized from ethyl acetate-diisopropyl ether to give Compound I-69 (47.5 mg, 28% yield) as colorless crystals.

Melting point: 230-232° C. Recrystallization solvent: ethyl acetate-diisopropyl ether NMR (CDCl3) d: 1.76 (6H, s), 2.13 (3H, s), 4.60 (2H, d, J=6.3 Hz), 5.48 (2H, s), 7.04-7.09 (2H, m), 7.31-7.36 (2H, m), 7.87 (1H, brs), 12.45 (1H, s).

MS (positive FABMS): m/Z 375 (M+H)$^+$.

In a similar manner, Compounds I-70 to I-74 were obtained.

Compound I-70

Melting point: 195-196° C. Recrystallization solvent: ethyl acetate-diisopropyl ether NMR (CDCl3) d: 1.75 (6H, s), 3.05 (3H, s), 4.60 (2H, d, J=6.3 Hz), 5.36 (2H, s), 7.03-7.09 (2H, m), 7.30-7.34 (2H, m), 7.90 (1H, brs), 12.46 (1H, s).

Elemental analysis for $C_{17}H_{18}FN_4O_5S(H_2O)_{0.1}(HCl)_{0.1}$

Calcd. (%): C, 49.10; H, 4.68; N, 13.47; S, 7.71; F, 4.57; Cl 0.85.

Found. (%): C, 49.13; H, 4.70; N, 13.01; S, 8.21; F, 4.08; Cl 0.67.

MS (positive FABMS): m/Z 411 (M+H)$^+$, 821 (2M+H)$^+$.

Compound I-71

Melting point: 155-158° C. Recrystallization solvent: ethyl acetate-diisopropyl ether NMR (CDCl3) d: 1.78 (6H, s), 3.46 (3H, s), 4.05 (2H, s), 4.60 (2H, d, J=6.3 Hz), 5.59 (2H, s), 7.04-7.09 (2H, m), 7.31-7.36 (2H, m), 7.86 (1H, brs), 12.44 (1H, s).

MS (positive FABMS): m/Z 405 (M+H)$^+$, 809 (2M+H)$^+$.

Compound I-72

Melting point: 134-136° C. Recrystallization solvent: ethyl acetate-diisopropyl ether NMR (CDCl3) d: 1.83 (6H, s), 3.02 (3H, s), 3.06 (3H, s), 4.60 (2H, d, J=6.3 Hz), 5.54 (2H, s), 7.03-7.09 (2H, m), 7.30-7.35 (2H, m), 7.83 (1H, brs), 12.46 (1H, s).

MS (positive FABMS): m/Z 432 (M+H)$^+$, 863 (2M+H)$^+$.

Compound I-73

Melting point: 246-248° C. Recrystallization solvent: ethyl acetate-diisopropyl ether NMR (CDCl3) d: 1.19 (3H, t, J=7.2 Hz), 1.74 (6H, s), 3.28-3.36 (2H, m), 4.46 (1H, brs), 4.60 (2H, d, J=6.0 Hz), 5.37 (2H, s), 7.03-7.09 (2H, m), 7.31-7.36 (2H, m), 7.88 (1H, brs), 12.40 (1H, s).

Elemental analysis for $C_{19}H_{22}FN_5O_4(AcOEt)_{0.3}$

Calcd. (%): C, 56.44; H, 5.72; N, 16.29; F, 4.42.

Found. (%): C, 56.46; H, 5.68; N, 16.45; F, 4.20.

MS (positive FABMS): m/Z 404 (M+H)$^+$, 807 (2M+H)$^+$.

Compound I-74

Melting point: 155-157° C. Recrystallization solvent: ethyl acetate-diisopropyl ether NMR (CDCl3) d: 1.91 (6H, s), 4.61 (2H, d, J=6.3 Hz), 6.11 (2H, s), 7.04-7.10 (2H, m), 7.32-7.43 (2H, m), 7.43-7.47 (1H, m), 7.84-7.89 (1H, m), 7.91 (1H, brs), 8.01-8.04 (1H, m), 8.65-8.67 (1H, m), 12.40 (1H, s).

MS (positive FABMS): m/Z 438 (M+H)$^+$, 875 (2M+H)$^+$.

Example 29

[Formula 56]

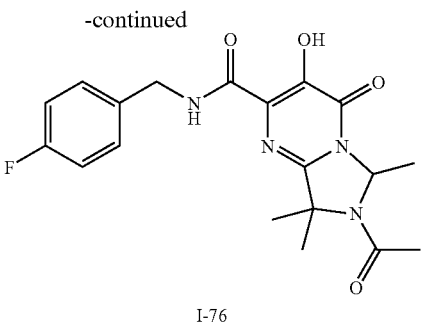

I-76

Step 1

Reaction was performed in accordance with the method described in Step 1 of Example 28 using Compound 87 (150 mg, 0.335 mmol) obtained from Step 2 of Example 27 to give Compound I-75 (44 mg, 38% yield) as colorless crystals.

Melting point: 109-110° C. Recrystallization solvent: diisopropyl ether

NMR (CDCl3) d: 1.36 (3H, s), 1.52 (3H, s), 1.76 (3H, d, J=5.7 Hz), 4.59 (2H, d, J=6.3 Hz), 5.35 (1H, q, J=5.7 Hz), 7.03-7.09 (2H, m), 7.31-7.35 (2H, m), 7.90 (1H, brs), 12.19 (1H, s).

MS (positive FABMS): m/Z 347 (M+H)$^+$, 693 (2M+H)$^+$.

Step 2

Reaction was performed in accordance with the method described in Step 2 of Example 28 using Compound I-75 (241 mg, 0.696 mmol) to give Compound I-76 (15 mg, 16% yield) as colorless crystals.

Melting point: 110-112° C. Recrystallization solvent: diisopropyl ether

NMR (CDCl3) d: 1.75 (6H, s), 1.79 (3H, d, J=5.4 Hz), 2.17 (3H, s), 4.58-4.62 (2H, m), 6.07 (1H, q, J=5.4 Hz), 7.03-7.09 (2H, m), 7.31-7.35 (2H, m), 7.88 (1H, brs), 12.39 (1H, s).

MS (positive FABMS): m/Z 389 (M+H)$^+$.

Example 30

[Formula 57]

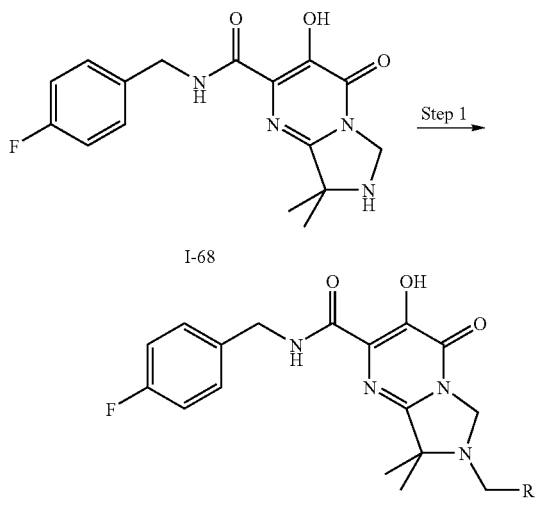

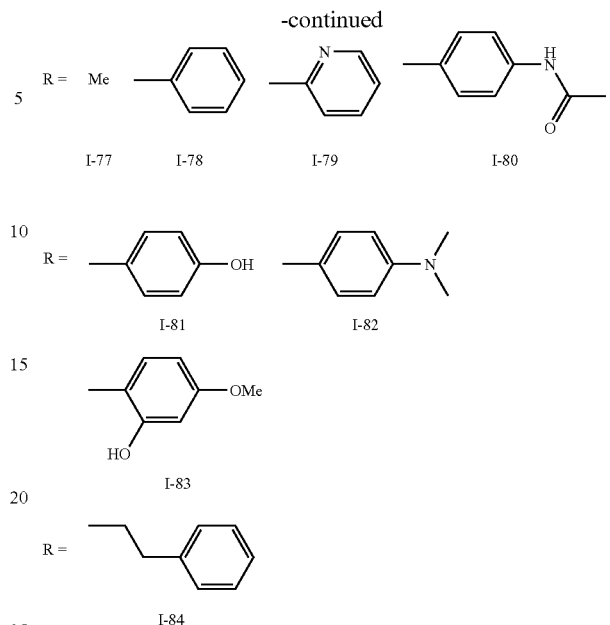

Step 1

Compound I-68 (150 mg, 0.451 mmol) obtained from Step 1 of Example 28 was dissolved in methylene chloride (3 ml), and added with acetoaldehyde (0.146 ml, 2.34 mmol), acetic acid (0.161 ml, 2.81 mmol) and sodium triacetoxy borohydride (496 mg, 2.34 mmol), and allowed to react for 1 hour at room temperature. The reaction solution was added with saturated sodium bicarbonate water, and extracted with chloroform. The extract was washed with saturated brine, and then dried over anhydrous sodium sulfate. A crude product obtained by distilling off the solvent under reduced pressure was subjected to silica gel chromatography. A fraction of target product obtained by elution with ethyl acetate was concentrated under reduced pressure to give Compound I-77 (65 mg, 40% yield) as colorless crystals.

Melting point: 158-160° C. Recrystallization solvent: diisopropyl ether

NMR (CDCl3) d: 1.18 (3H, t, J=7.2 Hz), 1.31 (6H, s), 2.68 (2H, q, J=7.2 Hz), 4.59 (2H, d, J=6.3 Hz), 4.77 (2H, s), 7.03-7.09 (2H, m), 7.31-7.35 (2H, m), 7.90 (1H, brs), 12.29 (1H, s).

MS (positive FABMS): m/Z 361 (M+H)$^+$, 721 (2M+H)$^+$.

In a similar manner, Compounds I-78 to I-84 were obtained.

Compound I-78

Melting point: 158-160° C. Recrystallization solvent: ethyl acetate

NMR (CDCl3) d: 1.43 (6H, s), 3.78 (2H, s), 4.59 (2H, s), 4.60 (2H, d, J=4.8 Hz), 7.04-7.09 (2H, m), 7.28-7.36 (7H, m), 7.92 (1H, brs), 12.29 (1H, s).

MS (positive FABMS): m/Z 423 (M+H)$^+$, 845 (2M+H)$^+$.

Compound I-79

Melting point: 168-171° C. Recrystallization solvent: acetone-diethyl ether

NMR (CDCl3) d: 1.43 (6H, s), 3.97 (2H, s), 4.60 (2H, d, J=6.3 Hz), 4.71 (2H, s), 7.04-7.10 (2H, m), 7.23-7.26 (1H, m), 7.32-7.36 (2H, m), 7.43-7.45 (1H, m), 7.69-7.75 (1H, m), 7.91 (1H, t, J=6.3 Hz), 8.57-8.58 (1H, m), 12.31 (1H, s).

Elemental analysis for $C_{22}H_{22}FN_5O_3$

Calcd. (%): C, 62.40; H, 5.24; N, 16.54; F, 4.49.
Found. (%): C, 61.67; H, 5.23; N, 16.23; F, 4.27.

Compound I-80

Melting point: 260-265° C. Recrystallization solvent: acetone-diethyl ether

NMR (CDCl3) d: 1.41 (6H, s), 2.19 (3H, s), 3.73 (2H, s), 4.57 (2H, s), 4.60 (2H, d, J=6.3 Hz), 7.04-7.10 (2H, m), 7.20 (1H, brs), 7.29-7.36 (4H, m), 7.47 (2H, d, J=8.4 Hz), 7.92 (1H, t, J=6.3 Hz), 12.28 (1H, s).

Elemental analysis for $C_{25}H_{26}FN_5O_4$

Calcd. (%): C, 62.62; H, 5.47; N, 14.61; F, 3.96.
Found. (%): C, 62.35; H, 5.54; N, 14.22; F, 3.69.

Compound I-81

Melting point: 204-209° C. Recrystallization solvent: ethyl acetate-diethyl ether NMR (CDCl3) d: 1.41 (6H, s), 3.69 (2H, s), 4.56 (2H, s), 4.60 (2H, d, J=6.3 Hz), 5.22 (1H, brs), 6.79 (2H, d, J=8.4 Hz), 7.04-7.09 (2H, m), 7.17 (2H, d, J=8.4 Hz), 7.31-7.36 (2H, m), 7.92 (1H, t, J=6.3 Hz), 12.28 (1H, s).

Elemental analysis for $C_{23}H_{23}FN_4O_4$

Calcd. (%): C, 63.00; H, 5.29; N, 12.78; F, 4.33.
Found. (%): C, 62.79; H, 5.29; N, 12.49; F, 4.12.

Compound I-82

Melting point: 185-187° C. Recrystallization solvent: ethyl acetate-diethyl ether NMR (CDCl3) d: 1.41 (6H, s), 2.94 (6H, s), 3.67 (2H, s), 4.56 (2H, s), 4.60 (2H, d, J=6.3 Hz), 6.69 (2H, d, J=8.4 Hz), 7.04-7.09 (2H, m), 7.17 (2H, d, J=8.4 Hz), 7.31-7.36 (2H, m), 7.92 (1H, t, J=6.3 Hz), 12.25 (1H, s).

Elemental analysis for $C_{25}H_{28}FN_5O_3$

Calcd. (%): C, 64.50; H, 6.06; N, 15.04; F, 4.08.
Found. (%): C, 65.10; H, 6.16; N, 14.76; F, 3.94.

Compound I-83

Melting point: 202-203° C. Recrystallization solvent: ethyl acetate-diethyl ether NMR (CDCl3) d: 1.48 (6H, s), 3.78 (3H, s), 3.91 (2H, s), 4.61 (2H, d, J=6.3 Hz), 4.68 (2H, s), 6.39-6.44 (2H, m), 6.94 (1H, d, J=8.4 Hz), 7.03-7.10 (2H, m), 7.31-7.36 (2H, m), 7.86 (1H, t, J=6.3 Hz), 8.85 (1H, brs), 12.39 (1H, s).

Elemental analysis for $C_{24}H_{25}FN_4O_5 \cdot 0.5H_2O$

Calcd. (%): C, 60.37; H, 5.49; N, 11.73; F, 3.98.
Found. (%): C, 60.69; H, 5.62; N, 10.83; F, 3.54.

Compound I-84

Melting point: 262° C. Recrystallization solvent: acetone-diethyl ether

NMR (CDCl3) d: 1.27 (6H, s), 1.85 (2H, quint, J=7.5 Hz), 2.62 (2H, t, J=7.5 Hz), 2.69 (2H, t, J=7.5 Hz), 4.59 (2H, d, J=6.3 Hz), 4.76 (2H, s), 7.03-7.09 (2H, m), 7.16-7.21 (2H, m), 7.26-7.36 (5H, m), 7.91 (1H, t, J=6.3 Hz), 12.29 (1H, s).

Elemental analysis for $C_{25}H_{27}FN_4O_3$

Calcd. (%): C, 66.65; H, 6.04; N, 12.44; F, 4.22.
Found. (%): C, 66.65; H, 6.00; N, 12.45; F, 4.08.

Example 31

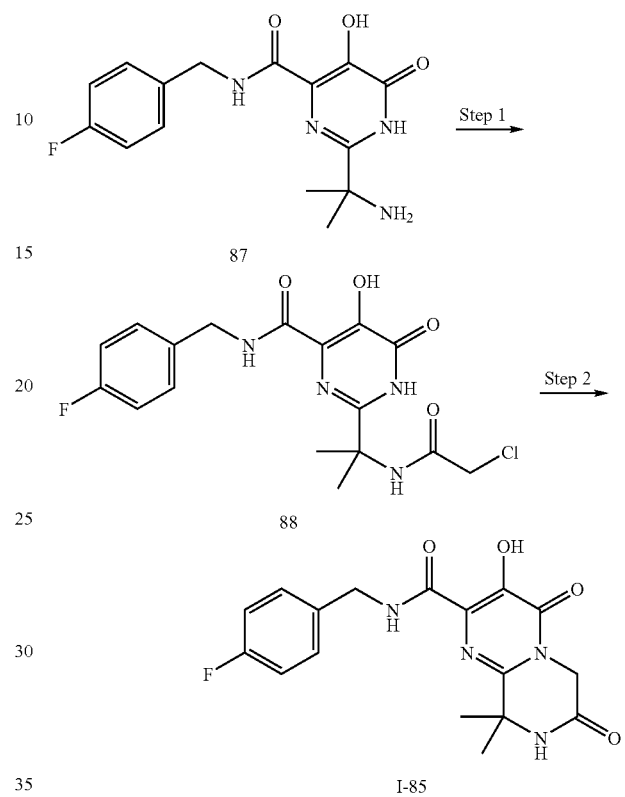

[Formula 58]

Step 1

To a methylene chloride solution of Compound 87 (150 mg, 0.335 mmol) was added triethylamine (139 µl, 1.00 mmol) at room temperature, followed by chloroacetyl chloride (0.0588 ml, 0.738 mmol) under ice-cooling, and the mixture was stirred for 30 minutes. The reaction solution was added with 1N hydrochloric acid, and extracted with chloroform. The extract was washed with saturated brine, and then dried over anhydrous sodium sulfate. A crude product obtained by distilling off the solvent under reduced pressure was dissolved in tetrahydrofuran (6 ml), added with 1N lithium hydroxide solution (0.8 ml) at room temperature, and stirred for 30 minutes. The reaction solution was then added with 1N hydrochloric acid, and extracted with ethyl acetate. The extract was washed with saturated brine, and then dried over anhydrous sodium sulfate. A crystalline residue obtained by distilling off the solvent under reduced pressure was recrystallized from methanol-diisopropylether to give Compound 88 (79 mg, 59% yield) as pale purple crystals.

Step 2

To a dimethylformamide (3.3 ml) solution of Compound 88 (55 mg, 0.139 mmol) was added cesium carbonate (54 mg, 0.166 mmol) at room temperature, and stirred for 30 minutes at 45° C.

The reaction solution was added with 1N hydrochloric acid, and extracted with ethyl acetate. The extract was washed with saturated brine, and then dried over anhydrous sodium sulfate. A crystalline residue obtained by distilling off the solvent under reduced pressure was recrystallized from methanol-diisopropyl ether to give Compound I-85 (31.1 mg, 46% yield) as pale pink crystals.

Melting point: 235-237° C. Recrystallization solvent: methanol-diisopropyl ether NMR (CDCl3) d: 1.57 (3H, s), 1.63 (3H, s), 4.60 (2H, d, J=6.3 Hz), 4.70 (2H, s), 6.56 (1H, brs), 7.03-7.09 (2H, m), 7.30-7.34 (2H, m), 7.72 (1H, brs), 12.23 (1H, s).

MS (positive FABMS): m/Z 361 (M+H)$^+$, 721 (2M+H)$^+$.

Example 32

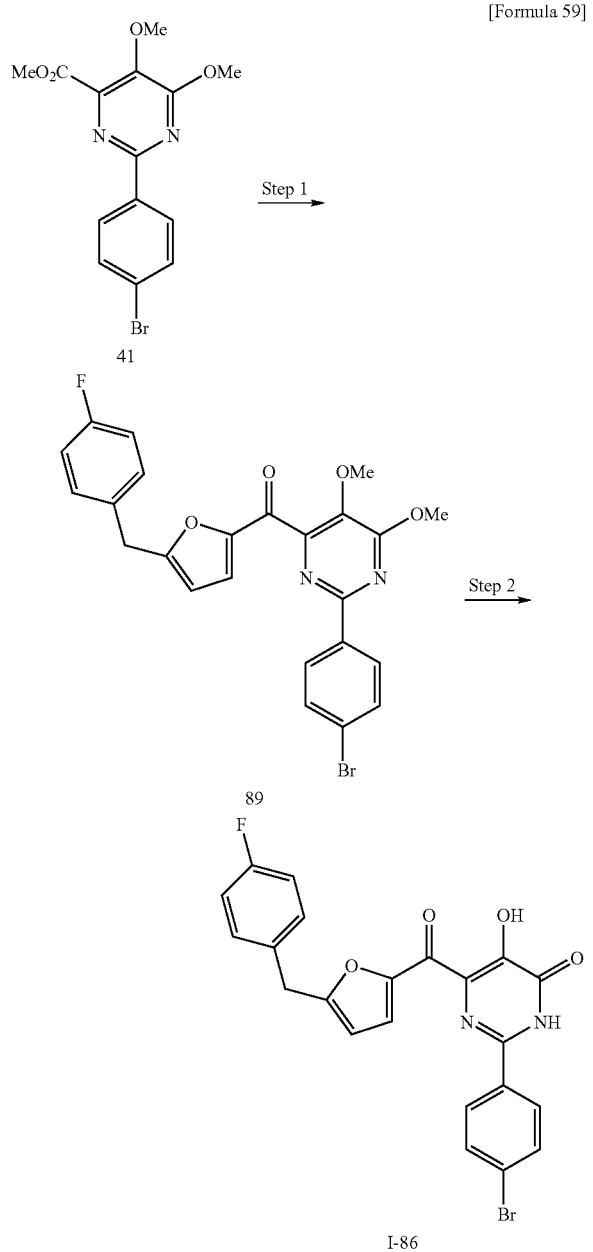

Step 1

2-bromo-5-(4-fluorobenzyl)furan (765 mg, 3.00 mmol) described in Patent (WO 03/016275) was dissolved in tetrahydrofuran (10 ml), and then added with n-butyl lithium (2.5 ml, 4 mmol) at −78° C. After 10 minutes, Compound 41 (1.06 g, 3.00 mmol) obtained from Step 3 of Example 10 was added and stirred for 1 hour. The reaction solution was added with an aqueous solution of saturated ammonium chloride, and extracted with ethyl acetate. The extract was washed with water and saturated brine, and then dried over anhydrous magnesium sulfate. A crude product obtained by distilling off the solvent under reduced pressure was subjected to silica gel chromatography. A fraction of objective product resulting from elution with hexane-ethyl acetate (10:1 v/v) was concentrated under reduced pressure to give Compound 89 (291 mg, 20% yield) as an oily product.

Step 2

Reaction was performed in accordance with the method described in Step 8 of Example 1 using Compound 89 (430 mg, 0.86 mmol) to give Compound I-86 (38 mg, 9% yield) as pale yellow crystals.

Melting point: >270° C. Recrystallization solvent: chloroform

NMR (DMSO-d6) d: 4.15 (2H, s), 6.48 (1H, d, J=3.7 Hz), 7.14-7.20 (2H, m), 7.32-7.37 (2H, m), 7.72 (2H, d, J=8.7 Hz), 7.75 (1H, d, J=3.7 Hz), 7.94 (2H, d, J=8.9 Hz).

Elemental analysis for $C_{22}H_{14}BrFN_2O_4(H_2O)_{0.2}$

Calcd. (%): C, 55.88; H, 3.07; N, 5.92; Br, 16.90; F, 4.02.
Found. (%): C, 55.88; H, 2.99; N, 5.97; Br, 16.94; F, 3.90.

Example 33

The following compound was synthesized in accordance with the method described in Example 32.

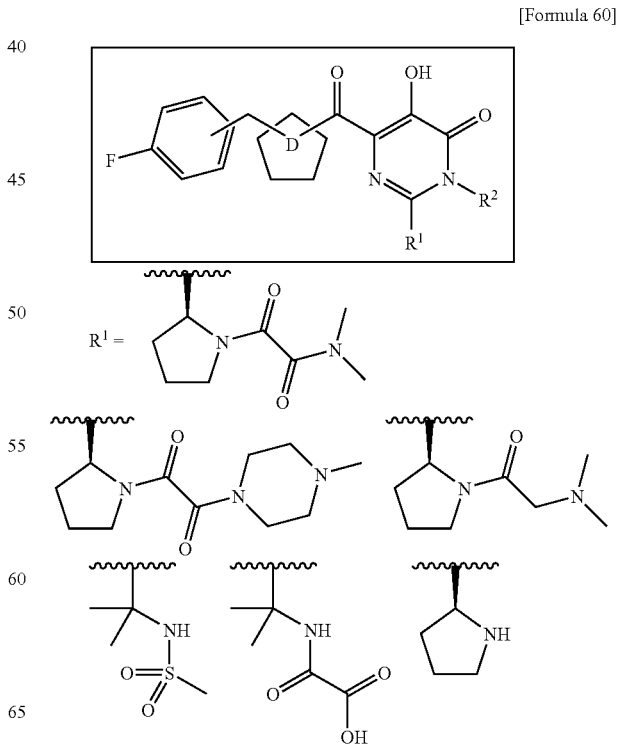

-continued
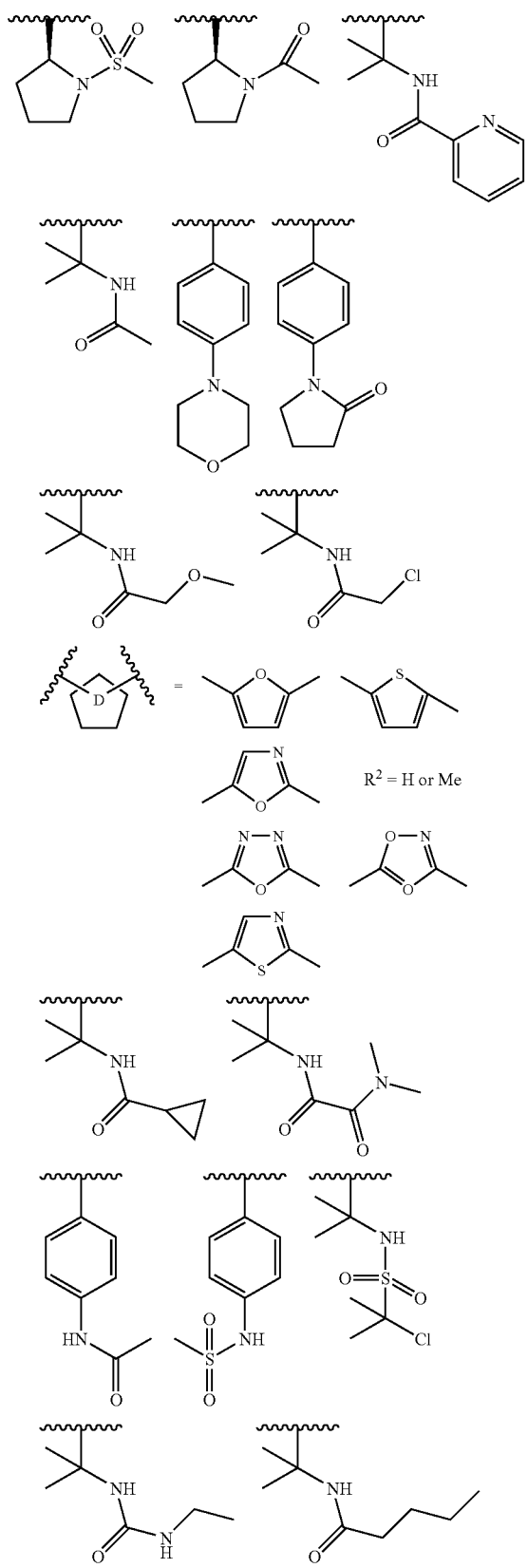
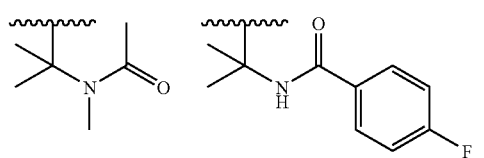
Example 34
The following compound was synthesized in accordance with the methods described in Example 32 and Examples 24 to 31.
[Formula 61]
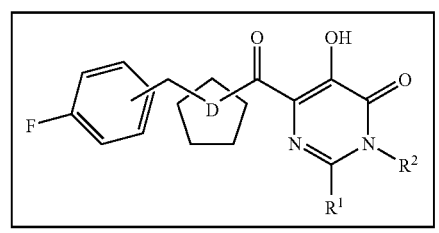
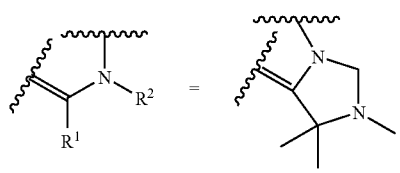
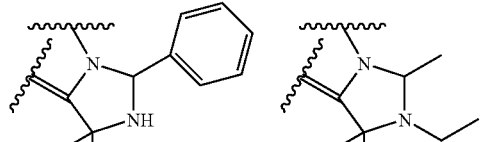
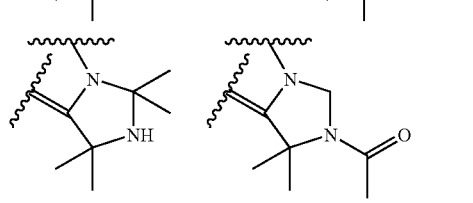
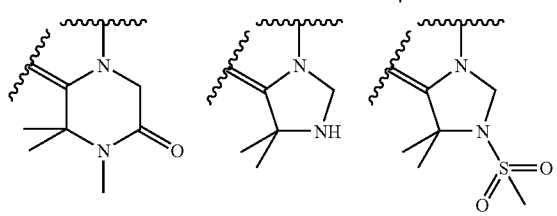

-continued

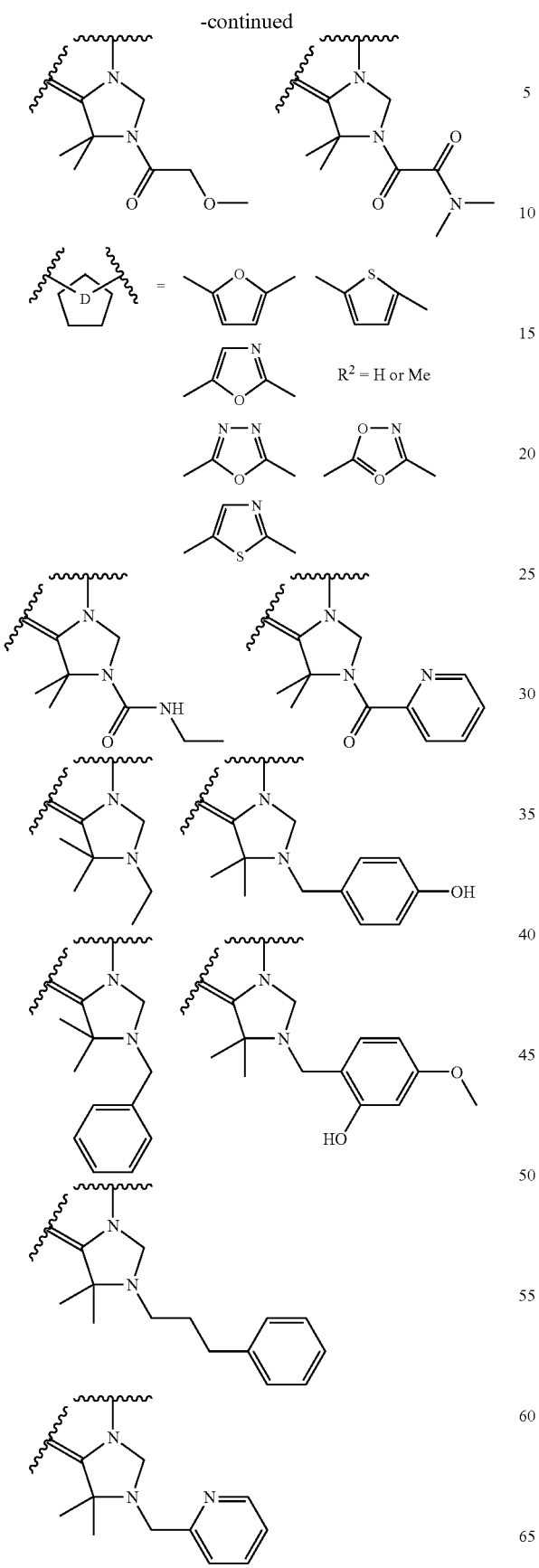
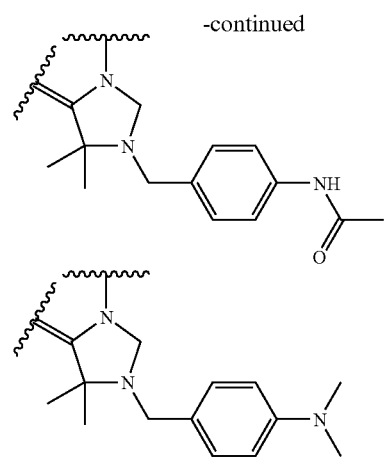

R² = H or Me

Experimental Example 1

The inhibitory activities against integrase were determined by the assay described below.

(1) Preparation of DNA Solutions

A substrate DNA solution (2 pmol/μl) and a target DNA solution (5 pmol/μl) were prepared in the manner as described in Experimental example 1 of WO 2004/024693. Before using the DNA solutions, complementary chains were annealed by slowly cooling after boiling. Substrate DNA and target DNA had sequences as described in that Experimental example.

(2) Determination of Inhibition Rate ($IC_{50}$ Values)

Streptavidin, obtained from Vector Laboratories, was dissolved in 0.1 M carbonate buffer (composition: 90 mM $Na_2CO_3$, 10 mM $NaHCO_3$) at concentration of 40 μg/ml. After coating each well of immunoplates (obtained from NUNC) with 50 μl of the above solution at 4° C. over night, each well was washed twice with PBS (composition: 13.7 mM NaCl, 0.27 mM KCl, 0.43 mM $Na_2HPO_4$, 0.14 mM $KH_2PO_4$) and blocked with 300 μl of 1% skim milk in PBS for 30 min. Additionally, each well was washed twice with PBS and added 50 μl of substrate DNA solution (2 pmol/μl). The immunoplates were kept at room temperature for 30 min while shaking. Then, each well was washed twice with PBS and once with $H_2O$.

Subsequently, in the each well prepared above were added 51 μl of the reaction solution prepared from 12 μl of the buffer (composition: 150 mM MOPS (pH 7.2), 75 mM $MnCl_2$, 50 mM 2-mercaptoethanol, 25% glycerol, 500 μg/ml bovine serum albumin-fraction V), and 39 μl of the distilled water. Then 9 μl of an integrase solution (30 pmol) was added and mixed well. In the well of negative control (NC) was added 9 μl of the integrase dilution buffer (composition: 20 mM MOPS (pH 7.2), 400 mM potassium glutamate, 1 mM EDTA, 0.1% NP-40, 20% glycerol, 1 mM DTT, 4M urea), and mixed well using a plate mixer.

The plates were incubated at 30° C. for 60 minutes. The reaction solution was removed and washed three times with 250 μl of washing buffer (composition: 150 mM MOPS (pH 7.2), 50 mM 2-mercaptoethanol, 25% glycerol, 500 μg/ml bovine serum albumin-fraction V).

Then each well was added with 53 μl of reaction solution prepared from 12 μl of buffer (composition: 150 mM MOPS (pH 7.2), 75 mM $MgCl_2$, 50 mM 2-mercaptoethanol, 25% glycerol, 500 µg/ml bovine serum albumin-fraction V) and 41 µl of distilled water. Further, each well was added with 6 µl of DMSO solution of a compound to be tested, and the well of positive control (PC) was added with 6 µl of DMSO, and mixed well by a plate mixer. After incubating the plate for 30 minutes at 30° C., was added 1 µl of target DNA (5 pmol/µl), and mixed well by a plate mixer.

After incubation for 10 minutes at 30° C., each plate was washed twice with PBS after removal of the reaction solution. Then, 100 µl of ×2000 diluted solution of anti-digoxigenin antibody labeled with alkaline phosphatase (sheep Fab fragment: Boehringer) was added, allowed to bind for 1 hour at 30° C., and washed twice with PBS containing 0.05% Tween20 and once with PBS in this sequence. Next, 150 µl of the Alkaline phosphatase coloring buffer (composition: 10 mM p-Nitrophenylphosphate (obtained from Vector Laboratories), 5 mM $MgCl_2$, 100 mM NaCl, 100 mM Tris-HCl (pH 9.5)) was added and allowed to react for 2 hours at 30° C. Then the reaction was terminated by the addition of 50 µl of 1N NaOH solution. The optical density at 405 nm ($OD_{405nm}$) of each well was measured and the inhibition rate ($IC_{50}$) was determined by the following expression.

The inhibition rate(%)=100[1−{(C abs.−NC abs.)/ (PC abs.−NC abs.)}]

C abs.; the OD of the well of the compound

NC abs.: the OD of the negative control (NC)

PC abs.: the OD of the positive control (PC)

Experimental Example 2

The inhibitory activities against HIV cell proliferation were determined by the assay method described below.

(1) HIV (HTLV-IIIB strain) persistence infection human T-cell strain Molt-4 clone 8 was cultured on RPMI-1640 medium supplemented with 10% fetal bovine serum, and the supernatant was measured for viral titer after filtration, and stored at −80° C. On the other hand, each anti-HIV active agent was diluted in the above culture medium to a predetermined concentration, and each well of a 96-well microplate was added with 50 µl of the resultant active agent solution. Then, 100 µl ($3.5 \times 10^4$ cells) each of MT-4 cell suspension was poured into each well, followed by each 50 µl (60 pfu (plaque forming unit)) of the HIV-containing supernatant diluted with the above culture medium.

(2) After incubating for 4 days in a carbon dioxide incubator at 37° C., every well was added with 30 µl of 3-(4,5-dimethylthiazole-2-yl)-2,5-diphenyltetrazolium bromide (MTT) 5 mg/ml), PBS, and incubated for another 1 hour. At this time, since living cells reduce MTT to cause precipitation of formazane, 150 µl of cell supernatant was removed from each well, and instead 150 µl of lysis solution (isopropanol supplemented with 10% Triton X-100 and 0.4% (v/v) HC) was added, to make formazane eluate by shaking with a plate mixer. Formazane was observed with OD 560 nm and 690 nm (reference wavelength) using a micro reader, and the results were compared with the references. The concentration of Compound at which 50% of cytopathy caused by viruses was inhibited was defined as $EC_{50}$. The results of the above experiment are shown below.

TABLE 1

| Example (Compound No.) | Experimental example 1 ($IC_{50}$, ng/ml) | Experimental example 2 ($EC_{50}$, ng/ml) |
| --- | --- | --- |
| Comparative example 1 | 28 | 19000 |
| 1 (I-1) | 17 | 185 |
| 2 (I-2) | 57 | 38 |
| 4 (I-6) | 24 | 8.8 |
| 5 (I-8) | 4 | 4 |
| 7 (I-10) | 11 | 5 |
| 7 (I-12) | 16 | 1.5 |
| 14 (I-23) | 4.5 | 12 |
| 14 (I-31) | 4.1 | 8.2 |
| 16 (I-34) | 5.1 | 6 |
| 16 (I-40) | 5 | 7.6 |
| 17 (I-45) | 5.8 | 5.6 |
| 19 (I-49) | 7.2 | 27 |
| 20 (I-52) | 13 | 30 |
| 24 (I-60) | 6.6 | 18 |
| 26 (I-64) | 2 | 8.7 |
| 27 (I-65) | 4.5 | 7.6 |
| 30 (I-77) | 4.1 | 10 |
| 30 (I-78) | 1.8 | 7.1 |

Compound of the above Comparative example 1 is Compound G-7b described in WO 03/16275.

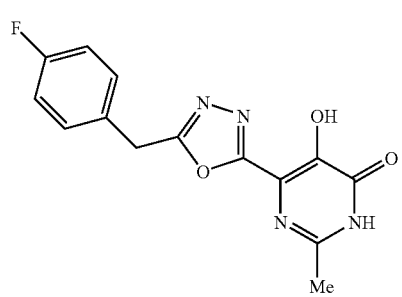

[Formula 62]

Compounds of the present invention showed inhibitory activity against integrase and inhibitory activity against HIV cell proliferation. In particular, as to HIV cell proliferation inhibitory activity, they showed significantly stronger activity than the Compound of Comparative example.

FORMULATION EXAMPLE

The term "active ingredient" means the compounds of the present invention, the tautomers, the prodrugs thereof, their pharmaceutical acceptable salts, or their solvate.

Formulation Example 1

Hard gelatin capsules are prepared using of the following ingredients:

|  | Dose (mg/capsule) |
| --- | --- |
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/tablet) |
| --- | --- |
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient is mixed with ethanol and the admixture added to a portion of the propellant 22, cooled to −30° C. and transferred to a filling device. The required amount is then fed to a stainless steel container and diluted with the reminder of the propellant. The valve units are then fitted to the container.

Formulation Example 4

Tablets, each containing 60 mg of active ingredient, are made as follows.

| Active ingredient | 60 mg |
| --- | --- |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
| --- | --- |
| Starch | 59 mg |
| Microcrystals cellulose | 59 mg |
| Magnesium stearate | 2 mg |
| Total | 200 mg |

The active ingredient, starch, cellulose, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| Active ingredient | 225 mg |
| --- | --- |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution and flavor are diluted with a portion of the water and added, with stirring. Sufficient water is then added to produce the required volume.

Formulation Example 8

An intravenous formulation may be prepared as follows:

| Active ingredient | 100 mg |
|---|---|
| Saturated fatty acid glycerides | 1000 ml |

The solution of the above ingredients is generally administered intravenously to a subject at a rate of 1 ml per minute.

INDUSTRIAL APPLICABILITY

The compounds of the present invention are useful as pharmaceuticals, in particular, as an anti-HIV agent.

The invention claimed is:
1. A compound of the formula:

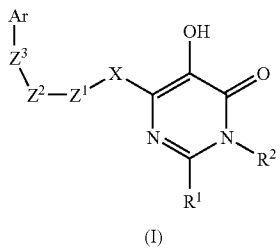

(I)

[Formula 1]

(wherein:
X represents either one of the following groups:

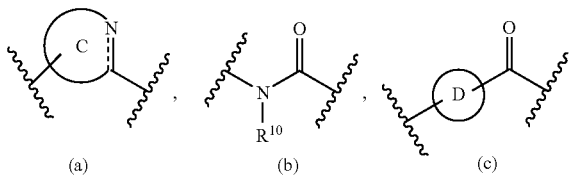

[Formula 2]

(wherein, C ring is nitrogen-containing aromatic heterocyclic ring in which at least one of atoms neighboring the atom bound to the pyrimidine ring is unsubstituted nitrogen atom; $R^{10}$ is hydrogen or lower alkyl; D ring is aryl or heteroaryl, wherein "heteroaryl" means a monocyclic aromatic heterocyclic group and a condensed aromatic heterocyclic group, said monocyclic aromatic heterocyclic group means a group, which is derived from a 5- to 8-membered aromatic ring which may contain 1 to 4 of oxygen atom, sulfur atom, and/or nitrogen atom and which may have a bonding position at any substitutable position, said condensed aromatic heterocyclic group means a group, wherein a 5- to 8-membered aromatic ring which may contain 1 to 4 of oxygen atom, sulfur atom, and/or nitrogen atom is condensed with 1 to 4 of 5- to 8-membered aromatic carbon cycle or the other 5- to 8-membered aromatic heterocyclic ring and which may have a bonding position at the any substitutable position)

$Z^1$ and $Z^3$ each is a single bond;

$Z^2$ is lower alkylene;

Ar is aryl optionally substituted with halogen;

$R^1$ is lower alkyl, substituted lower alkyl, optionally substituted cycloalkyl, optionally substituted cycloalkyl lower alkyl, optionally substituted aryl, optionally substituted aralkyl, optionally substituted 5- or 6-membered nitrogen containing heterocyclic group, or optionally substituted 5- or 6-membered nitrogen containing heterocyclic lower alkyl;

$R^2$ is a hydrogen atom or optionally substituted lower alkyl; or $R^1$ and $R^2$ may form, together with an adjacent atom, an optionally substituted heterocyclic ring, provided that 1) when X is a group shown by (a), $R^1$ is not lower alkyl 2) when X is a group shown by (b), $R^1$ and $R^2$ form, together with an adjacent atom, a heterocyclic ring shown by the (d) as follows:

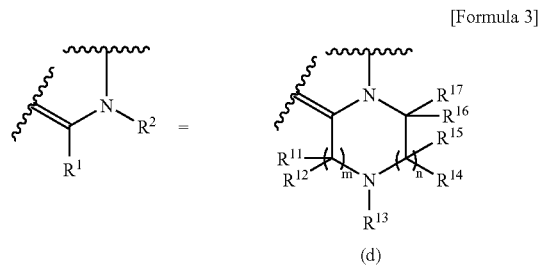

(d)

[Formula 3]

(wherein, $R^{11}$, $R^{12}$, $R^{14}$, $R^{15}$, $R^{16}$, and $R^{17}$ each is independently hydrogen, optionally substituted lower alkyl, optionally substituted aryl, optionally substituted heteroaryl, optionally substituted amino, optionally substituted hydroxy, optionally substituted thiol, optionally substituted sulfonyl or optionally substituted carbamoyl, or $R^{11}$ and $R^{12}$, $R^{14}$ and $R^{15}$, and $R^{16}$ and $R^{17}$ may together form "=O";

$R^{13}$ is hydrogen, optionally substituted lower alkyl, optionally substituted lower alkylcarbonyl, optionally substituted lower alkylsulfonyl, optionally substituted carbamoyl, optionally substituted arylcarbonyl, optionally substituted aralkyl, optionally substituted heteroaralkyl, or optionally substituted heteroarylcarbonyl;

m is 0, 1, 2 or 3; n is 0, 1, 2 or 3; provided that $1 \leq m+n \leq 3$)), or a pharmaceutically acceptable salt thereof, wherein "optionally substituted" means substituted by hydroxy, carboxy, halogen, halo alkyl, alkyl, alkenyl, alkynyl, cycloalkyl, cycloalkenyl, alkoxy, alkenyloxy, alkoxycarbonyl, nitro, nitroso, alkylamino, acylamino, aralkylamino, azide, aryl, aralkyl, cyano, isocyano, isocyanato, thiocyanato, isothiocyanato, mercapto, alkylthio, alkylsulfonyl, alkylcarbamoyl, sulfamoyl, acyl, formyloxy, haloformyl, oxalo, thioformyl, thiocarboxy, dithiocarboxy, thiocarbamoyl, sulfino, sulfo, sulfoamino, hydrazino, ureide, amidino, guanidine, phthalimide, oxo, and heterocyclic ring, wherein "optionally substituted amino" and "optionally substituted carbamoyl" mean substituted by alkyl, benzyl, carbamoylalkyl, mono or di alkylcarbamoyl alkyl, hydroxyalkyl, heterocycle alkyl, alkoxycarbonyl alkyl, mono or di alkylamino alkyl, alkoxyalkyl, acyl, arylcarbonyl, aralkyl, hydroxy, alkyl sulfonyl, arylsulfonyl optionally substituted with alkyl or halogen, cycloalkyl, aryl optionally substituted with alkyl, alkylamino sulfonyl, alkylaminocarbonyl, alkoxycarbonyl, cycloalkylcarbonyl, sulfamoyl, alkyl carbonylamino, heterocycle and amino.

2. The compound according to claim 1, wherein Ar is phenyl optionally substituted with halogen, or a pharmaceutically acceptable salt thereof.

3. The compound according to claim 2, wherein —Z¹—Z²—Z³—Ar is 4-fluorobenzyl, or a pharmaceutically acceptable salt thereof.

4. The compound according to claim 1 represented by the formula:

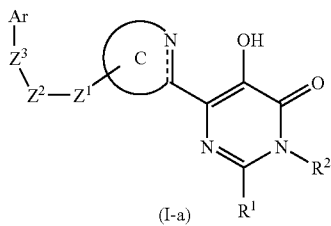

[Formula 4]

(I-a)

(wherein each symbol has the same meanings as claim 1), or a pharmaceutically acceptable salt thereof.

5. The compound according to claim 4, wherein C ring represented by the formula:

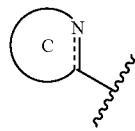

[Formula 5]

is selected from the group consisting of:

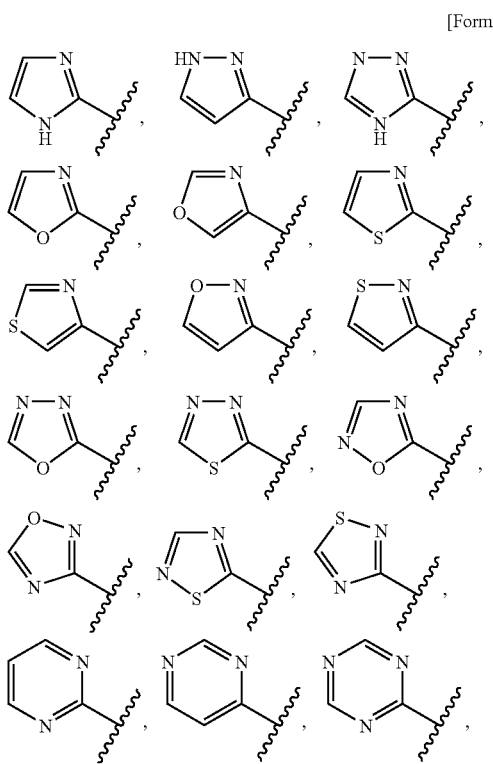

[Formula 6]

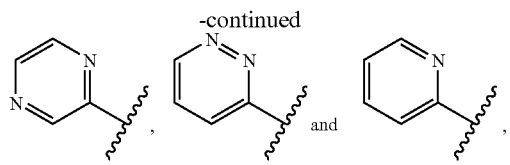

or a pharmaceutically acceptable salt thereof.

6. The compound according to claim 5, wherein C ring is selected from the group consisting of:

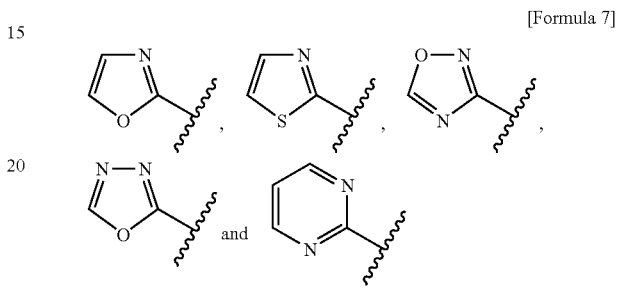

[Formula 7]

or a pharmaceutically acceptable salt thereof.

7. The compound according to claim 1, wherein $R^1$ is substituted lower alkyl, optionally substituted cycloalkyl, optionally substituted aralkyl, optionally substituted 5- or 6-membered nitrogen containing heterocyclic lower alkyl, optionally substituted aryl or optionally substituted 5- or 6-membered nitrogen containing heterocyclic group, and each substituent is selected from the group consisting of —NR³R⁴, —C(=O)R³, —C(=O)NR³R⁴ (wherein, $R^3$ and $R^4$ each is independently, hydrogen atom, hydroxy, alkoxy, optionally substituted aryloxy, optionally substituted aralkyloxy, optionally substituted amino, optionally substituted cycloalkyl, optionally substituted aryl, optionally substituted heterocyclic group, optionally substituted aralkyl, optionally substituted heteroaralkyl, optionally substituted lower alkylcarbonyl, optionally substituted arylcarbonyl, optionally substituted heteroarylcarbonyl, optionally substituted carbamoyl, optionally substituted carbamoylcarbonyl, lower alkoxycarbonylcarbonyl, carboxycarbonyl, lower alkoxycarbonyl, optionally substituted heterocyclic carbonyl, lower alkylsulfonyl, optionally substituted arylsulfonyl, optionally substituted heteroarylsulfonyl, or optionally substituted lower alkylsulfonyl), oxo and halogen, or a pharmaceutically acceptable salt thereof, wherein "optionally substituted" means substituted by hydroxy, carboxy, halogen, halo alkyl, alkyl, alkenyl, alkynyl, cycloalkyl, cycloalkenyl, alkoxy, alkenyloxy, alkoxycarbonyl, nitro, nitroso, alkylamino, acylamino, aralkylamino, azide, aryl, aralkyl, cyano, isocyano, isocyanato, thiocyanato, isothiocyanato, mercapto, alkylthio, alkylsulfonyl, alkylcarbamoyl, sulfamoyl, acyl, formyloxy, haloformyl, oxalo, thioformyl, thiocarboxy, dithiocarboxy, thiocarbamoyl, sulfino, sulfo, sulfoamino, hydrazino, ureide, amidino, guanidine, phthalimide, oxo, and heterocyclic ring, wherein "optionally substituted amino," "optionally substituted carbamoyl" and "optionally substituted carbamoylcarbonyl" mean substituted by alkyl, benzyl, carbamoylalkyl, mono or di alkylcarbamoyl alkyl, hydroxyalkyl, heterocycle alkyl, alkoxycarbonyl alkyl, mono or di alkylamino alkyl, alkoxyalkyl, acyl, arylcarbonyl, aralkyl, hydroxy, alkyl sulfonyl, arylsulfonyl optionally substituted with alkyl or halogen, cycloalkyl, aryl optionally substituted with alkyl, alkylamino sulfonyl, alkylaminocarbonyl, alkoxycarbonyl, cycloalkylcarbonyl, sulfamoyl, alkyl carbonylamino, heterocycle and amino.

8. The compound according to claim 1, wherein $R^1$ is a group selected from the group consisting of:

[Formula 8]

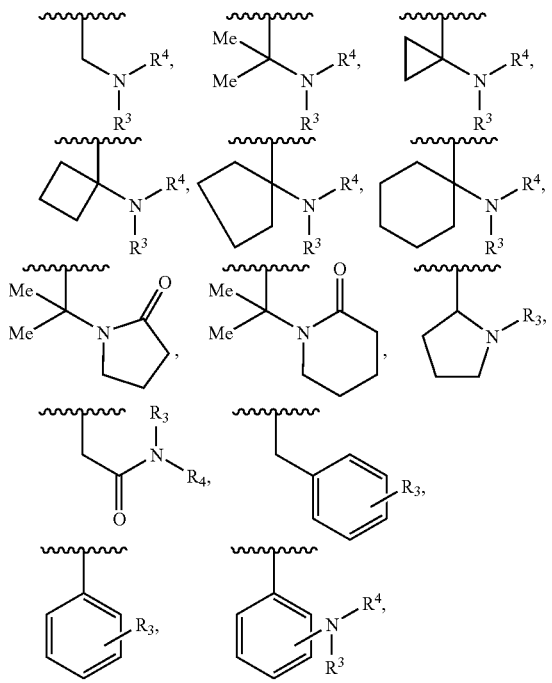

(wherein, $R^3$ and $R^4$ are the same meanings as above), or a pharmaceutically acceptable salt thereof.

9. The compound according to claim 1, wherein Ar is phenyl optionally substituted with halogen; X is a group represented by (a); C ring is a group selected from the group consisting of:

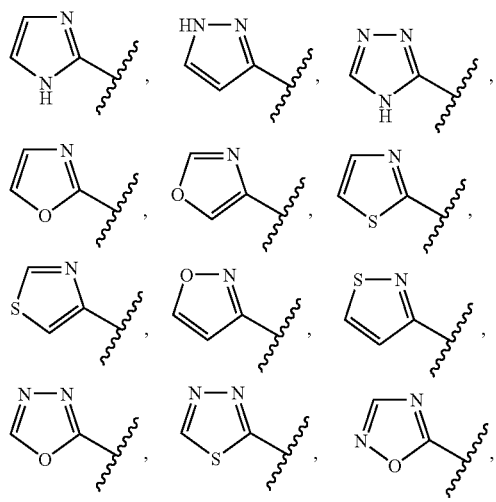

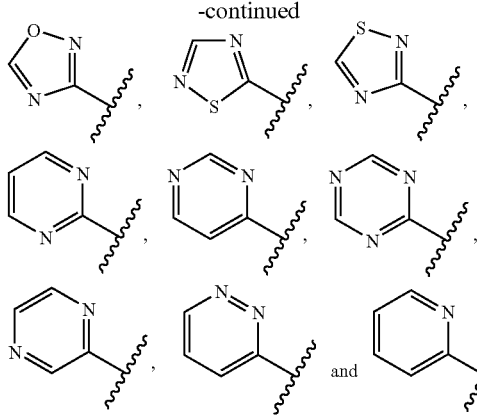

and $R^1$ is substituted lower alkyl, optionally substituted cycloalkyl, optionally substituted aralkyl, optionally substituted 5- or 6-membered nitrogen containing heterocyclic lower alkyl, optionally substituted aryl or optionally substituted 5- or 6-membered nitrogen containing heterocyclic group, and each substituent is selected from the group consisting of —NR$^3$R$^4$, —C(=O)R$^3$, —C(=O)NR$^3$R$^4$ (wherein, $R^3$ and $R^4$ each is independently, hydrogen atom, hydroxy, alkoxy, optionally substituted aryloxy, optionally substituted aralkyloxy, optionally substituted amino, optionally substituted cycloalkyl, optionally substituted aryl, optionally substituted heterocyclic group, optionally substituted aralkyl, optionally substituted heteroaralkyl, optionally substituted lower alkylcarbonyl, optionally substituted arylcarbonyl, optionally substituted heteroarylcarbonyl, optionally substituted carbamoyl, optionally substituted carbamoylcarbonyl, lower alkoxycarbonylcarbonyl, carboxycarbonyl, lower alkoxycarbonyl, optionally substituted heterocyclic carbonyl, lower alkylsulfonyl, optionally substituted arylsulfonyl, optionally substituted heteroarylsulfonyl, or optionally substituted lower alkylsulfonyl), oxo and halogen, or a pharmaceutically acceptable salt thereof, wherein "optionally substituted" means substituted by hydroxy, carboxy, halogen, halo alkyl, alkyl, alkenyl, alkynyl, cycloalkyl, cycloalkenyl, alkoxy, alkenyloxy, alkoxycarbonyl, nitro, nitroso, alkylamino, acylamino, aralkylamino, azide, aryl, aralkyl, cyano, isocyano, isocyanato, thiocyanato, isothiocyanato, mercapto, alkylthio, alkylsulfonyl, alkylcarbamoyl, sulfamoyl, acyl, formyloxy, haloformyl, oxalo, thioformyl, thiocarboxy, dithiocarboxy, thiocarbamoyl, sulfino, sulfo, sulfoamino, hydrazino, ureide, amidino, guanidine, phthalimide, oxo, and heterocyclic ring, wherein "optionally substituted amino," "optionally substituted carbamoyl" and "optionally substituted carbamoylcarbonyl" mean substituted by alkyl, benzyl, carbamoylalkyl, mono or di alkylcarbamoyl alkyl, hydroxyalkyl, heterocycle alkyl, alkoxycarbonyl alkyl, mono or di alkylamino alkyl, alkoxyalkyl, acyl, arylcarbonyl, aralkyl, hydroxy, alkyl sulfonyl, arylsulfonyl optionally substituted with alkyl or halogen, cycloalkyl, aryl optionally substituted with alkyl, alkylamino sulfonyl, alkylaminocarbonyl, alkoxycarbonyl, cycloalkylcarbonyl, sulfamoyl, alkyl carbonylamino, heterocycle and amino.

10. A pharmaceutical composition comprising a compound according to claim 1, or a pharmaceutically acceptable salt thereof, and a pharmaceutically acceptable carrier or diluent.

11. The compound according to claim 9, wherein C ring is selected from the group consisting of:

[Formula 7]

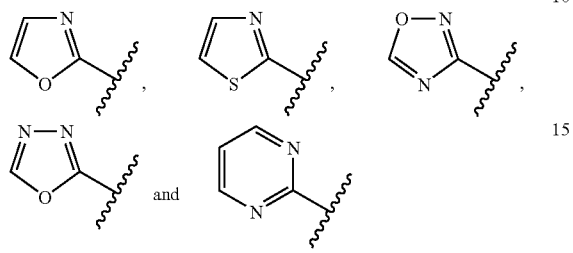

or a pharmaceutically acceptable salt thereof.

12. The compound according to claim 9, wherein $R^1$ is a group selected from the group consisting of:

[Formula 8]

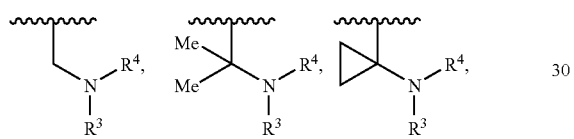

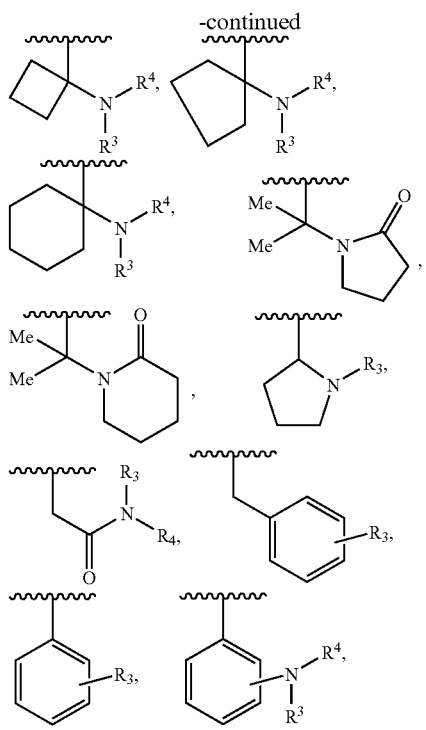

(wherein, $R^3$ and $R^4$ are the same meanings as above), or a pharmaceutically acceptable salt thereof.

* * * * *